US008114980B2

(12) United States Patent
Plaetinck et al.

(10) Patent No.: US 8,114,980 B2
(45) Date of Patent: Feb. 14, 2012

(54) CHARACTERISATION OF GENE FUNCTION USING DOUBLE STRANDED RNA INHIBITION

(75) Inventors: Geert Plaetinck, Zwijnaarde (BE); Christ Platteeuw, Zwijnaarde (BE); Katharine Mortier, Zwijnaarde (BE); Thierry Bogaert, Kortrijk (BE)

(73) Assignee: Devgen NV, Zwijnaarde (BE)

( * ) Notice: Subject to any disclaimer, the term of this patent is extended or adjusted under 35 U.S.C. 154(b) by 98 days.

(21) Appl. No.: 10/826,522

(22) Filed: Apr. 16, 2004

(65) Prior Publication Data

US 2004/0187170 A1 Sep. 23, 2004

Related U.S. Application Data

(62) Division of application No. 10/057,108, filed on Jan. 25, 2002, now abandoned, which is a division of application No. 09/347,311, filed on Jul. 2, 1999, now Pat. No. 7,005,423.

(30) Foreign Application Priority Data

Jul. 3, 1998 (GB) .................................. 9814536.0
Dec. 9, 1998 (GB) .................................. 9827152.1

(51) Int. Cl.
*C07H 21/04* (2006.01)
*C12N 15/11* (2006.01)
*G01N 33/569* (2006.01)
*C12Q 1/68* (2006.01)

(52) U.S. Cl. ..................... 536/24.5; 536/23.1; 415/44 A; 435/7.37; 435/6.1

(58) Field of Classification Search ................. 536/23.1, 536/24.5; 514/44; 435/4, 6; 800/302
See application file for complete search history.

(56) References Cited

U.S. PATENT DOCUMENTS

| | | | |
|---|---|---|---|
| 4,970,168 A | | 11/1990 | Turner |
| 5,017,488 A | * | 5/1991 | McAllister et al. ............ 435/194 |
| 5,459,252 A | * | 10/1995 | Conkling et al. ............. 800/302 |
| 5,569,823 A | | 10/1996 | Shreier et al. |
| 5,679,551 A | * | 10/1997 | Alderete ....................... 435/70.1 |
| 5,691,140 A | * | 11/1997 | Noren et al. ...................... 435/6 |
| 5,837,848 A | * | 11/1998 | Ely et al. ....................... 536/24.1 |
| 5,898,031 A | | 4/1999 | Crooke |
| 5,939,603 A | | 8/1999 | Sela et al. |
| 6,294,712 B1 | | 9/2001 | Kleine et al. |
| 6,506,559 B1 | | 1/2003 | Fire et al. |
| 6,573,099 B2 | * | 6/2003 | Graham ......................... 435/455 |
| 7,538,095 B2 | | 5/2009 | Fire et al. |
| 7,560,438 B2 | | 7/2009 | Fire et al. |
| 7,622,633 B2 | | 11/2009 | Fire et al. |

FOREIGN PATENT DOCUMENTS

| | | |
|---|---|---|
| CA | 2 088 379 A1 | 7/1994 |
| EP | 0 223 452 A2 | 9/1986 |
| EP | 0 426 195 A1 | 5/1991 |
| EP | 0 458 367 A1 | 11/1991 |
| EP | 0 616 035 A2 | 9/1994 |
| GB | 9814536 | 7/1998 |
| GB | 9827152 | 12/1998 |
| WO | WO 86/05516 A1 | 9/1986 |
| WO | WO 90/14090 | 11/1990 |
| WO | WO 99/32619 | 7/1991 |
| WO | WO 91/15111 | 10/1991 |
| WO | WO 93/19188 A1 | 9/1993 |
| WO | WO 95/34680 | 12/1995 |
| WO | WO 96/38553 | 12/1996 |
| WO | WO 96/38555 | 12/1996 |
| WO | WO 97/34926 A2 | 9/1997 |
| WO | WO 98/05770 A2 | 2/1998 |
| WO | WO 98/06750 A2 | 2/1998 |
| WO | WO 98/12335 A1 | 3/1998 |
| WO | WO 98/36083 A1 | 8/1998 |
| WO | WO 9932619 A1 * | 7/1999 |
| WO | WO 99/53050 | 10/1999 |
| WO | WO 99/61631 | 12/1999 |
| WO | WO 00/01846 A1 | 1/2000 |
| WO | WO 03/004644 A1 | 1/2003 |
| WO | WO 2007/035650 A2 | 3/2007 |

OTHER PUBLICATIONS

Talkad et al., Altered mRNA metabolism in ribonuclease III-deficient strains of *Escherichia coli*, Aug. 1978, Journal of Bacteriology, vol. 135, pp. 528-541.*

(Continued)

*Primary Examiner* — Dana Shin
(74) *Attorney, Agent, or Firm* — Wolf, Greenfield & Sacks, P.C.

(57) ABSTRACT

There is provided a method of identifying DNA responsible for conferring a particular phenotype in a cell which method comprises a) constructing a cDNA or genomic library of the DNA of the cell in a suitable vector in an orientation relative to a promoter(s) capable of initiating transcription of the cDNA or DNA to double stranded (ds) RNA upon binding of an appropriate transcription factor to the promoter(s), b) introducing the library into one or more of the cells comprising the transcription factor, and c) identifying and isolating a particular phenotype of the cell comprising the library and identifying the DNA or cDNA fragment from the library responsible for conferring the phenotype. Using this technique it is also possible to assign function to a known DNA sequence by a) identifying a homologue(s) of the DNA sequence in a cell, b) isolating the relevant DNA homologue(s) or a fragment thereof from the cell, c) cloning the homologue or fragment thereof into an appropriate vector in an orientation relative to a suitable promoter(s) capable of initiating transcription of dsRNA from the DNA homologue or fragment upon binding of an appropriate transcription factor to the promoter(s) and d) introducing the vector into the cell from step a) comprising the transcription factor.

14 Claims, 21 Drawing Sheets

OTHER PUBLICATIONS

Studier et al., Use of T7 RNA polymerase to direct expression of cloned genes, 1990, Methods in Enzymology, vol. 185, pp. 60-89.*
Huntley, C.C. et al., "Interference with brome mosaic virus replication by targeting the minus strand promoter," *Journal of General Virology* 1993; 74:2445-2452.
Zdinak, L.A. et al., Transgene-Coded Chimeric Proteins as Reporters of Intracellular Proteolysis: Starvation-Induced Catabolism of a *lacZ* Fusion Protein in Muscle Cells of *Caenorhabditis elegans* 1997; *Journal of Cellular Biochemistry* 67:143-153.
Bendahmane, M. et al., "Engineering resistance against tomato yellow leaf curl virus (TYLCV) using antisense RNA," *Plant Molecular Biology* 1997; 33:351-357.
Nekhotiaeva, N. et al., "Inhibition of *Staphylococcus aureus* Gene Expression and Growth Using Antisense Peptide Nucleic Acids," *Molecular Therapy* Oct. 2004; 10(4):652-659.
Okkema, P.G. et al., Sequence Requirements for Myosin Gene Expression and Regulation in *Caenorhabditis elegans; Genetics* 1993; 135:385-404.
Fire et al., "Proper expression of myosin genes in transgenic nematodes," *The EMBO Journal* 1989; 8(11):3419-3428.
Raftery, K. et al., "Construction of Overlapping Oligonucleotide Templates for the Production of cRNA Standards for Quantitative Reverse Transcription Polymerase Chain Reaction," *Diagnostic Molecular Pathology* 1993; 2:120-124.
Wang, R.F. et al., "Construction of versatile low-copy number vectors for cloning, sequencing and gene expression in *Escherichia coli*," *Gene* 1991; 100:195-199.
Vanfleteren, J.R. et al., "Large scale cultivation of a free-living nematode (*Caenorhabditis elegans*)," *Experentia* 1976; 32:1087-1088.
Kapila, J. et al., "An *Agrobacterium*-mediated transient gene expression system for intact leaves," *Plant Science* 1997; 122:101-108.
Lawrence, E. Henderson's Dictionary of Biological Terms, Tenth Edition, Longman Group UK Limited, 1989, pp. 316-317.
Montgomery, M.K. et al., "Double-stranded RNA as a mediator in sequence-specific genetic silencing and co-suppression," *TIG* Jul. 1998; 14(7):255-258.
Schöb, H. et al., "Silencing of transgenes introduced into leaves by agroinfiltration: a simple, rapid method for investigating sequence requirements for gene silencing," *Mol. Gen. Genet.* 1997; 256:581-585.
Stam, M. et al., "Post-transcriptional silencing of chalcone synthase in *Petunia* by inverted transgene repeats," *The Plant Journal* 1997; 12(1):63-82.
Waterhouse, P.M. et al., "Virus resistance and gene silencing in plants can be induced by simultaneous expression of sense and antisense RNA," *Proc. Natl. Acad. Sci. USA* Nov. 1998; 95:13959-13964.
Lewin, B., Genes V, "Building the transcription complex: promoters, factors, and RNA polymerases," Chapter 29, Oxford University Press 1994; pp. 847-849.
Marathe and Marton, "Cis repeat induced gene silencing in tobacco," Abstract P-1041, *Journal of the Society for in Vitro Biology* 1997; 33(3): 55A.
Correspondence between Sabine Fuss and Claire Tribe, Jul. 13, 2009.
Kadotani et al., RNA silencing in the phytopathogenic fungus *Magnaporthe oryzae*. Mol Plant Microbe Interact. Sep. 2003;16(9):769-76.
Peng et al., Inheritance of gusA and neo genes in transgenic rice. Plant Mol Biol. Jan. 1995;27(1):91-104.
Suzuki et al., Deletion analysis and localization of SbPRP1, a soybean cell wall protein gene, in roots of transgenic tobacco and cowpea. Plant Mol Biol. Jan. 1993;21(1):109-19.
Williamson et al., Nematode pathogenesis and resistance in plants. Plant Cell. Oct. 1996;8(10):1735-45.
[No Author Listed] Regulated plant pest list. US Department of Agriculture, Animal and Plant Health Inspection Service. Available at http://www.aphis.usda.gov/import_export/plants/plan_imports/downloads/RegulatedPestList.pdf). 11 pages, published on Jun. 16, 2000.
[No Author Listed] The Penguin English Dictionary. Merriam-Webster, Inc. 1992. p. 338.
Baum et al., Control of coleopteran insect pests through RNA interference. Nat Biotechnol. Nov. 2007;25(11):1322-6. Epub Nov. 4, 2007.
Code of Laws of the USA, Title 7 USC §147a. 1997, p. 198, section (d) Definitions, also including Title 1, pp. 1-14, Title 7, p. 1,2,197-9.

Darocha et al., Tests of cytoplasmic RNA interference (RNAi) and construction of a tetracycline-inducible T7 promoter system in *Trypanosoma cruzi*. Mol Biochem Parasitol. Feb. 2004;133(2):175-86.
U.S. Appl. No. 60/068,562, filed Dec. 23, 1997, Fire et al.
U.S. Appl. No. 09/056,767, filed Apr. 8, 1998, Waterhouse et al.
U.S. Appl. No. 09/127,735, filed Aug. 3, 1998, Waterhouse et al.
Guo et al., Targeting tumor gene by shRNA-expressing *Salmonella*-mediated RNAi. Gene Ther. Jan. 2011;18(1):95-105. Epub Sep. 2, 2010.
Huvenne et al., Mechanisms of dsRNA uptake in insects and potential RNAi for pest control: A review. J Insect Physiol. 2010;56:227-35.
Isbberg et al., Cultured mammalian cells attach to the invasin protein of *Yersinia pseudotuberculosis*. Proc Natl Acad Sci U S A. Sep. 1988;85(18):6682-6.
Letter from Peter Gibbs of the British Library under the PAD Service dated Feb. 25, 2010 concerning public availability of Montgomery et al., Trends Genet. 1998;14(7):255-8.
Palauqui et al., Systemic acquired silencing: transgene-specific post-transcriptional silencing is transmitted by grafting from silenced stocks to non-silenced scions. EMBO J. Aug. 1, 1997;16(15):4738-45.
Price et al., RNAi-mediated crop protection against insects. Trends Biotechnol. Jul. 2008;26(7):393-400. Epub May 22, 2008.
Rajagopal et al., Silencing of midgut aminopeptidase N of *Spodoptera litura* by double-stranded RNA establishes its role as *Bacillus thuringiensis* toxin receptor. J Biol Chem. Dec. 6, 2002;277(49):46849-51. Epub Oct. 10, 2002.
Ratcliff et al., A similarity between viral defense and gene silencing in plants. Science. Jun. 6, 1997;276(5318):1558-60.
Robinson et al., Improvements in transfection efficiency and tests of RNA interference (RNAi) approaches in the protozoan parasite *Leishmania*. Mol Biochem Parasitol. May 2003;128(2):217-28.
Rodriguez-Cabrera et al., RNAi-mediated knockdown of a *Spodoptera frugiperda* trypsin-like serine-protease gene reduces susceptibility to a *Bacillus thuringiensis* Cry1Ca1 protoxin. Environ Microbiol. Nov. 2010;12(11):2894-903. doi:10.1111/j.1462-2920.2010.02259.x.
Terenius et al., RNA interference in Lepidoptera: an overview of successful and unsuccessful studies and implications for experimental design. J Insect Physiol. Feb. 2011;57(2):231-45. Epub Nov. 20, 2010.
Tian et al., Developmental control of a lepidopteran pest *Spodoptera exigua* by ingestion of bacteria expressing dsRNA of a non-midut gene. Plos ONE. 2009;4(7):e6225.
Third Party Observations under Article 115 EPC dated Jun. 26, 2002, 2 pages.
Urwin et al., Ingestion of double-stranded RNA by preparasitic juvenile cyst nematodes leads to RNA interference. Mol Plant Microbe Interact. Aug. 2002;15(8):747-52.
Walshe et al., Prolonged gene knockdown in the tsetse fly *Glossina* by feeding double stranded RNA. Insect Mol Biol. Feb. 2009;18(1):11-9. Epub Nov. 12, 2008.
Weide et al., Infection-induced expression of the avirulence gene Avr9 in transgenic CF9 tomato plants confers resistance to fungal pathogen attack. Abstract presented at 7th Intl Congress Plant Pathology. Edinburgh, UK. 1998. ICPP98 Paper No. 5.4.12. 1 page.
Xiang et al., Short hairpin RNA-expressing bacteria elicit RNA interference in mammals. Nat Biotechnol. Jun. 2006;24(6):697-702. Epub May 14, 2006.
Submission in preparation for Oral Proceedings mailed Jun. 24, 2008 in connection with EP 01129274.5.
Notice of Opposition filed by BASF against EP 1 197 567 mailed Oct. 7, 2009 in connection with EP 01129274.5.
Response to Opposition mailed May 20, 2010 in connection with EP 01129274.5.
Summons to Attend Oral Proceedings mailed Jul. 7, 2010 in connection with EP 01129274.5.
Written Submission in preparation for Oral Proceedings mailed Aug. 20, 2010 in connection with EP 01129274.5.
Interlocutory Decision in Opposition Proceedings mailed Dec. 7, 2010 in connection with EP 01129274.5.

Commencement of Proceedings before the Board of Appeal mailed Feb. 24, 2011 in connection with EP 01129274.5.
Grounds of Appeal filed by BASF against EP 1 197 567 mailed Apr. 18, 2011 in connection with EP 01129274.5.
Proprietor's Response to Opponent's Grounds of Appeal mailed Sep. 8, 2011 in connection with EP 01129274.5.
Examination Report mailed Sep. 12, 2008 in connection with EP 04011161.9.
Opposition filed by BASF SE against EP 1 484 415 mailed Mar. 8, 2010.
Opposition filed by Bayer S.A.S against EP 1 484 415 mailed Mar. 10, 2010.
Submissions by Devgen N. V. In answer to oppositions lodged by BASF SE and Bayer SAS against EP 1 484 415, mailed Dec. 20, 2010.
Summons to Attend Oral Proceedings mailed Jul. 21, 2011 in connection with EP 04011161.9.
Vennema et al., *Gene* 108(2):201-209 (1991).
Gast, F., *Nucleic Acids Res.* 17(23): 10109 (1989).
Fire et al., *Nature* 391:806-811 (1998).
Bogaert et al., Database Geneseq Acc. No. T71322 (1997) & abstract WO96 38555 (1996).
Chien et al., *Proc Natl Acad Sci USA* 88:9578-9582 (1991).
James et al., Database Medline Acc. No. 97132579, 1996.
James et al., Database EMBL Acc. No. U70025 (1996).
Timmons and Fire, *Nature* 395:854 (1998).
Timmons and Fire, *East Coast Worm Meeting Abstract 180* (Jun. 27, 2002).
Timmons and Fire, East Coast Worm Meeting Abstract 180 (May 12, 1998).
Brenner, S., "The Genetics of *Caenorhabditis elegans*," *Genetics*, vol. 77, (May 1974). pp. 71-94.
Gomes, et al., *Eur. J. Pharm.*, vol. 397, R3-5 (2000).
Derrick, et al., *Nucleic Acid Research*, vol. 21, No. 21, pp. 4948-4953 (1993).
Kessin, R. H., et al., "How cellular slime molds evade nematodes," *Proc. Natl. Acad. Sci.*, vol. 93, (May 1996), pp. 4857-4861.

\* cited by examiner

FIG. 1.

pGN1 gagtgcaccatatgcggtgtgaaataccgcacagatgcgtaaggagaaaataccgcatcaggcgaaattgtaaacgttaatatt
tgttaaaattcgcgttaaatatttgttaaatcagctcatttttaaccaataggccgaaatcggcaaaatcccttataaatcaaaagaat
agaccgagatagggttgagtgttgttccagtttggaacaagagtccactattaaagaacgtggactccaacgtcaaagggcgaa
aaaccgtctatcagggcgatggcccactacgtgaaccatcacccaaatcaagtttttgcggtcgaggtgccgtaaagctctaaat
cggaaccctaaagggagcccccgatttagagcttgacggggaaagccggcgaacgtggcgagaaaggaagggaagaaag
cgaaaggagcgggcgctagggcgctggcaagtgtagcggtcacgctgcgcgtaaccaccacacccgccgcgcttaatgcgc
cgctacagggcgcgtccattcgccattcaggctgcgcaactgttgggaagggcgatcggtgcgggcctcttcgctattacgcca
gctggcgaaaggggggatgtgctgcaaggcgattaagttgggtaacgccagggtttcccagtcacgacgttgtaaaacgacgg
ccagtgaattgtaatacgactcactataggggaattcgagctcggtacccggggatcctctagagtcgaaagcttctcgccctat
agtgagtcgtattacagcttgagtattctatagtgtcacctaaatagcttggcgtaatcatggtcatagctgtttcctgtgtgaaattgtt
atccgctcacaattccacacaacatacgagccggaagcataaagtgtaaagcctggggtgcctaatgagtgagctaactcacatt
aattgcgttgcgctcactgcccgctttccagtcgggaaacctgtcgtgccagctgcattaatgaatcggccaacgcgcggggag
aggcggtttgcgtattgggcgctcttccgcttcctcgctcactgactcgctgcgctcggtcgttcggctgcggcgagcggtatcag
ctcactcaaaggcggtaatacggttatccacagaatcaggggataacgcaggaaagaacatgtgagcaaaaggccagcaaaa
ggccaggaaccgtaaaaaggccgcgttgctggcgtttttcgataggctccgcccccctgacgagcatcacaaaaatcgacgct
caagtcagaggtggcgaaacccgacaggactataaagataccaggcgtttccccctggaagctccctcgtgcgctctcctgttc
cgaccctgccgcttaccggatacctgtccgcctttctcccttcgggaagcgtggcgctttctcatagctcacgctgtaggtatctca
gttcggtgtaggtcgttcgctccaagctgggctgtgtgcacgaaccccccgttcagcccgaccgctgcgccttatccggtaacta
tcgtcttgagtccaacccggtaagacacgacttatcgccactggcagcagccactggtaacaggattagcagagcgaggtatgt
aggcggtgctacagagttcttgaagtggtggcctaactacggctacactagaaggacagtatttggtatctgcgctctgctgaagc
cagttaccttcggaaaaagagttggtagctcttgatccggcaaacaaaccaccgctggtagcggtggtttttttgtttgcaagcagc
agattacgcgcagaaaaaaaggatctcaagaagatcctttgatcttttctacggggtctgacgctcagtggaacgaaaactcacgt
taagggattttggtcatgagattatcaaaaaggatcttcacctagatccttttaaattaaaaatgaagttttaaatcaatctaaagtatat
atgagtaaacttggtctgacagttaccaatgcttaatcagtgaggcacctatctcagcgatctgtctatttcgttcatccatagttgcct
gactccccgtcgtgtagataactacgatacgggagggcttaccatctggccccagtgctgcaatgataccgcgagacccacgct

FIG. 1. (CONTINUED)

caccggctccagatttatcagcaataaaccagccagccggaagggccgagcgcagaagtggtcctgcaactttatccgcctcc
atccagtctattaattgttgccgggaagctagagtaagtagttcgccagttaatagtttgcgcaacgttgttggcattgctacaggca
tcgtggtgtcacgctcgtcgttggtatggcttcattcagctccggttcccaacgatcaaggcgagttacatgatcccccatgttgtg
caaaaaagcggttagctccttcggtcctccgatcgttgtcagaagtaagttggccgcagtgttatcactcatggttatggcagcact
gcataattctcttactgtcatgccatccgtaagatgcttttctgtgactggtgagtactcaaccaagtcattctgagaataccgcgccc
ggcgaccgagttgctcttgcccggcgtcaatacgggataatagtgtatgacatagcagaactttaaaagtgctcatcattggaaaa
cgttcttcggggcgaaaactctcaaggatcttaccgctgttgagatccagttcgatgtaacccactcgtgcacccaactgatcttca
gcatcttttactttcaccagcgttctgggtgagcaaaaacaggaaggcaaaatgccgcaaaaaagggaataagggcgacacg
gaaatgttgaatactcatactcttccttttcaatattattgaagcatttatcagggttattgtctcatgagcggatacatatttgaatgtat
ttagaaaaataaacaaataggggttccgcgcacatttccccgaaaagtgccacctgacgtctaagaaaccattattatcatgacatt
aacctataaaaataggcgtatcacgaggccctttcgtctcgcgcgtttcggtgatgacggtgaaaacctctgacacatgcagctcc
cggagacggtcacagcttgtctgtaagcggatgccgggagcagacaagcccgtcagggcgcgtcagcgggtgttggcgggt
gtcggggctggcttaactatgcggcatcagagcagattgtactga

FIG. 2.

PGN100
ctagcatgaacacgattaacatcgctaagaacgacttctctgacatcgaactggctgctatcccgttcaacactctggctgaccatt
acggtgagcgtttagctcgcgaacagttggcccttgagcatgagtcttacgagatgggtgaagcacgcttccgcaagatgtttga
gcgtcaacttaaagctggtgaggttgcggataacgctgccgccaagcctctcatcactaccctactccctaagatgattgcacgc
atcaacgactggtttgaggaagtgaaagctaagcgcgcggcaagcgccccgacagccttccagttcctgcaagaaatcaagccgga
agccgtagcgtacatcaccattaagaccactctggcttgcctaaccagtgctgacaatacaaccgttcaggctgtagcaagcgca
atcggtcgggccattgaggacgaggctcgcttcggtcgtatccgtgaccttgaagctaagcacttcaagaaaaacgttgaggaa
caactcaacaagcgcgtagggcacgtctacaagaaagcatttatgcaagttgtcgaggctgacatgctctctaagggtctactcg
gtggcgaggcgtggtcttcgtggcataaggaagactctattcatgtaggagtacgctgcatcgagatgctcattgagtcaaccgg
aatggttagcttacaccgccaaaatgctggcgtagtaggtcaagactctgagactatcgaactcgcacctgaatacgctgaggct
atcgcaacccgtgcaggtgcgctggctggcatctctccgatgttccaaccttgcgtagttcctcctaagccgtggactggcattac
tggtggtggctattgggctaacggtcgtcgtcctctggcgctggtgcgtactcacagtaagaaagcactgatgcgctacgaagac
gtttacatgcctgaggtgtacaaagcgattaacattgcgcaaaacaccgcatggaaaatcaacaagaaagtcctagcggtcgcc
aacgtaatcaccaagtggaagcattgtccggtcgaggacatccctgcgattgagcgtgaagaactcccgatgaaaccggaaga
catcgacatgaatcctgaggctctcaccgcgtggaaacgtgctgccgctgctgtgtaccgcaaggacagggctcgcaagtctc
gccgtatcagccttgagttcatgcttgagcaagccaataagtttgctaaccataaggccatctggttcccttacaacatggactggc
gcggtcgtgtttacgccgtgtcaatgttcaacccgcaaggtaacgatatgaccaaaggactgcttacgctggcgaaaggtaaac
caatcggtaaggaaggttactactggctgaaaatccacggtgcaaactgtgcgggtgtcgataaggttccgttccctgagcgcat
caagttcattgaggaaaaccacgagaacatcatggcttgcgctaagtctccactggagaacacttggtgggctgagcaagattct
ccgttctgcttccttgcgttctgctttgagtacgctggggtacagcaccacggcctgagctataactgctcccttccgctggcgtttg
acgggtcttgctctggcatccagcacttctccgcgatgctccgagatgaggtaggtggtcgcgcggttaacttgcttcctagtgag
accgttcaggacatctacgggattgttgctaagaaagtcaacgagattctacaagcagacgcaatcaatgggaccgataacgaa
gtagttaccgtgaccgatgagaacactggtgaaatctctgagaaagtcaagctgggcactaaggcactggctggtcaatggctg
gctcacggtgttactcgcagtgtgactaagcgttcagtcatgacgctggcttacgggtccaaagagttcggcttccgtcaacaagt
gctggaagataccattcagccagctattgattccggcaagggtccgatgttcactcagccgaatcaggctgctggatacatggct
aagctgatttgggaatctgtgagcgtgacggtggtagctgcggttgaagcaatgaactggcttaagtctgctgctaagctgctgg

FIG. 2. (CONTINUED 1)

```
ctgctgaggtcaaagataagaagactggagagattcttcgcaagcgttgcgctgtgcattgggtaactcctgatggtttccctgtgt
ggcaggaatacaagaagcctattcagacgcgcttgaacctgatgttcctcggtcagttccgcttacagcctaccattaacaccaac
aaagatagcgagattgatgcacacaaacaggagtctggtatcgctcctaactttgtacacagccaagacggtagccaccttcgta
agactgtagtgtgggcacacgagaagtacggaatcgaatcttttgcactgattcacgactccttcggtaccattccggctgacgct
gcgaacctgttcaaagcagtgcgcgaaactatggttgacacatatgagtcttgtgatgtactggctgatttctacgaccagttcgct
gaccagttgcacgagtctcaattggacaaaatgccagcacttccggctaaaggtaacttgaacctccgtgacatcttagagtcgg
acttcgcgttcgcgtaaccatggtattgatatctgagctccgcatcggccgctgtcatcagatcgccatctcgcgcccgtgcctctg
acttctaagtccaattactcttcaacatccctacatgctctttctccctgtgctcccacccccattttgttattatcaaaaaaacttcttc
ttaatttctttgttttttagcttcttttaagtcacctctaacaatgaaattgtgtagattcaaaaatagaattaattcgtaataaaaagtcga
aaaaaattgtgctccctcccccattaataataattctatcccaaaatctacacaatgttctgtgtacacttcttatgttttttttacttctga
taaattttttttgaaacatcatagaaaaaaccgcacacaaaataccttatcatatgttacgtttcagtttatgaccgcaattttatttcttc
gcacgtctgggcctctcatgacgtcaaatcatgctcatcgtgaaaaagttttggagtattttttggaattttttcaatcaagtgaaagttta
tgaaattaattttcctgcttttgctttttgggggtttcccctattgtttgtcaagagtttcgaggacggcgtttttcttgctaaaatcacaag
tattgatgagcacgatgcaagaaagatcggaagaaggtttgggtttgaggctcagtggaaggtgagtagaagttgataatttgaa
agtggagtagtgtctatggggttttttgccttaaatgacagaatacattcccaatataccaaacataactgtttcctactagtcggccgt
acggggccctttcgtctcgcgcgtttcggtgatgacggtgaaaacctctgacacatgcagctcccggagacggtcacagcttgtct
gtaagcggatgccgggagcagacaagcccgtcagggcgcgtcagcgggtgttggcgggtgtcggggctggcttaactatgc
ggcatcagagcagattgtactgagagtgcaccatatgcggtgtgaaataccgcacagatgcgtaaggagaaaataccgcatca
ggcggccttaagggcctcgtgatacgcctattttataggttaatgtcatgataataatggtttcttagacgtcaggtggcacttttcg
gggaaatgtgcgcggaacccctatttgtttattttttctaaatacattcaaatatgtatccgctcatgagacaataaccctgataaatgct
tcaataatattgaaaaaggaagagtatgagtattcaacatttccgtgtcgcccttattcccttttttgcggcattttgccttcctgttttg
ctcacccagaaacgctggtgaaagtaaaagatgctgaagatcagttgggtgcacgagtgggttacatcgaactggatctcaaca
gcggtaagatccttgagagttttcgccccgaagaacgttttccaatgatgagcacttttaaagttctgctatgtggcgcggtattatc
ccgtattgacgccgggcaagagcaactcggtcgccgcatacactattctcagaatgacttggttgagtactcaccagtcacagaa
aagcatcttacggatggcatgacagtaagagaattatgcagtgctgccataaccatgagtgataacactgcggccaacttacttct
gacaacgatcggaggaccgaaggagctaaccgcttttttgcacaacatgggggatcatgtaactcgccttgatcgttgggaacc
ggagctgaatgaagccataccaaacgacgagcgtgacaccacgatgcctgtagcaatggcaacaacgttgcgcaaactattaa
ctggcgaactacttactctagcttcccggcaacaattaatagactggatggaggcggataaagttgcaggaccacttctgcgctc
ggcccttccggctggctggttattgctgataaatctggagccggtgagcgtgggtctcgcggtatcattgcagcactggggcca
gatggtaagccctcccgtatcgtagttatctacacgacggggagtcaggcaactatggatgaacgaaatagacagatcgctgag
ataggtgcctcactgattaagcattggtaactgtcagaccaagtttactcatatatactttagattgatttaaaacttcatttttaatttaaa
aggatctaggtgaagatcctttttgataatctcatgaccaaaatcccttaacgtgagttttcgttccactgagcgtcagaccccgtag
aaaagatcaaaggatcttcttgagatcctttttttctgcgcgtaatctgctgcttgcaaacaaaaaaaccaccgctaccagcggtgg
tttgtttgccggatcaagagctaccaactcttttttccgaaggtaactggcttcagcagagcgcagataccaaatactgtccttctagt
gtagccgtagttaggccaccacttcaagaactctgtagcaccgcctacatacctcgctctgctaatcctgttaccagtggctgctgc
cagtggcgataagtcgtgtcttaccgggttggactcaagacgatagttaccggataaggcgcagcggtcgggctgaacggggg
gttcgtgcacacagcccagcttggagcgaacgacctacaccgaactgagatacctacagcgtgagcattgagaaagcgccac
gcttcccgaagggagaaaggcggacaggtatccggtaagcggcagggtcggaacaggagagcgcacgagggagcttcca
gggggaaacgcctggtatctttatagtcctgtcgggtttcgccacctctgacttgagcgtcgatttttgtgatgctcgtcaggggggg
cggagcctatggaaaaacgccagcaacgcggcctttttacggttcctggccttttgctggccttttgctcacatgttctttcctgcgtt
atccctgattctgtggataaccgtattaccgcctttgagtgagctgataccgctcgccgcagccgaacgaccgagcgcagcga
gtcagtgagcgaggaagcggaagagcgcccaatacgcaaaccgcctctccccgcgcgttggccgattcattaatgcagctgg
cacgacaggtttcccgactggaaagcgggcagtgagcgcaacgcaattaatgtgagttagctcactcattaggcaccccaggct
ttacactttatgcttccggctcgtatgttgtgtggaattgtgagcggataacaatttcacacaggaaacagctatgaccatgattacg
ccaagcttgcatgcctgcaggtcgactctagaggatcaagagcattgaatcagaatatggagaacggagcatgagcattttcga
agttttttagatgcactagaacaaagcgtgttggcttcctctgagcccgctttccttatatacccgcattctgcagccttacagaatgtt
```

FIG. 2. (CONTINUED 2)

ctagaaggtcctagatgcattcgtttgaaaatactcccggtgggtgcaaagagacgcagacggaaaatgtatctgggtctctttatt
gtgtacactacttttccatgtaccgaatgtgagtcgccctccttttgcaacaagcagctcgaatgttctagaaaaaggtggaaaata
gtataaataccgttgaaaataaataccgaacaacatttgctctaattgtgaaattagaaatcttcaaactataatcatctcactggatc
cccgggattggccaaaggacccaaaggtatgtttcgaatgatactaacataacatagaacattttcaggaggacccttgg

FIG. 5.
General description of the C.elegans T7 RNA polymerase expression vector with 4 examples
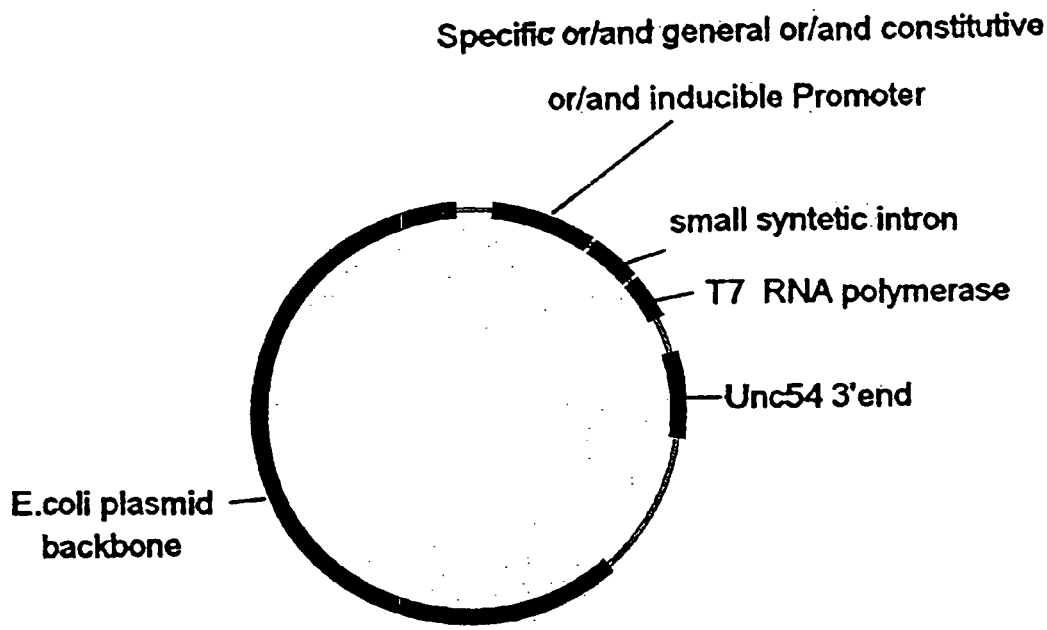
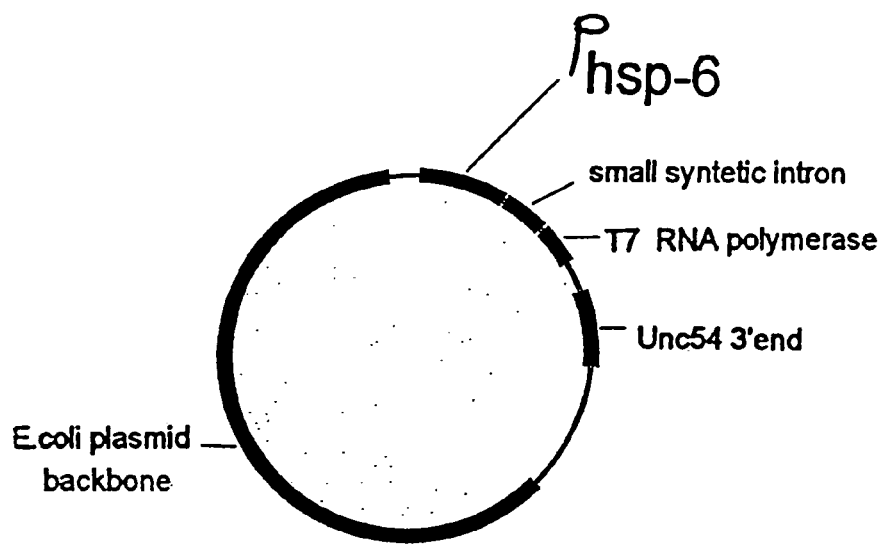

enhanced vector for RNAi, producing
sup35 dsRNA and dsRNA of the library,
gene of interest or PCR product.

FIG. 9
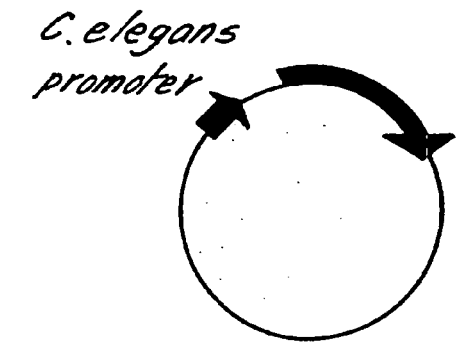
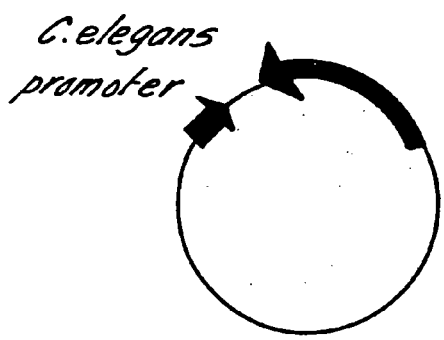
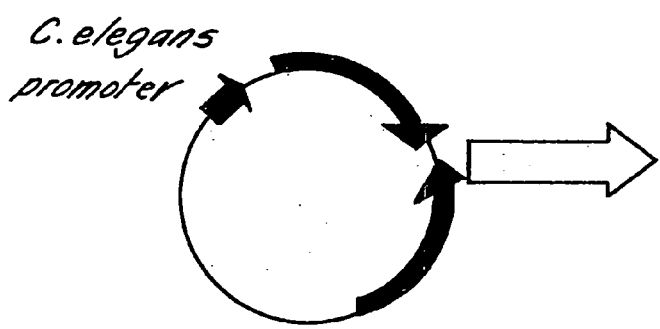
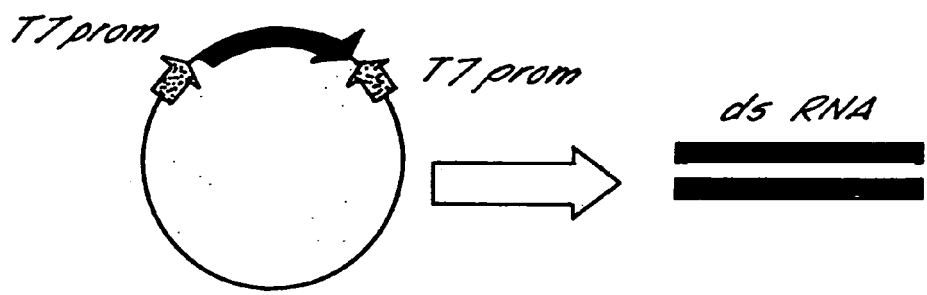

pAS2* with Forward and Reverse T7/T3/Sp6 pGAD424 with Forward and Reverse T7/T3/Sp6

FIG. 19
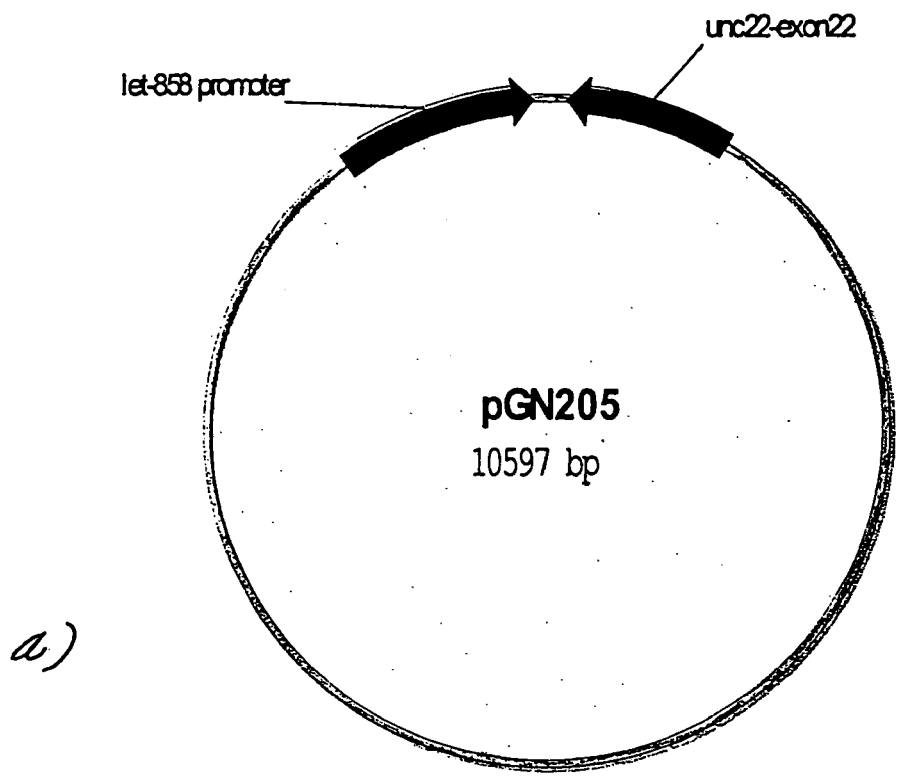
a)
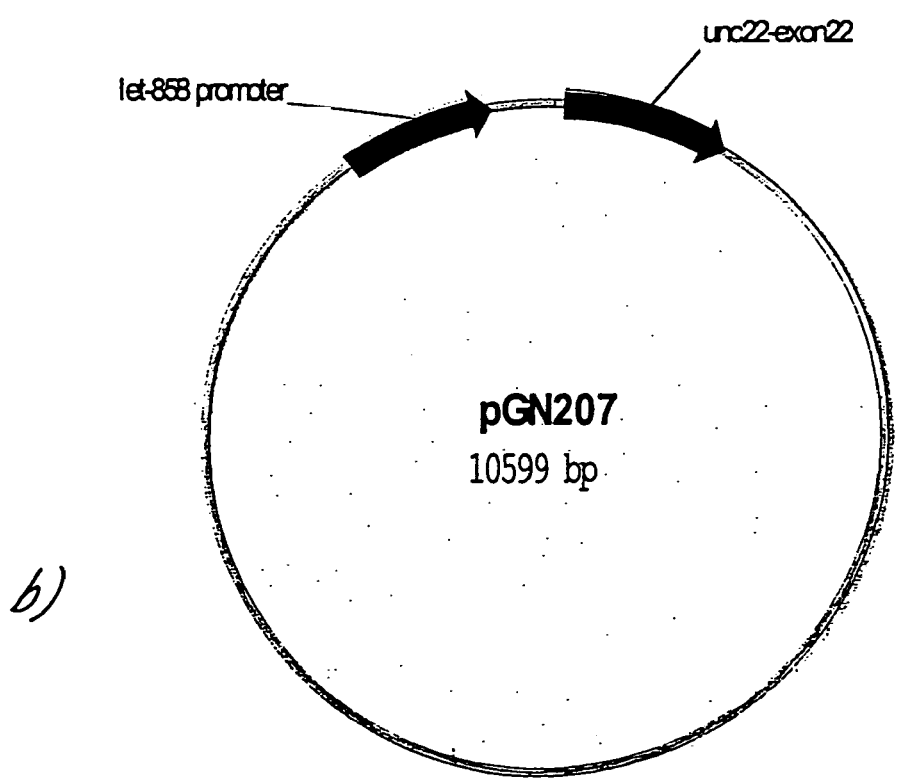
b)

```
                              SEQUENCE LISTING

<160> NUMBER OF SEQ ID NOS: 29

<210> SEQ ID NO 1
<211> LENGTH: 3216
<212> TYPE: DNA
<213> ORGANISM: Artificial Sequence
<220> FEATURE:
<223> OTHER INFORMATION: Description of Artificial Sequence:plasmid DNA

<400> SEQUENCE: 1
gagtgcacca tatgcggtgt gaaataccgc acagatgcgt aaggagaaaa taccgcatca     60
ggcgaaattg taaacgttaa tattttgtta aaattcgcgt taaatatttg ttaaatcagc    120 tcattttta accataggc cgaaatcggc aaaatcccctt ataaatcaaa agaatagacc    180
gagatagggt tgagtgttgt tccagtttgg aacaagagtc cactattaaa gaacgtggac    240
tccaacgtca aagggcgaaa aaccgtctat cagggcgatg gcccactacg tgaaccatca    300
cccaaatcaa gttttttgcg gtcgaggtgc cgtaaagctc taaatcggaa ccctaaaggg    360
agcccccgat ttagagcttg acggggaaag ccggcgaacg tggcgagaaa ggaagggaag    420
aaagcgaaag gagcgggcgc tagggcgctg gcaagtgtag cggtcacgct gcgcgtaacc    480
accacacccg ccgcgcttaa tgcgccgcta cagggcgcgt ccattcgcca ttcaggctgc    540
gcaactgttg gaagggcga tcggtgcggg cctcttcgct attacgccag ctggcgaaag    600
ggggatgtgc tgcaaggcga ttaagttggg taacgccagg gttttcccag tcacgacgtt    660
gtaaaacgac ggccagtgaa ttgtaatacg actcactata gggcgaattc gagctcggta    720
cccggggatc ctctagagtc gaaagcttct cgccctatag tgagtcgtat tacagcttga    780
gtattctata gtgtcaccta aatagcttgg cgtaatcatg gtcatagctg tttcctgtgt    840
gaaattgtta tccgctcaca attccacaca acatacgagc cggaagcata agtgtaaag    900 cctggggtgc ctaatgagtg agctaactca cattaattgc gttgcgctca ctgcccgctt    960
tccagtcggg aaacctgtcg tgccagctgc attaatgaat cggccaacgc gcggggagag   1020
gcggtttgcg tattgggcgc tcttccgctt cctcgctcac tgactcgctg cgctcggtcg   1080
ttcggctgcg gcgagcggta tcagctcact caaaggcggt aatacggtta tccacagaat   1140 cagggataa cgcaggaaag aacatgtgag caaaaggcca gcaaaggcc aggaaccgta   1200 aaaaggccgc gttgctggcg ttttcgata ggctccgccc cctgacgag catcacaaaa   1260 atcgacgctc aagtcagagg tggcgaaacc cgacaggact ataaagatac caggcgtttc   1320 ccccctggaag ctccctcgtg cgctctcctg ttccgaccct gccgcttacc ggatacctgt   1380
ccgcctttct cccttcggga agcgtggcgc tttctcatag ctcacgctgt aggtatctca   1440
gttcggtgta ggtcgttcgc tccaagctgg gctgtgtgca cgaaccccc gttcagcccg    1500 accgctgcgc cttatccggt aactatcgtc ttgagtccaa cccggtaaga cacgacttat   1560
cgccactggc agcagccact ggtaacagga ttagcagagc gaggtatgta ggcggtgcta   1620
cagagttctt gaagtggtgg cctaactacg gctacactag aaggacagta tttggtatct   1680
gcgctctgct gaagccagtt accttcggaa aaagagttgg tagctcttga tccggcaaac   1740
aaaccaccgc tggtagcgt ggtttttttg tttgcaagca gcagattacg cgcagaaaaa   1800
aaggatctca agaagatcct ttgatctttt ctacggggtc tgacgctcag tggaacgaaa   1860
```

-continued

```
actcacgtta agggattttg gtcatgagat tatcaaaaag gatcttcacc tagatccttt     1920
taaattaaaa atgaagtttt aaatcaatct aaagtatata tgagtaaact tggtctgaca     1980
gttaccaatg cttaatcagt gaggcaccta tctcagcgat ctgtctattt cgttcatcca     2040
tagttgcctg actcccgtc gtgtagataa ctacgatacg ggagggctta ccatctggcc      2100
ccagtgctgc aatgataccg cgagaccac gctcaccggc tccagattta tcagcaataa      2160
accagccagc cggaagggcc gagcgcagaa gtggtcctgc aactttatcc gcctccatcc     2220
agtctattaa ttgttgccgg gaagctagag taagtagttc gccagttaat agtttgcgca     2280
acgttgttgg cattgctaca ggcatcgtgg tgtcacgctc gtcgtttggt atggcttcat     2340
tcagctccgg ttcccaacga tcaaggcgag ttacatgatc ccccatgttg tgcaaaaaag    2400
cggttagctc cttcggtcct ccgatcgttg tcagaagtaa gttggccgca gtgttatcac     2460
tcatggttat ggcagcactg cataattctc ttactgtcat gccatccgta agatgctttt    2520
ctgtgactgg tgagtactca accaagtcat tctgagaata ccgcgccgg cgaccgagtt     2580 gctcttgccc ggcgtcaata cgggataata gtgtatgaca tagcagaact ttaaaagtgc    2640
tcatcattgg aaaacgttct tcggggcgaa aactctcaag gatcttaccg ctgttgagat    2700
ccagttcgat gtaacccact cgtgcaccca actgatcttc agcatctttt actttcacca    2760
gcgtttctgg gtgagcaaaa acaggaaggc aaaatgccgc aaaaaaggga ataagggcga    2820
cacggaaatg ttgaatactc atactcttcc tttttcaata ttattgaagc atttatcagg    2880
gttattgtct catgagcgga tacatatttg aatgtattta gaaaaataaa caaatagggg    2940
ttccgcgcac atttccccga aaagtgccac ctgacgtcta agaaaccatt attatcatga    3000
cattaaccta taaaaatagg cgtatcacga ggcccttcg tctcgcgcgt ttcggtgatg     3060
acggtgaaaa cctctgacac atgcagctcc cggagacggt cacagcttgt ctgtaagcgg    3120
atgccgggag cagacaagcc cgtcaggcg cgtcagcggg tgttggcggg tgtcggggct     3180
ggcttaacta tgcggcatca gagcagattg tactga                              3216
```

<210> SEQ ID NO 2
<211> LENGTH: 6460
<212> TYPE: DNA
<213> ORGANISM: Artificial Sequence
<220> FEATURE:
<223> OTHER INFORMATION: Description of Artificial Sequence:plasmid DNA

<400> SEQUENCE: 2

```
ctagcatgaa cacgattaac atcgctaaga acgacttctc tgacatcgaa ctggctgcta      60
tcccgttcaa cactctggct gaccattacg gtgagcgttt agctcgcgaa cagttggccc     120
ttgagcatga gtcttacgag atgggtgaag cacgcttccg caagatgttt gagcgtcaac     180
ttaaagctgg tgaggttgcg gataacgctg ccgccaagcc tctcatcact accctactcc    240
ctaagatgat tgcacgcatc aacgactggt ttgaggaagt gaaagctaag cgcggcaagc    300
gcccgacagc cttccagttc ctgcaagaaa tcaagccgga agccgtagcg tacatcacca    360
ttaagaccac tctggcttgc ctaaccagtg ctgacaatac aaccgttcag gctgtagcaa    420
gcgcaatcgg tcgggccatt gaggacgagg ctcgcttcgg tcgtatccgt gaccttgaag    480
ctaagcactt caagaaaaac gttgaggaac aactcaacaa gcgcgtaggg cacgtctaca    540
agaaagcatt tatgcaagtt gtcgaggctg acatgctctc taagggtcta ctcggtggcg    600
aggcgtggtc ttcgtggcat aaggaagact ctattcatgt aggagtacgc tgcatcgaga    660
tgctcattga gtcaaccgga atggttagct tacaccgcca aatgctggc gtagtaggtc     720
```

```
aagactctga gactatcgaa ctcgcacctg aatacgctga ggctatcgca acccgtgcag    780
gtgcgctggc tggcatctct ccgatgttcc aaccttgcgt agttcctcct aagccgtgga    840
ctggcattac tggtggtggc tattgggcta acggtcgtcg tcctctggcg ctggtgcgta    900
ctcacagtaa gaaagcactg atgcgctacg aagacgttta catgcctgag gtgtacaaag    960
cgattaacat tgcgcaaaac accgcatgga aaatcaacaa gaaagtccta gcggtcgcca   1020
acgtaatcac caagtggaag cattgtccgg tcgaggacat ccctgcgatt gagcgtgaag   1080
aactcccgat gaaaccggaa gacatcgaca tgaatcctga ggctctcacc gcgtggaaac   1140
gtgctgccgc tgctgtgtac cgcaaggaca gggctcgcaa gtctcgccgt atcagccttg   1200
agttcatgct tgagcaagcc aataagtttg ctaaccataa ggccatctgg ttcccttaca   1260
acatggactg gcgcggtcgt gtttacgccg tgtcaatgtt caacccgcaa ggtaacgata   1320
tgaccaaagg actgcttacg ctggcgaaag gtaaaccaat cggtaaggaa ggttactact   1380
ggctgaaaat ccacggtgca aactgtgcgg gtgtcgataa ggttccgttc cctgagcgca   1440
tcaagttcat tgaggaaaac cacgagaaca tcatggcttg cgctaagtct ccactggaga   1500
acacttggtg ggctgagcaa gattctccgt tctgcttcct tgcgttctgc tttgagtacg   1560
ctggggtaca gcaccacggc ctgagctata actgctccct tccgctggcg tttgacgggt   1620
cttgctctgg catccagcac ttctccgcga tgctccgaga tgaggtaggt ggtcgcgcgg   1680
ttaacttgct tcctagtgag accgttcagg acatctacgg gattgttgct aagaaagtca   1740
acgagattct acaagcagac gcaatcaatg ggaccgataa cgaagtagtt accgtgaccg   1800
atgagaacac tggtgaaatc tctgagaaag tcaagctggg cactaaggca ctggctggtc   1860
aatggctggc tcacggtgtt actcgcagtg tgactaagcg ttcagtcatg acgctggctt   1920
acgggtccaa agagttcggc ttccgtcaac aagtgctgga agataccatt cagccagcta   1980
ttgattccgg caagggtccg atgttcactc agccgaatca ggctgctgga tacatggcta   2040
agctgatttg ggaatctgtg agcgtgacgg tggtagctgc ggttgaagca atgaactggc   2100
ttaagtctgc tgctaagctg ctggctgctg aggtcaaaga taagaagact ggagagattc   2160
ttcgcaagcg ttgcgctgtg cattgggtaa ctcctgatgg tttccctgtg tggcaggaat   2220
acaagaagcc tattcagacg cgcttgaacc tgatgttcct cggtcagttc cgcttacagc   2280
ctaccattaa caccaacaaa gatagcgaga ttgatgcaca caaacaggag tctggtatcg   2340
ctcctaactt tgtacacagc caagacggta gccaccttcg taagactgta gtgtgggcac   2400
acgagaagta cggaatcgaa tcttttgcac tgattcacga ctccttcggt accattccgg   2460
ctgacgctgc gaacctgttc aaagcagtgc gcgaaactat ggttgacaca tatgagtctt   2520
gtgatgtact ggctgatttc tacgaccagt tcgctgacca gttgcacgag tctcaattgg   2580
acaaaatgcc agcacttccg gctaaaggta acttgaacct ccgtgacatc ttagagtcgg   2640
acttcgcgtt cgcgtaacca tggtattgat atctgagctc cgcatcggcc gctgtcatca   2700
gatcgccatc tcgcgcccgt gcctctgact tctaagtcca attactcttc aacatcccta   2760
catgctcttt ctccctgtgc tcccaccccc tattttttgtt attatcaaaa aaacttcttc   2820
ttaatttctt tgtttttttag cttctttttaa gtcacctcta acaatgaaat tgtgtagatt   2880
caaaaataga attaattcgt aataaaaagt cgaaaaaaat tgtgctccct ccccccatta   2940
ataataattc tatcccaaaa tctacacaat gttctgtgta cacttcttat gttttttta    3000
cttctgataa attttttttg aaacatcata gaaaaaccg cacacaaaat accttatcat   3060
atgttacgtt tcagtttatg accgcaattt ttatttcttc gcacgtctgg gcctctcatg   3120
```

```
acgtcaaatc atgctcatcg tgaaaaagtt ttggagtatt tttggaattt ttcaatcaag   3180
tgaaagttta tgaaattaat tttcctgctt ttgcttttg ggggtttccc ctattgtttg   3240
tcaagagttt cgaggacggc gttttcttg ctaaaatcac aagtattgat gagcacgatg   3300
caagaaagat cggaagaagg tttgggtttg aggctcagtg aaggtgagt agaagttgat   3360
aatttgaaag tggagtagtg tctatgggt ttttgccta aatgacagaa tacattccca   3420
atataccaaa cataactgtt tcctactagt cggccgtacg ggccctttcg tctcgcgcgt   3480
ttcggtgatg acggtgaaaa cctctgacac atgcagctcc cggagacggt cacagcttgt   3540
ctgtaagcgg atgccgggag cagacaagcc cgtcagggcg cgtcagcggg tgttggcggg   3600
tgtcggggct ggcttaacta tgcggcatca gagcagattg tactgagagt gcaccatatg   3660
cggtgtgaaa taccgcacag atgcgtaagg agaaaatacc gcatcaggcg gccttaaggg   3720
cctcgtgata cgcctatttt tataggttaa tgtcatgata ataatggttt cttagacgtc   3780
aggtggcact tttcggggaa atgtgcgcgg aaccctatt tgtttatttt tctaaataca   3840
ttcaaatatg tatccgctca tgagacaata accctgataa atgcttcaat aatattgaaa   3900
aaggaagagt atgagtattc aacatttccg tgtcgccctt attccctttt ttgcggcatt   3960
ttgccttcct gttttgctc acccagaaac gctggtgaaa gtaaaagatg ctgaagatca   4020
gttgggtgca cgagtgggtt acatcgaact ggatctcaac agcggtaaga tccttgagag   4080
ttttcgcccc gaagaacgtt ttccaatgat gagcactttt aaagttctgc tatgtggcgc   4140
ggtattatcc cgtattgacg ccgggcaaga gcaactcggt cgccgcatac actattctca   4200
gaatgacttg gttgagtact caccagtcac agaaaagcat cttacggatg gcatgacagt   4260
aagagaatta tgcagtgctg ccataaccat gagtgataac actgcggcca acttacttct   4320
gacaacgatc ggaggaccga aggagctaac cgctttttg cacaacatgg ggatcatgt    4380
aactcgcctt gatcgttggg aaccggagct gaatgaagcc ataccaaacg acgagcgtga   4440
caccacgatg cctgtagcaa tggcaacaac gttgcgcaaa ctattaactg gcgaactact   4500
tactctagct tcccggcaac aattaataga ctggatggag gcggataaag ttgcaggacc   4560
acttctgcgc tcggcccttc cggctggctg gtttattgct gataaatctg gagccggtga   4620
gcgtgggtct cgcggtatca ttgcagcact ggggccagat ggtaagccct cccgtatcgt   4680
agttatctac acgacgggga gtcaggcaac tatggatgaa cgaaatagac agatcgctga   4740
gataggtgcc tcactgatta agcattggta actgtcagac caagtttact catatatact   4800
ttagattgat ttaaaacttc atttttaatt taaaaggatc taggtgaaga tcctttttga   4860
taatctcatg accaaaatcc cttaacgtga gttttcgttc cactgagcgt cagaccccgt   4920
agaaaagatc aaaggatctt cttgagatcc ttttttctg cgcgtaatct gctgcttgca   4980
aacaaaaaaa ccaccgctac cagcggtggt ttgtttgccg gatcaagagc taccaactct   5040
ttttccgaag gtaactggct tcagcagagc gcagatacca atactgtcc ttctagtgta   5100
gccgtagtta ggccaccact tcaagaactc tgtagcaccg cctacatacc tcgctctgct   5160
aatcctgtta ccagtggctg ctgccagtgg cgataagtcg tgtcttaccg ggttggactc   5220
aagacgatag ttaccggata aggcgcagcg gtcgggctga acggggggtt cgtgcacaca   5280
gcccagcttg gagcgaacga cctacaccga actgagatac ctacagcgtg agcattgaga   5340
aagcgccacg cttcccgaag ggagaaaggc ggacaggtat ccggtaagcg cagggtcgg    5400
aacaggagag cgcacgaggg agcttccagg gggaaacgcc tggtatcttt atagtcctgt   5460
cgggtttcgc cacctctgac ttgagcgtcg attttttgtga tgctcgtcag ggggcggag   5520
```

| | |
|---|---|
| cctatggaaa aacgccagca acgcggcctt tttacggttc ctggcctttt gctggccttt | 5580 |
| tgctcacatg ttctttcctg cgttatcccc tgattctgtg gataaccgta ttaccgcctt | 5640 |
| tgagtgagct gataccgctc gccgcagccg aacgaccgag cgcagcgagt cagtgagcga | 5700 |
| ggaagcggaa gagcgcccaa tacgcaaacc gcctctcccc gcgcgttggc cgattcatta | 5760 |
| atgcagctgg cacgacaggt ttcccgactg gaaagcgggc agtgagcgca acgcaattaa | 5820 |
| tgtgagttag ctcactcatt aggcacccca ggctttacac tttatgcttc cggctcgtat | 5880 |
| gttgtgtgga attgtgagcg gataacaatt tcacacagga aacagctatg accatgatta | 5940 |
| cgccaagctt gcatgcctgc aggtcgactc tagaggatca gagcatttg aatcagaata | 6000 |
| tggagaacgg agcatgagca ttttcgaagt tttttagatg cactagaaca aagcgtgttg | 6060 |
| gcttcctctg agcccgcttt ccttatatac ccgcattctg cagccttaca gaatgttcta | 6120 |
| gaaggtccta gatgcattcg tttgaaaata ctcccggtgg gtgcaaagag acgcagacgg | 6180 |
| aaaatgtatc tgggtctctt tattgtgtac actactttc catgtaccga atgtgagtcg | 6240 |
| ccctcctttt gcaacaagca gctcgaatgt tctagaaaaa ggtggaaaat agtataaata | 6300 |
| ccgttgaaaa taaataccga acaacatttg ctctaattgt gaaattagaa atcttcaaac | 6360 |
| tataatcatc tcactggatc cccgggattg gccaaaggac ccaaaggtat gtttcgaatg | 6420 |
| atactaacat aacatagaac attttcagga ggacccttgg | 6460 |

<210> SEQ ID NO 3
<211> LENGTH: 8330
<212> TYPE: DNA
<213> ORGANISM: Artificial Sequence
<220> FEATURE:
<223> OTHER INFORMATION: Description of Artificial Sequence:plasmid DNA

<400> SEQUENCE: 3

| | |
|---|---|
| gttgtcgtaa agagatgttt ttatttact ttacaccggg tcctctctct ctgccagcac | 60 |
| agctcagtgt tggctgtgtg ctcgggctcc tgccaccggc ggcctcatct tcttcttctt | 120 |
| cttctctcct gctctcgctt atcacttctt cattcattct tattccttt catcatcaaa | 180 |
| ctagcatttc ttactttatt tattttttc aattttcaat tttcagataa aaccaaacta | 240 |
| cttgggttac agccgtcaac agatccccgg gattggccaa aggacccaaa ggtatgtttc | 300 |
| gaatgatact aacataacat agaacatttt caggaggacc cttgcttgga gggtaccgga | 360 |
| tgactgctcc aaagaagaag cgtaagctca tgaacacgat taacatcgct aagaacgact | 420 |
| tctctgacat cgaactggct gctatcccgt tcaacactct ggctgaccat tacggtgagc | 480 |
| gtttagctcg cgaacagttg gcccttgagc atgagtctta cgagatgggt gaagcacgct | 540 |
| tccgcaagat gtttgagcgt caacttaaag ctggtgaggt tgcggataac gctgccgcca | 600 |
| agcctctcat cactacccta ctccctaaga tgattgcacg catcaacgac tggtttgagg | 660 |
| aagtgaaagc taagcgcggc aagcgcccga cagccttcca gttcctgcaa gaaatcaagc | 720 |
| cggaagccgt agcgtacatc accattaaga ccactctggc ttgcctaacc agtgctgaca | 780 |
| atacaaccgt tcaggctgta gcaagcgcaa tcggtcgggc cattgaggac gaggctcgct | 840 |
| tcggtcgtat ccgtgacctt gaagctaagc acttcaagaa aaacgttgag gaacaactca | 900 |
| acaagcgcgt agggcacgtc tacaagaaag catttatgca agttgtcgag gctgacatgc | 960 |
| tctctaaggg tctactcggt ggcgaggcgt ggtcttcgtg gcataaggaa gactctattc | 1020 |
| atgtaggagt acgctgcatc gagatgctca ttgagtcaac cggaatggtt agcttacacc | 1080 |
| gccaaaatgc tggcgtagta ggtcaagact ctgagactat cgaactcgca cctgaatacg | 1140 |

```
ctgaggctat cgcaacccgt gcaggtgcgc tggctggcat ctctccgatg ttccaacctt    1200
gcgtagttcc tcctaagccg tggactggca ttactggtgg tggctattgg gctaacggtc    1260
gtcgtcctct ggcgctggtg cgtactcaca gtaagaaagc actgatgcgc tacgaagacg    1320
tttacatgcc tgaggtgtac aaagcgatta acattgcgca aaacaccgca tggaaaatca    1380
acaagaaagt cctagcggtc gccaacgtaa tcaccaagtg gaagcattgt ccggtcgagg    1440
acatccctgc gattgagcgt gaagaactcc cgatgaaacc ggaagacatc gacatgaatc    1500
ctgaggctct caccgcgtgg aaacgtgctg ccgctgctgt gtaccgcaag acaaggctcg    1560
caagtctcgc cgtatcagcc ttgagttcat gcttgagcaa gccataagt ttgctaacca    1620 taaggccatc tggttccctt acaacatgga ctggcgcggt tcgtgtttac gctgtgtcaa    1680
tgttcaaccc gcaaggtaac gatatgacca aaggacgtct tacgctggcg aaaggtaaac    1740
caatcggtaa ggaaggttac tactggctga aaatccacgg tgcaaactgt gcgggtgtcg    1800
ataaggtttc gtttcctgag cgcatcaagt tcattgagga aaaccacgag aacatcatgg    1860
cttgcgctaa gtctccactg gagaacactt ggtgggctga gcaagattct ccgttctgct    1920
tccttgcgtt ctgctttgag tacgctgggg tacagcacca cggcctgagc tataactgct    1980
cccttccgct ggcgtttgac gggtcttgct ctggcatcca gcacttctcc gcgatgctcc    2040
gagatgaggt aggtggtcgc gcggttaact tgcttcctag tgaaaccgtt caggacatct    2100
acgggattgt tgctaagaaa gtcaacgaga ttctgcaagc agacgcaatc aatgggaccg    2160
ataacgaagt agttaccgtg accgatgaga acactggtga atctctgag aaagtcaagc    2220 tgggcactaa ggcactggct ggtcaatggc tggcttacgg tgttactcgc agtgtgacta    2280
agcgttcagt catgacgctg gcttacgggt ccaaagagtt cggcttccgt caacaagtgc    2340
tggaagatac cattcagcca gctattgatt ccggcaaggg tctgatgttc actcagccga    2400
atcaggctgc tggatacatg gctaagctga tttgggaatc cgtgagcgtg acggtggtag    2460
ctgcggttga agcaatgaac tggcttaagt ctgctgctaa gctgctggct gctgaggtca    2520
aagataagaa gactggagag attcttcgca agcgttgcgc tgtgcattgg gtaactcctg    2580
atggtttccc tgtgtggcag gaatacaaga agcctattca gacgcgcttg aacctgatgt    2640
tcctcggtca gttccgctta cagcctacca ttaacaccaa caaagatagc gagattgatg    2700
cacacaaaca ggagtctggt atcgctccta actttgtaca cagccaagac ggtagccacc    2760
ttcgtaagac tgtagtgtgg gcacacgaga agtacggaat cgaatctttt gcactgattc    2820
acgactcctt cggtaccatt ccggctgacg ctgcgaacct gttcaaagca gtgcgcgaaa    2880
ctatggttga cacatatgag tcttgtgatg tactggctga tttctacgac cagttcgctg    2940
accagttgca cgagtctcaa ttggacaaaa tgccagcact tccggctaaa ggtaacttga    3000
acctccgtga catcttagag tcggacttcg cgttcgcgta agggcccact agtcggccgt    3060
acgggccctt tcgtctcgcg cgtttcggtg atgacggtga aaacctctga cacatgcagc    3120
tcccggagac ggtcacagct tgtctgtaag cggatgccgg gagcagacaa gcccgtcagg    3180
gcgcgtcagc gggtgttggc gggtgtcggg gctggcttaa ctatgcggca tcagagcaga    3240
ttgtactgag agtgcaccat atgcggtgtg aaataccgca cagatgcgta aggagaaaat    3300
accgcatcag gcggccttaa gggcctcgtg atacgcctat ttttataggt taatgtcatg    3360
ataataatgg tttcttagac gtcaggtggc acttttcggg gaaatgtgcg cggaaccct    3420 atttgtttat ttttctaaat acattcaaat atgtatccgc tcatgagaca ataaccctga    3480
taaatgcttc aataatattg aaaaaggaag agtatgagta ttcaacattt ccgtgtcgcc    3540
```

```
cttattccct tttttgcggc attttgcctt cctgttttttg ctcacccaga aacgctggtg   3600
aaagtaaaag atgctgaaga tcagttgggt gcacgagtgg gttacatcga actggatctc   3660
aacagcggta agatccttga gagttttcgc cccgaagaac gttttccaat gatgagcact   3720
tttaaagttc tgctatgtgg cgcggtatta tcccgtattg acgccgggca agagcaactc   3780
ggtcgccgca tacactattc tcagaatgac ttggttgagt actcaccagt cacagaaaag   3840
catcttacgg atggcatgac agtaagagaa ttatgcagtg ctgccataac catgagtgat   3900
aacactgcgg ccaacttact tctgacaacg atcggaggac cgaaggagct aaccgctttt   3960
ttgcacaaca tggggatca tgtaactcgc cttgatcgtt gggaaccgga gctgaatgaa   4020
gccataccaa acgacgagcg tgacaccacg atgcctgtag caatggcaac aacgttgcgc   4080
aaactattaa ctggcgaact acttactcta gcttcccggc aacaattaat agactggatg   4140
gaggcggata agttgcagg accacttctg cgctcggccc ttccggctgg ctggtttatt   4200
gctgataaat ctggagccgg tgagcgtggg tctcgcggta tcattgcagc actggggcca   4260
gatggtaagc cctcccgtat cgtagttatc tacacgacgg ggagtcaggc aactatggat   4320
gaacgaaata gacagatcgc tgagataggt gcctcactga ttaagcattg gtaactgtca   4380
gaccaagttt actcatatat actttagatt gatttaaaac ttcattttta atttaaaagg   4440
atctaggtga agatcctttt tgataatctc atgaccaaaa tcccttaacg tgagttttcg   4500
ttccactgag cgtcagaccc cgtagaaaag atcaaaggat cttcttgaga tcctttttt   4560 ctgcgcgtaa tctgctgctt gcaaacaaaa aaaccaccgc taccagcggt ggtttgtttg   4620
ccggatcaag agctaccaac tctttttccg aaggtaactg gcttcagcag agcgcagata   4680
ccaaatactg tccttctagt gtagccgtag ttaggccacc acttcaagaa ctctgtagca   4740
ccgcctacat acctcgctct gctaatcctg ttaccagtgg ctgctgccag tggcgataag   4800
tcgtgtctta ccgggttgga ctcaagacga tagttaccgg ataaggcgca gcggtcgggc   4860
tgaacggggg gttcgtgcac acagcccagc ttggagcgaa cgacctacac cgaactgaga   4920
tacctacagc gtgagcattg agaaagcgcc acgcttcccg aagggagaaa ggcggacagg   4980
tatccggtaa gcggcagggt cggaacagga gagcgcacga gggagcttcc agggggaaac   5040
gcctggtatc tttatagtcc tgtcgggttt cgccacctct gacttgagcg tcgatttttg   5100
tgatgctcgt cagggggcg gagcctatgg aaaaacgcca gcaacgcggc cttttacgg   5160 ttcctggcct tttgctggcc ttttgctcac atgttcttc ctgcgttatc ccctgattct   5220
gtggataacc gtattaccgc ctttgagtga gctgataccg ctcgccgcag ccgaacgacc   5280
gagcgcagcg agtcagtgag cgaggaagcg gaagagcgcc caatacgcaa accgcctctc   5340
cccgcgcgtt ggccgattca ttaatgcagc tggcacgaca ggtttcccga ctggaaagcg   5400
ggcagtgagc gcaacgcaat taatgtgagt tagctcactc attaggcacc ccaggcttta   5460
cactttatgc ttccggctcg tatgttgtgt ggaattgtga gcggataaca atttcacaca   5520
ggaaacagct atgaccatga ttacgccaag ctgtaagttt aaacatgatc ttactaacta   5580
actattctca tttaaatttt cagagcttaa aaatggctga atcactcac aacgatggat   5640 acgctaacaa cttggaaatg aaataagctt gcatgcctgc agagcaaaaa atactgctt   5700 ttccttgcaa aattcggtgc tttcttcaaa gagaaacttt tgaagtcggc gcgagcattt   5760
ccttctttga cttctctctt tccgccaaaa agcctagcat ttttattgat aatttgatta   5820
cacacactca gagttcttcg acatgataaa gtgtttcatt ggcactcgcc ctaacagtac   5880
atgacaaggg cggattatta tcgatcgata ttgaagacaa actccaaatg tgtgctcatt   5940
```

```
ttggagcccc gtgtggggca gctgctctca atatattact agggagacga ggaggggac      6000 cttatcgaac gtcgcatgag ccattctttc ttctttatgc actctcttca ctctctcaca      6060
cattaatcga ttcatagact cccatattcc ttgatgaagg tgtgggtttt tagctttttt      6120
tcccgatttg taaaaggaag aggctgacga tgttaggaaa aagagaacgg agccgaaaaa      6180
acatccgtag taagtcttcc ttttaagccg acactttta dacagcattc gccgctagtt       6240
ttgaagttta aattttaaaa aataaaaatt agtttcaatt tttttaatt actaaatagg       6300 caaaagtttt ttcaagaact ctagaaaaac tagcttaatt catgggtact agaaaaattc      6360
ttgttttaaa tttaatattt atcttaagat gtaattacga gaagcttttt tgaaaattct      6420
caattaaaag aatttgccga tttagaataa aagtcttcag aaatgagtaa aagctcaaat      6480
tagaagtttg tttttaaagg aaaaacacga aaaagaaca ctatttatct tttcctcccc       6540
gcgtaaaatt agttgttgtg ataatagtga tccgctgtct atttgcactc ggctcttcac      6600
accgtgcttc ctctcacttg acccaacagg aaaaaaaaac atcacgtctg agacggtgaa      6660
ttgccttatc aagagcgtcg tctctttcac ccagtaacaa aaaaaatttg gtttctttac      6720
tttatattta tgtaggtcac aaaaaaaaag tgatgcagtt ttgtgggtcg gttgtctcca      6780
caccacctcc gcctccagca gcacacaatc atcttcgtgt gttctcgacg attccttgta      6840
tgccgcggtc gtgaatgcac cacattcgac gcgcaactac acaccacact cactttcggt      6900
ggtattacta cacgtcatcg ttgttcgtag tctcccgctc tttcgtcccc actcactcct      6960
cattattccc cttggtgtat tgatttttt taaatggtac accactcctg acgtttctac       7020
cttcttgttt tccgtccatt tagattttat ctggaaattt ttttaaaatt ttaggccaga      7080
gagttctagt tcttgttcta aaagtctagg tcagacatac attttctatt tctcatcaaa      7140 aaaaagttg ataagaaaa ctggttattc agaaagagtg tgtctcgttg aaattgattc        7200
aaaaaaaaat tcccacccct cgcttgtttc tcaaatatg agatcaacgg attttttcct       7260
tctcgattca atttttgct gcgctctgtc tgccaaagtg tgtgtgtccg agcaaaagat       7320
gagagaattt acaaacagaa atgaaaaaaa gttggccaaa taatgaagtt ttatccgaga      7380
ttgatgggaa agatattaat gttctttacg gtttggaggg gagagagaga tagattttcg      7440
catcaaactc cgccttttac atgtctttta gaatctaaaa tagatttttc tcatcatttt      7500
taatagaaaa tcgagaaatt acagtaattt cgcaattttc ttgccaaaaa tacacgaaat      7560
ttgtgggtct cgccacgatc tcggtcttag tggttcattt ggtttaaaag tttataaaat      7620
ttcaaattct agtgtttaat ttccgcataa ttggacctaa aatgggtttt tgtcatcatt      7680
ttcaacaaga aatcgtgaaa atcctgttgt ttcgcaattt tcttttcaaa aatacacgaa      7740
atatatggta atttcccgaa atattgaggg tctcgccacg atttcagtca cagtggccag      7800
gatttatcac gaaaaaagtt cgcctagtct cacatttccg gaaaaccgaa tctaaattag      7860
ttttttgtca tcattttgaa caaaaaatcg agacatccct atagtttcgc aattttcgtc      7920
gcttttctct ccaaaaatga cagtctagaa ttaaaattcg ctggaactgg gaccatgata      7980
tcttttctcc ccgttttca ttttatttt tattacactg gattgactaa aggtcaccac        8040
caccgccagt gtgtgccata tcacacacac acacacacac aatgtcgaga ttttatgtgt      8100
tatccctgct tgatttcgtt ccgttgtctc tctctctcta ttcatctttt gagccgaaaa      8160
gctccagaga atggagcaca caggatcccg gcgcgcgatg tcgtcgggag atggcgccgc      8220
ctgggaagcc gccgagagat atcagggaag atcgtcgat ttctcctcgg atgccacctc       8280
atctctcgag tttctccgcc tgttactccc tgccgaacct gatatttccc                 8330
```

<210> SEQ ID NO 4
<211> LENGTH: 6470
<212> TYPE: DNA
<213> ORGANISM: Artificial Sequence
<220> FEATURE:
<223> OTHER INFORMATION: Description of Artificial Sequence:plasmid DNA

<400> SEQUENCE: 4

| | | | | | | |
|---|---|---|---|---|---|---|
| aagcttgcat | gcctgcaggc | cttggtcgac | tctagacact | tttcagctac | ctagatacat | 60 |
| ggatatcccc | gcctcccaat | ccacccaccc | agggaaaaag | aagggctcgc | cgaaaaatca | 120 |
| aagttatctc | caggctcgcg | catcccaccg | agcggttgac | ttctctccac | cacttttcat | 180 |
| tttaaccctc | ggggtacggg | attggccaaa | ggacccaaag | gtatgtttcg | aatgatacta | 240 |
| acataacata | gaacattttc | aggaggaccc | ttgcttggag | ggtaccgagc | tcagaaaaaa | 300 |
| tgactgctcc | aaagaagaag | cgtaaggtac | cggtaatgaa | cacgattaac | atcgctaaga | 360 |
| acgacttctc | tgacatcgaa | ctggctgcta | tcccgttcaa | cactctggct | gaccattacg | 420 |
| gtgagcgttt | agctcgcgaa | cagttggccc | ttgagcatga | gtcttacgag | atgggtgaag | 480 |
| cacgcttccg | caagatgttt | gagcgtcaac | ttaaagctgg | tgaggttgcg | ataacgctg | 540 |
| ccgccaagcc | tctcatcact | accctactcc | ctaagatgat | tgcacgcatc | aacgactggt | 600 |
| ttgaggaagt | gaaagctaag | cgcggcaagc | gcccgacagc | cttccagttc | ctgcaagaaa | 660 |
| tcaagccgga | agccgtagcg | tacatcacca | ttaagaccac | tctggcttgc | ctaaccagtg | 720 |
| ctgacaatac | aaccgttcag | gctgtagcaa | gcgcaatcgg | tcgggccatt | gaggacgagg | 780 |
| ctcgcttcgg | tcgtatccgt | gaccttgaag | ctaagcactt | caagaaaaac | gttgaggaac | 840 |
| aactcaacaa | gcgcgtaggg | cacgtctaca | gaaagcatt | tatgcaagtt | gtcgaggctg | 900 |
| acatgctctc | taagggtcta | ctcggtggcg | aggcgtggtc | ttcgtggcat | aaggaagact | 960 |
| ctattcatgt | aggagtacgc | tgcatcgaga | tgctcattga | gtcaaccgga | atggttagct | 1020 |
| tacaccgcca | aaatgctggc | gtagtaggtc | aagactctga | gactatcgaa | ctcgcacctg | 1080 |
| aatacgctga | ggctatcgca | acccgtgcag | gtgcgctggc | tggcatctct | ccgatgttcc | 1140 |
| aaccttgcgt | agttcctcct | aagccgtgga | ctggcattac | tggtggtggc | tattgggcta | 1200 |
| acggtcgtcg | tcctctggcg | ctggtgcgta | ctcacagtaa | gaaagcactg | atgcgctacg | 1260 |
| aagacgttta | catgcctgag | gtgtacaaag | cgattaacat | tgcgcaaaac | accgcatgga | 1320 |
| aaatcaacaa | gaaagtccta | gcggtcgcca | acgtaatcac | caagtggaag | cattgtccgg | 1380 |
| tcgaggacat | ccctgcgatt | gagcgtgaag | aactcccgat | gaaaccggaa | gacatcgaca | 1440 |
| tgaatcctga | ggctctcacc | gcgtggaaac | gtgctgccgc | tgctgtgtac | cgcaaggaca | 1500 |
| gggctcgcaa | gtctcgccgt | atcagccttg | agttcatgct | tgagcaagcc | aataagtttg | 1560 |
| ctaaccataa | ggccatctgg | ttcccttaca | acatggactg | gcgcggtcgt | gtttacgccg | 1620 |
| tgtcaatgtt | caacccgcaa | ggtaacgata | tgaccaaagg | actgcttacg | ctggcgaaag | 1680 |
| gtaaaccaat | cggtaaggaa | ggttactact | ggctgaaaat | ccacggtgca | aactgtgcgg | 1740 |
| gtgtcgataa | ggttccgttc | cctgagcgca | tcaagttcat | tgaggaaaac | cacgagaaca | 1800 |
| tcatggcttg | cgctaagtct | ccactggaga | cacttggtg | ggctgagcaa | gattctccgt | 1860 |
| tctgcttcct | tgccgttctg | tttgagtacg | ctggggtaca | gcaccacggc | ctgagctata | 1920 |
| actgctccct | tccgctggcg | tttgacgggt | cttgctctgg | catccagcac | ttctccgcga | 1980 |
| tgctccgaga | tgaggtaggt | ggtcgcgcgg | ttaacttgct | tcctagtgag | accgttcagg | 2040 |
| acatctacgg | gattgttgct | aagaaagtca | acgagattct | acaagcagac | gcaatcaatg | 2100 |

```
ggaccgataa cgaagtagtt accgtgaccg atgagaacac tggtgaaatc tctgagaaag      2160
tcaagctggg cactaaggca ctggctggtc aatggctggc tcacggtgtt actcgcagtg      2220
tgactaagcg ttcagtcatg acgctggctt acgggtccaa agagttcggc ttccgtcaac      2280
aagtgctgga agataccatt cagccagcta ttgattccgg caagggtccg atgttcactc      2340
agccgaatca ggctgctgga tacatggcta agctgatttg gaatctgtg agcgtgacgg       2400 tggtagctgc ggttgaagca atgaactggc ttaagtctgc tgctaagctg ctggctgctg      2460
aggtcaaaga taagaagact ggagagattc ttcgcaagcg ttgcgctgtg cattgggtaa      2520
ctcctgatgg tttccctgtg tggcaggaat acaagaagcc tattcagacg cgcttgaacc      2580
tgatgttcct cggtcagttc cgcttacagc ctaccattaa caccaacaaa gatagcgaga      2640
ttgatgcaca caaacaggag tctggtatcg ctcctaactt tgtacacagc caagacggta      2700
gccaccttcg taagactgta gtgtgggcac acgagaagta cggaatcgaa tcttttgcac      2760
tgattcacga ctccttcggt accattccgg ctgacgctgc gaacctgttc aaagcagtgc      2820
gcgaaactat ggttgacaca tatgagtctt gtgatgtact ggctgatttc tacgaccagt      2880
tcgctgacca gttgcacgag tctcaattgg acaaaatgcc agcacttccg gctaaaggta      2940
acttgaacct ccgtgacatc ttagagtcgg acttcgcgtt cgcgtaagaa ttccaactga      3000
gcgccggtcg ctaccattac caacttgtct ggtgtcaaaa ataataggg ccgctgtcat       3060 cagagtaagt ttaaactgag ttctactaac taacgagtaa tatttaaatt ttcagcatct      3120
cgcgcccgtg cctctgactt ctaagtccaa ttactcttca catccctac atgctctttc       3180 tccctgtgct cccaccccct attttgtta ttatcaaaaa aacttcttct taatttcttt       3240 gtttttttagc ttcttttaag tcacctctaa caatgaaatt gtgtagattc aaaaatagaa     3300
ttaattcgta ataaaaagtc gaaaaaaatt gtgctccctc cccccattaa taataattct      3360
atcccaaaat ctacacaatg ttctgtgtac acttcttatg ttttttttac ttctgataaa      3420 tttttttga aacatcatag aaaaaaccgc acacaaaata ccttatcata tgttacgttt       3480
cagtttatga ccgcaatttt tatttcttcg cacgtctggg cctctcatga cgtcaaatca      3540
tgctcatcgt gaaaaagttt tggagtattt ttggaatttt tcaatcaagt gaaagtttat      3600
gaaattaatt ttcctgcttt tgcttttttgg gggtttcccc tattgtttgt caagagtttc     3660
gaggacggcg ttttttcttgc taaaatcaca agtattgatg agcacgatgc aagaaagatc     3720
ggaagaaggt ttgggtttga ggctcagtgg aaggtgagta gaagttgata atttgaaagt      3780
ggagtagtgt ctatggggtt tttgccttaa atgacagaat acattcccaa tataccaaac      3840
ataactgttt cctactagtc ggccgtacgg gcccttcgt ctcgcgcgtt tcggtgatga       3900
cggtgaaaac ctctgacaca tgcagctccc ggagacggtc acagcttgtc tgtaagcgga      3960
tgccgggagc agacaagccc gtcagggcgc gtcagcgggt gttggcgggt gtcgggctg       4020 gcttaactat gcggcatcag agcagattgt actgagagtg caccatatgc ggtgtgaaat      4080
accgcacaga tgcgtaagga gaaaataccg catcaggcgg ccttaagggc ctcgtgatac      4140
gcctattttt ataggttaat gtcatgataa taatggtttc ttagacgtca ggtggcactt      4200
ttcggggaaa tgtgcgcgga acccctattt gtttattttt ctaaatacat tcaaatatgt      4260
atccgctcat gagacaataa ccctgataaa tgcttcaata atattgaaaa aggaagagta      4320
tgagtattca acatttccgt gtcgccctta ttcccttttt tgcggcattt tgccttcctg      4380 ttttgctca cccagaaacg ctggtgaaag taaaagatgc tgaagatcag ttgggtgcac       4440
gagtgggtta catcgaactg gatctcaaca gcggtaagat ccttgagagt tttcgccccg      4500
```

```
aagaacgttt tccaatgatg agcacttttta aagttctgct atgtggcgcg gtattatccc    4560
gtattgacgc cgggcaagag caactcggtc gccgcataca ctattctcag aatgacttgg    4620
ttgagtactc accagtcaca gaaaagcatc ttacgcatgg catgacagta agagaattat    4680
gcagtgctgc cataaccatg agtgataaca ctgcggccaa cttacttctg acaacgatcg    4740
gaggaccgaa ggagctaacc gcttttttgc acaacatggg ggatcatgta actcgccttg    4800
atcgttggga accggagctg aatgaagcca taccaaacga cgagcgtgac accacgatgc    4860
ctgtagcaat ggcaacaacg ttgcgcaaac tattaactgg cgaactactt actctagctt    4920
cccggcaaca attaatagac tggatggagg cggataaagt tgcaggacca cttctgcgct    4980
cggcccttcc ggctggctgg tttattgctg ataaatctgg agccggtgag cgtgggtctc    5040
gcggtatcat tgcagcactg gggccagatg gtaagccctc ccgtatcgta gttatctaca    5100
cgacggggag tcaggcaact atggatgaac gaaatagaca gatcgctgag ataggtgcct    5160
cactgattaa gcattggtaa ctgtcagacc aagtttactc atatatactt tagattgatt    5220
taaaacttca ttttttaatttt aaaaggatct aggtgaagat cctttttgat aatctcatga    5280
ccaaaatccc ttaacgtgag ttttcgttcc actgagcgtc agaccccgta gaaaagatca    5340
aaggatcttc ttgagatcct ttttttctgc gcgtaatctg ctgcttgcaa acaaaaaaac    5400
caccgctacc agcggtggtt tgtttgccgg atcaagagct accaactctt tttccgaagg    5460
taactggctt cagcagagcg cagataccaa atactgtcct tctagtgtag ccgtagttag    5520
gccaccactt caagaactct gtagcaccgc ctacatacct cgctctgcta atcctgttac    5580
cagtggctgc tgccagtggc gataagtcgt gtcttaccgg gttggactca agacgatagt    5640
taccggataa ggcgcagcgg tcgggctgaa cggggggttc gtgcacacag cccagcttgg    5700
agcgaacgac ctacaccgaa ctgagatacc tacagcgtga gcattgagaa agcgccacgc    5760
ttcccgaagg gagaaaggcg gacaggtatc cggtaagcgg cagggtcgga acaggagagc    5820
gcacgaggga gcttccaggg ggaaacgcct ggtatcttta tagtcctgtc gggtttcgcc    5880
acctctgact tgagcgtcga tttttgtgat gctcgtcagg gggcggagc ctatggaaaa    5940 acgccagcaa cgcggccttt ttacggttcc tggccttttg ctggccttttt gctcacatgt    6000 tctttcctgc gttatcccct gattctgtgg ataaccgtat taccgccttt gagtgagctg    6060
ataccgctcg ccgcagccga acgaccgagc gcagcgagtc agtgagcgag gaagcggaag    6120
agcgcccaat acgcaaaccg cctctccccg cgcgttggcc gattcattaa tgcagctggc    6180
acgacaggtt tcccgactgg aaagcgggca gtgagcgcaa cgcaattaat gtgagttagc    6240
tcactcatta ggcaccccag gctttacact ttatgcttcc ggctcgtatg ttgtgtggaa    6300
ttgtgagcgg ataacaattt cacacaggaa acagctatga ccatgattac gccaagctgt    6360
aagtttaaac atgatcttac taactaacta ttctcattta aattttcaga gcttaaaaat    6420
ggctgaaatc actcacaacg atggatacgc taacaacttg gaaatgaaat                6470
```

<210> SEQ ID NO 5
<211> LENGTH: 4689
<212> TYPE: DNA
<213> ORGANISM: Artificial Sequence
<220> FEATURE:
<223> OTHER INFORMATION: Description of Artificial Sequence:plasmid DNA

<400> SEQUENCE: 5

```
aagcttgcat gcctgcaggc cttggtcgac tctagacact tttcagctac ctagatacat      60
ggatatcccc gcctcccaat ccacccaccc agggaaaaag aagggctcgc cgaaaaatca    120
```

-continued

```
aagttatctc caggctcgcg catcccaccg agcggttgac ttctctccac cactttcat      180
tttaaccctc ggggtacggg attggccaaa ggacccaaag gtatgtttcg aatgatacta     240
acataacata gaacatttc aggaggaccc ttgcttggag ggtaccgagc tcccgggatt      300
aatacgactc actataccgg tagaaaaaat gagtaaagga gaagaacttt tcactggagt     360
tgtcccaatt cttgttgaat tagatggtga tgttaatggg cacaaatttt ctgtcagtgg     420
agagggtgaa ggtgatgcaa catacggaaa acttacccct aaatttattt gcactactgg    480
aaaactacct gttccatggg taagtttaaa catatatata ctaactaacc ctgattattt     540
aaattttcag ccaacacttg tcactacttt ctgttatggt gttcaatgct tctcgagata    600
cccagatcat atgaaacggc atgactttt caagagtgcc atgcccgaag gttatgtaca     660
ggaaagaact atatttttca aagatgacgg gaactacaag acacgtaagt ttaaacagtt    720
cggtactaac taaccataca tatttaaatt ttcaggtgct gaagtcaagt ttgaaggtga    780
taccctgtt aatagaatcg agttaaaagg tattgatttt aaagaagatg gaacattct      840
tggacacaaa ttggaataca actataactc acacaatgta tacatcatgg cagacaaaca    900
aaagaatgga atcaaagttg taagtttaaa catgatttta ctaactaact aatctgattt    960
aaattttcag aacttcaaaa ttagacacaa cattgaagat ggaagcgttc aactagcaga   1020
ccattatcaa caaaatactc caattggcga tggccctgtc cttttaccag acaaccatta   1080
cctgtccaca caatctgccc tttcgaaaga tcccaacgaa aagagagacc acatggtcct   1140
tcttgagttt gtaacagctg ctgggattac acatggcatg gatgaactat acaaatagca   1200
ttcgtagaat tccaactgag cgccggtcgc taccattacc aacttgtctg gtgtcaaaaa   1260
taataggggc cgctgtcatc agagtaagtt taaactgagt tctactaact aacgagtaat   1320
atttaaattt tcagcatctc gcgcccgtgc ctctgacttc taagtccaat tactcttcaa   1380
catccctaca tgctctttct ccctgtgctc ccacccccta ttttgttat tatcaaaaaa    1440
acttcttctt aatttctttg tttttagct tcttaagt cacctctaac aatgaaattg      1500
tgtagattca aaaatagaat taattcgtaa taaaagtcg aaaaaaattg tgctccctcc    1560
ccccattaat aataattcta tcccaaaatc tacacaatgt tctgtgtaca cttcttatgt   1620
ttttttact tctgataaat ttttttgaa acatcataga aaaaccgca cacaaaatac      1680
cttatcatat gttacgtttc agtttatgac cgcaatttt atttcttcgc acgtctgggc   1740
ctctcatgac gtcaaatcat gctcatcgtg aaaaagtttt ggagtatttt tggaatttt    1800
caatcaagtg aaagtttatg aaattaattt tcctgctttt gcttttggg ggtttcccct   1860
attgtttgtc aagagtttcg aggacggcgt ttttcttgct aaaatcacaa gtattgatga   1920
gcacgatgca agaaagatcg gaagaaggtt tgggtttgag gctcagtgga aggtgagtag   1980
aagttgataa tttgaaagtg gagtagtgtc tatggggttt ttgccttaaa tgacagaata   2040
cattcccaat ataccaaaca taactgtttc ctactagtcg gccgtacggg cccttcgtc    2100
tcgcgcgttt cggtgatgac ggtgaaaacc tctgacacat gcagctcccg gagacggtca   2160
cagcttgtct gtaagcggat gccggagca gacaagcccg tcaggcgcg tcagcgggtg     2220
ttggcgggtg tcgggctgg cttaactatg cggcatcaga gcagattgta ctgagagtgc    2280
accatatgcg gtgtgaaata ccgcacagat gcgtaaggag aaaataccgc atcaggcggc   2340
cttaagggcc tcgtgatacg cctatttta taggttaatg tcatgataat aatggtttct    2400
tagacgtcag gtggcacttt tcggggaaat gtgcgcggaa cccctatttg tttatttttc   2460
taaatacatt caaatatgta tccgctcatg agacaataac cctgataaat gcttcaataa   2520
```

```
tattgaaaaa ggaagagtat gagtattcaa catttccgtg tcgcccttat tccctttttt    2580
gcggcatttt gccttcctgt ttttgctcac ccagaaacgc tggtgaaagt aaaagatgct    2640
gaagatcagt tgggtgcacg agtgggttac atcgaactgg atctcaacag cggtaagatc    2700
cttgagagtt ttcgcccga agaacgtttt ccaatgatga gcacttttaa agttctgcta    2760
tgtggcgcgg tattatcccg tattgacgcc gggcaagagc aactcggtcg ccgcatacac    2820
tattctcaga atgacttggt tgagtactca ccagtcacag aaaagcatct tacggatggc    2880
atgacagtaa gagaattatg cagtgctgcc ataaccatga gtgataacac tgcggccaac    2940
ttacttctga caacgatcgg aggaccgaag gagctaaccg cttttttgca acatgggg      3000 gatcatgtaa ctcgccttga tcgttgggaa ccggagctga atgaagccat accaaacgac    3060
gagcgtgaca ccacgatgcc tgtagcaatg gcaacaacgt tgcgcaaact attaactggc    3120
gaactactta ctctagcttc ccggcaacaa ttaatagact ggatggaggc ggataaagtt    3180
gcaggaccac ttctgcgctc ggcccttccg gctggctggt ttattgctga taaatctgga    3240
gccggtgagc gtgggtctcg cggtatcatt gcagcactgg ggccagatgg taagccctcc    3300
cgtatcgtag ttatctacac gacggggagt caggcaacta tggatgaacg aaatagacag    3360
atcgctgaga taggtgcctc actgattaag cattggtaac tgtcagacca agtttactca    3420
tatatacttt agattgattt aaaacttcat ttttaattta aaaggatcta ggtgaagatc    3480
ctttttgata atctcatgac caaaatccct taacgtgagt tttcgttcca ctgagcgtca    3540
gaccccgtag aaaagatcaa aggatcttct tgagatcctt ttttctgcg cgtaatctgc     3600 tgcttgcaaa caaaaaaacc accgctacca gcggtggttt gtttgccgga tcaagagcta    3660
ccaactcttt ttccgaaggt aactggcttc agcagagcgc agataccaaa tactgtcctt    3720
ctagtgtagc cgtagttagg ccaccacttc aagaactctg tagcaccgcc tacatacctc    3780
gctctgctaa tcctgttacc agtggctgct gccagtggcg ataagtcgtg tcttaccggg    3840
ttggactcaa gacgatagtt accggataag gcgcagcggt cgggctgaac ggggggttcg    3900
tgcacacagc ccagcttgga gcgaacgacc tacaccgaac tgagatacct acagcgtgag    3960
cattgagaaa gcgccacgct tcccgaaggg agaaaggcgg acaggtatcc ggtaagcggc    4020
agggtcggaa caggagagcg cacgagggag cttccagggg gaaacgcctg gtatctttat    4080
agtcctgtcg ggtttcgcca cctctgactt gagcgtcgat ttttgtgatg ctcgtcaggg    4140
gggcggagcc tatggaaaaa cgccagcaac gcggccttt tacggttcct ggccttttgc     4200
tggccttttg ctcacatgtt ctttcctgcg ttatcccctg attctgtgga taaccgtatt    4260
accgcctttg agtgagctga taccgctcgc cgcagccgaa cgaccgagcg cagcgagtca    4320
gtgagcgagg aagcggaaga gcgcccaata cgcaaaccgc ctctccccgc gcgttggccg    4380
attcattaat gcagctggca cgacaggttt cccgactgga agcgggcag tgagcgcaac     4440 gcaattaatg tgagttagct cactcattag gcaccccagg ctttacactt tatgcttccg    4500
gctcgtatgt tgtgtggaat tgtgagcgga taacaatttc acacaggaaa cagctatgac    4560
catgattacg ccaagctgta agtttaaaca tgatcttact aactaactat tctcatttaa    4620
attttcagag cttaaaaatg gctgaaatca ctcacaacga tggatacgct aacaacttgg    4680
aaatgaaat                                                            4689
```

<210> SEQ ID NO 6
<211> LENGTH: 5175
<212> TYPE: DNA
<213> ORGANISM: Artificial Sequence
<220> FEATURE:
<223> OTHER INFORMATION: Description of Artificial Sequence:plasmid DNA

<400> SEQUENCE: 6

```
gatcccggcg cgcgatgtcg tcgggagatg gcgccgcctg ggaagccgcc gagagatatc      60
agggaagatc gtctgatttc tcctcggatg ccacctcatc tctcgagttt ctccgcctgt     120
tactccctgc cgaacctgat atttcccgtt gtcgtaaaga gatgttttta ttttacttta     180
caccgggtcc tctctctctg ccagcacagc tcagtgttgg ctgtgtgctc gggctcctgc     240
caccggcggc ctcatcttct tcttcttctt ctctcctgct ctcgcttatc acttcttcat     300
tcattcttat tccttttcat catcaaacta gcatttctta ctttatttat tttttttcaat    360 tttcaatttt cagataaaac caaactactt gggttacagc cgtcaacaga tccccgggat     420
tggccaaagg acccaaaggt atgtttcgaa tgatactaac ataacataga acattttcag     480 gaggacccctt gcttggaggg taccggtaga aaaaatgagt aaaggagaag aacttttcac    540
tggagttgtc ccaattcttg ttgaattaga tggtgatgtt aatgggcaca aattttctgt     600
cagtggagag ggtgaaggtg atgcaacata cggaaaactt acccttaaat ttatttgcac     660
tactggaaaa ctacctgttc catgggtaag tttaaacata tatatactaa ctaaccctga     720
ttatttaaat tttcagccaa cacttgtcac tactttctgt tatggtgttc aatgcttctc     780 gagatacccca gatcatatga aacggcatga cttttttcaag agtgccatgc ccgaaggtta    840
tgtacaggaa agaactatat ttttcaaaga tgacgggaac tacaagacac gtaagtttaa     900
acagttcggt actaactaac catacatatt taaatttcaa ggtgctgaag tcaagtttga     960
aggtgatacc cttgttaata gaatcgagtt aaaaggtatt gattttaaag aagatggaaa    1020
cattcttgga cacaaattgg aatacaacta taactcacac aatgtataca tcatggcaga    1080
caaacaaaag aatggaatca aagttgtaag tttaaacttg gacttactaa ctaacggatt    1140
atatttaaat tttcagaact tcaaaattag acacaacatt gaagatggaa gcgttcaact    1200
agcagaccat tatcaacaaa atactccaat tggcgatggc cctgtccttt taccagacaa    1260
ccattacctg tccacacaat ctgcccttc gaaagatccc aacgaaaaga gagaccacat    1320
ggtccttctt gagtttgtaa cagctgctgg gattacacat ggcatggatg aactatacaa    1380
atagcattcg tagaattcca actgagcgcc ggtcgctacc attaccaact tgtctggtgt    1440
caaaaataat aggggccgct gtcatcagag taagtttaaa ctgagttcta ctaactaacg    1500
agtaatattt aaattttcag catctcgcgc ccgtgcctct gacttctaag tccaattact    1560
cttcaacatc cctacatgct ctttctccct gtgctcccac cccctatttt tgttattatc    1620
aaaaaaactt cttcttaatt tctttgtttt ttagcttctt ttaagtcacc tctaacaatg    1680
aaattgtgta gattcaaaaa tagaattaat tcgtaataaa aagtcgaaaa aaattgtgct    1740 ccctccccc attaataata attctatccc aaaatctaca caatgttctg tgtacacttc    1800
ttatgttttt tttacttctg ataaattttt tttgaaacat catagaaaaa accgcacaca    1860 aaataccta tcatatgtta cgtttcagtt tatgaccgca attttttattt cttcgcacgt    1920 ctgggcctct catgacgtca aatcatgctc atcgtgaaaa agtttggag tattttttgga    1980 attttttcaat caagtgaaag tttatgaaat taattttcct gcttttgctt tttggggtt    2040 tccctattg tttgtcaaga gtttcgagga cggcgttttt cttgctaaaa tcacaagtat    2100
tgatgagcac gatgcaagaa agatcggaag aaggtttggg tttgaggctc agtggaaggt    2160
gagtagaagt tgataattg aaagtggagt agtgtctatg gggttttgc cttaaatgac    2220 agaatacatt cccaatatac caaacataac tgtttcctac tagtcggccg tacgggcccg    2280
```

```
gtacccagct tttgttccct ttagtgaggg ttaattgcgc gcttggcgta atcatggtca   2340
tagctgtttc ctgtgtgaaa ttgttatccg ctcacaattc cacacaacat acgagccgga   2400
agcataaagt gtaaagcctg gggtgcctaa tgagtgagct aactcacatt aattgcgttg   2460
cgctcactgc ccgctttcca gtcgggaaac ctgtcgtgcc agctgcatta atgaatcggc   2520
caacgcgcgg ggagaggcgg tttgcgtatt gggcgctctt ccgcttcctc gctcactgac   2580
tcgctgcgct cggtcgttcg gctgcggcga gcggtatcag ctcactcaaa ggcggtaata   2640
cggttatcca cagaatcagg ggataacgca ggaaagaaca tgtgagcaaa aggccagcaa   2700
aaggccagga accgtaaaaa ggccgcgttg ctggcgtttt tccataggct ccgcccccct   2760
gacgagcatc acaaaaatcg acgctcaagt cagaggtggc gaaacccgac aggactataa   2820
agataccagg cgtttccccc tggaagctcc ctcgtgcgct ctcctgttcc gaccctgccg   2880
cttaccggat acctgtccgc ctttctccct tcgggaagcg tggcgctttc tcatagctca   2940
cgctgtaggt atctcagttc ggtgtaggtc gttcgctcca agctgggctg tgtgcacgaa   3000
ccccccgttc agcccgaccg ctgcgcctta tccggtaact atcgtcttga gtccaacccg   3060
gtaagacacg acttatcgcc actggcagca gccactggta acaggattag cagagcgagg   3120
tatgtaggcg gtgctacaga gttcttgaag tggtggccta actacggcta cactagaagg   3180
acagtatttg gtatctgcgc tctgctgaag ccagttacct tcggaaaaag agttggtagc   3240
tcttgatccg gcaaacaaac caccgctggt agcggtggtt ttttttgtttg caagcagcag   3300 attacgcgca gaaaaaaagg atctcaagaa gatcctttga tcttttctac ggggtctgac   3360
gctcagtgga acgaaaactc acgttaaggg attttggtca tgagattatc aaaaaggatc   3420
ttcacctaga tccttttaaa ttaaaaatga agttttaaat caatctaaag tatatatgag   3480
taaacttggt ctgacagtta ccaatgctta atcagtgagg cacctatctc agcgatctgt   3540
ctatttcgtt catccatagt tgcctgactc cccgtcgtgt agataactac gatacgggag   3600
ggcttaccat ctggccccag tgctgcaatg ataccgcgag acccacgctc accggctcca   3660
gatttatcag caataaacca gccagccgga agggccgagc gcagaagtgg tcctgcaact   3720
ttatccgcct ccatccagtc tattaattgt tgccgggaag ctagagtaag tagttcgcca   3780
gttaatagtt tgcgcaacgt tgttgccatt gctacaggca tcgtggtgtc acgctcgtcg   3840
tttggtatgg cttcattcag ctccggttcc caacgatcaa ggcgagttac atgatccccc   3900
atgttgtgca aaaaagcggt tagctccttc ggtcctccga tcgttgtcag aagtaagttg   3960
gccgcagtgt tatcactcat ggttatggca gcactgcata attctcttac tgtcatgcca   4020
tccgtaagat gcttttctgt gactggtgag tactcaacca agtcattctg agaatagtgt   4080
atgcggcgac cgagttgctc ttgcccggcg tcaatacggg ataataccgc gccacatagc   4140
agaactttaa aagtgctcat cattggaaaa cgttcttcgg ggcgaaaact ctcaaggatc   4200
ttaccgctgt tgagatccag ttcgatgtaa cccactcgtg cacccaactg atcttcagca   4260
tcttttactt tcaccagcgt ttctgggtga gcaaaaacag gaaggcaaaa tgccgcaaaa   4320
aagggaataa gggcgacacg gaaatgttga atactcatac tcttcctttt tcaatattat   4380
tgaagcattt atcagggtta ttgtctcatg agcggataca tatttgaatg tatttagaaa   4440
aataaacaaa taggggttcc gcgcacattt ccccgaaaag tgccacctaa attgtaagcg   4500
ttaatatttt gttaaaattc gcgttaaatt tttgttaaat cagctcattt tttaaccaat   4560
aggccgaaat cggcaaaatc ccttataaat caaaagaata gaccgagata gggttgagtg   4620
ttgttccagt ttggaacaag agtccactat taaagaacgt ggactccaac gtcaaagggc   4680
```

-continued

```
gaaaaaccgt ctatcagggc gatggcccac tacgtgaacc atcaccctaa tcaagttttt    4740
tggggtcgag gtgccgtaaa gcactaaatc ggaaccctaa agggagcccc cgatttagag    4800
cttgacgggg aaagccggcg aacgtggcga gaaggaagg gaagaaagcg aaaggagcgg    4860
gcgctagggc gctggcaagt gtagcggtca cgctgcgcgt aaccaccaca cccgccgcgc    4920
ttaatgcgcc gctacaggc gcgtcccatt cgccattcag gctgcgcaac tgttgggaag    4980
ggcgatcggt gcgggcctct tcgctattac gccagctggc gaaaggggga tgtgctgcaa    5040
ggcgattaag ttgggtaacg ccagggtttt cccagtcacg acgttgtaaa acgacggcca    5100
gtgagcgcgc gtaatacgac tcactatagg gcgaattgga gctccaccgc ggtggcggcc    5160
gctctagaac tagtg    5175
```

<210> SEQ ID NO 7
<211> LENGTH: 12482
<212> TYPE: DNA
<213> ORGANISM: Artificial Sequence
<220> FEATURE:
<223> OTHER INFORMATION: Description of Artificial Sequence:plasmid DNA

<400> SEQUENCE: 7

```
gatcctccaa aatcgtcttc cgctctgaaa acgaaagtg gacctttgac atccgaaaaa      60
atgggcgaaa aatgaaatt gagcttttg gtcgaaaaaa atgttttta gaatgctgag     120 aacacgttaa acacgaagat catatttatt ttgagacccg gatgctctga aaatgtctga    180
catagattta aaaagcata tatatatttt tcattttcaa cgtgaaagtt ttgtgcaact    240
ttatagaatc tcctattggc acattgtttt ttatttaact gaggcagttt ttgaacacct    300
ttttgaaact ttgaatctct ttgaagtata ctgtcgaaaa gactgacttg agcgttcgaa    360
atgccagaag aaaactatat ttgaatctcg cgctaaattg agaaatgcaa ccgcgctcca    420
ctggacaatt ggaaaaaaaa tttattcgga ggcgacaacg gtattttcga aattgatttt    480
ctgtgtattt tctcattttt tataaattct tctttgattt atcgttcgtt tgtgagaaat    540
ttaattgtat tcaaactttt ttatagtaag ataccggtgg taccgctagc cgtacgaacc    600
cgggattggc caaaggaccc aaaggtatgt ttcgaatgat actaacataa catagaacat    660
tttcaggagg acccttgctt ggagggtacc ggatgactgc tccaaagaag aagcgtaagc    720
tcatgaacac gattaacatc gctaagaacg acttctctga catcgaactg gctgctatcc    780
cgttcaacac tctggctgac cattacggtg agcgtttagc tcgcgaacag ttggcccttg    840
agcatgagtc ttacgagatg ggtgaagcac gcttccgcaa gatgtttgag cgtcaactta    900
aagctggtga ggttgcggat aacgctgccg ccaagcctct catcactacc ctactcccta    960
agatgattgc acgcatcaac gactggtttg aggaagtgaa agctaagcgc ggcaagcgcc   1020
cgacagccct tccagttcctg caagaaatca agccggaagc cgtagcgtac atcaccatta   1080
agaccactct ggcttgccta accagtgctg acaatacaac cgttcaggct gtagcaagcg   1140
caatcggtcg ggccattgag gacgaggctc gcttcggtcg tatccgtgac cttgaagcta   1200
agcacttcaa gaaaaacgtt gaggaacaac tcaacaagcg cgtagggcac gtctacaaga   1260
aagcatttat gcaagttgtc gaggctgaca tgctctctaa gggtctactc ggtggcgagg   1320
cgtggtcttc gtggcataag gaagactcta ttcatgtagg agtacgctgc atcgagatgc   1380
tcattgagtc aaccggaatg gttagcttac accgccaaaa tgctggcgta gtaggtcaag   1440
actctgagac tatcgaactc gcacctgaat acgctgaggc tatcgcaacc cgtgcaggtg   1500
cgctggctgg catctctccg atgttccaac cttgcgtagt tcctcctaag ccgtggactg   1560
```

```
gcattactgg tggtggctat tgggctaacg gtcgtcgtcc tctggcgctg gtgcgtactc    1620
acagtaagaa agcactgatg cgctacgaag acgtttacat gcctgaggtg tacaaagcga    1680
ttaacattgc gcaaaacacc gcatggaaaa tcaacaagaa agtcctagcg gtcgccaacg    1740
taatcaccaa gtggaagcat tgtccggtcg aggacatccc tgcgattgag cgtgaagaac    1800
tcccgatgaa accggaagac atcgacatga atcctgaggc tctcaccgcg tggaaacgtg    1860
ctgccgctgc tgtgtaccgc aagacaaggc tcgcaagtct cgccgtatca gccttgagtt    1920
catgcttgag caagccaata agtttgctaa ccataaggcc atctggttcc cttacaacat    1980
ggactggcgc ggttcgtgtt tacgctgtgt caatgttcaa cccgcaaggt aacgatatga    2040
ccaaaggacg tcttacgctg gcgaaaggta accaatcgg taaggaaggt tactactggc     2100
tgaaaatcca cggtgcaaac tgtgcgggtg tcgataaggt ttcgtttcct gagcgcatca    2160
agttcattga ggaaaaccac gagaacatca tggcttgcgc taagtctcca ctggagaaca    2220
cttggtgggc tgagcaagat tctccgttct gcttccttgc gttctgcttt gagtacgctg    2280
gggtacagca ccacggcctg agctataact gctcccttcc gctggcgttt gacgggtctt    2340
gctctggcat ccagcacttc tccgcgatgc tccgagatga ggtaggtggt cgcgcggtta    2400
acttgcttcc tagtgaaacc gttcaggaca tctacgggat tgttgctaag aaagtcaacg    2460
agattctgca agcagacgca atcaatggga ccgataacga agtagttacc gtgaccgatg    2520
agaacactgg tgaaatctct gagaaagtca agctgggcac taaggcactg gctggtcaat    2580
ggctggctta cggtgttact cgcagtgtga ctaagcgttc agtcatgacg ctggcttacg    2640
ggtccaaaga gttcggcttc cgtcaacaag tgctggaaga taccattcag ccagctattg    2700
attccggcaa gggtctgatg ttcactcagc cgaatcaggc tgctggatac atggctaagc    2760
tgatttggga atccgtgagc gtgacggtgg tagctgcggt tgaagcaatg aactggctta    2820
agtctgctgc taagctgctg gctgctgagg tcaaagataa gaagactgga gagattcttc    2880
gcaagcgttg cgctgtgcat tgggtaactc ctgatggttt ccctgtgtgg caggaataca    2940
agaagcctat tcagacgcgc ttgaacctga tgttcctcgg tcagttccgc ttacagccta    3000
ccattaacac caacaaagat agcgagattg atgcacacaa acaggagtct ggtatcgctc    3060
ctaactttgt acacagccaa gacggtagcc accttcgtaa gactgtagtg tgggcacacg    3120
agaagtacgg aatcgaatct tttgcactga ttcacgactc cttcggtacc attccggctg    3180
acgctgcgaa cctgttcaaa gcagtgcgcg aaactatggt tgacacatat gagtcttgtg    3240
atgtactggc tgatttctac gaccagttcg ctgaccagtt gcacgagtct caattggaca    3300
aaatgccagc acttccggct aaaggtaact tgaacctccg tgacatctta gagtcggact    3360
tcgcgttcgc gtaagggccc tcgtcgagtc ggtcacaatc acctgaaact ccaaaggcag    3420
ccagtgagga acgtgaagaa gagaaaaaag agtcatctga acaggtttga ttttctttct    3480
ggtcaaaaag atgaaattat tgattttcag ccagatactc ccaaaactag cagcgagaag    3540
tctgcaagtc gttcacagtc gcccagaaa tcgcggaag tgagccaaga ggtatgtttt      3600
tcaaaaatca ataactgatc ataatttta ttgtttggtg aatttaagaa aataatattc      3660
gaaaattcct ctgaattatc aagattgcag tattaatttc gagaaaaatt gagatattca    3720
tagagctatt gtaaattttc ttgatttcag actgaaactt cggaaaatca agagaaaatc    3780
aaagaaaagg atgacgggga tgatcagcct ggcacaccga acagctatag aagccgggaa    3840
acttcaccag ctccaaaaag gtccaaggag accaggtttg tcaaaagctt cctgcgatta    3900
attctcattt caattttca gagaatcaga gtctcctgaa aaatcccgg ttcgttcaag       3960
```

```
atctcccaga aggtcttcag cacgttcccc gtcacgatct cctagacggc gccgagaaag    4020
aagctcagaa agaaagcaat ccgaagagcc agcaccgcta ccagagaaaa agaagaaaga    4080
gccgctggat attctacgaa caagaaccgg aggagcatat attccacccg ccaaacttcg    4140
acttatgcaa caacagatta gtgataagca aagtgaacag tatcagagaa tgaattggga    4200
aagaatgaag aaaaagattc acggattggt taacagagtc aacgcgaaga atcttgttca    4260
aattgtcaga gaacttcttc aagagaatgt gattcgttca aagtgagtga gaaaatcgaa    4320
ggaaaaggaa agaattaatt taattttttca ggggacttct ctgccgtgac attattcaag    4380
ctcaggcttt ctcaccagga ttctctaacg tctatgcagc tttggcggca gttatcaact    4440
cgaaattccc tcatgtcggt gaacttcttc tccgtcgtct gattgtacag ttcaaaagaa    4500
gtttccgtag aaatgacaga ggcgtcacgg tgaacgtgat caaattcatc gcacatttga    4560
ttaatcaaca agttgctcac gaagttcttg cgctggaaat catgattctg atgcttgaag    4620
aaccaactga tgattcagtt gaagtcgcca ttgcgttcct gaaagagtgt ggagcaaagc    4680
ttctggagat tgctccagca gctcttaaca gtgtctacga ccgtcttcgt gcaattctca    4740
tggaaactga aagatcggaa aatgcactgg atcgacgtat tcagtatatg attgagactg    4800
caatgcagat tcgaaggac aaatttgcgg taaggtagaa tatataaata gtttattaga    4860
aaaaaataaa ttagaataat ttaaattcct actagccaat caggcgacct ttttgcgcat    4920
agttctatta ttgaaaaatt tggagaattt ctcatattct cgctcggaaa tctggaattc    4980
gacgagatct tctggcttct gtgcagctgc atcgctttgt gctccctttc tcgcttgtct    5040
tctgtgtaca ccaagaacct tgttgagttc atcaactgaa tctgtgactg gcttgttgct    5100
cactggatgc actagacgac tgattctcga gaaatcagat tgagttgcga ttagggtgac    5160
ctagaaattg gaataatac gaacttttga aaatattcag gaggattaaa aaaattattc    5220
tcgacaatcc tacaaattta cttattgcac catgttgctc caacattttt cattaaaagt    5280
taatgaaaaa atgtagaaaa tcggaaattg gcaattttca gaccattttt aagcattttc    5340
aaaaaaaaat tgcagctgaa ataaatgtca ttttcagata aatcgagcga ttttctgttg    5400
tctgacacta gttttagtt ttaaaaaatg ttggaagaac atggtgcaat aggtaatttc    5460
atagaatttc catgtgtttt ttttcaatta accaattatc caaatcttcc aaactcacat    5520
tttgcggagc tgggctatca agaatctgct gcagtttat aagacgagca tctctgatat    5580
cactgaaaat taattttaa tcaaaacttg aatatcaact aaaccacctt attaactttc    5640
tcgatcttct gtcgttcggt acgatgacgg tgaagaagcc aattgtagta gttgatttgg    5700
ttcaagtcct ttcggtgttg tacgtcagtg tcctgcaatg ctatttagtt ataacttagg    5760
cctaagattc aatttaatga agtgattaaa tttgttctct gaacctctta agatgatctt    5820
ttggattaga aacatataag acaggtttac ctatctatta aaaaacagat caaaatagat    5880
acgaccaaat cggataatcc atgcctacct ggcatctagg aacgtgttct tagaagattt    5940
cttacgtaat cgtatgaaga aataacaatt tgatcgttgg ccagcaaaaa tagggtttta    6000
agtgggatag tgttttttatt agctaaccgg aaaatttat agtttttttt tgcaagaaac    6060
cactgaaaac ccctaattg tatacatttt ttggagcagc ttctggtctt tttgagcaat    6120
aaaattcgat aaaacagaat ttaagtgtaa attgttcaca tttagtttct atttatcaa    6180 attttgttgc tcaaaaacat tcgaagctgc tctaaaaaaa tgcattaaaa aaggggtttt    6240
cagtggtttt tcacattaaa aaagctaatt ttaactaaaa atccatcata tttccaactt    6300
tgtcacaaca ataaaatgct ggtcaaaatg tgttcgaaaa aatgtttttt tttttaattt    6360
```

```
ttataattta aaaatagttt tctttcgctg ggacacatac attttgggc gtaaattttc    6420
agttcaaatt tccatttta caaccataat cataaagcta cgtctgatct ctctcgcact    6480
tacctgcgcc tgattcgaaa gaacaaccgt agccaaaaga acaagaagaa caagcacgta    6540
gttgtggtag tggacgttca tcacgcaata ctgaccaatg gtcgtggggt ctcactttcc    6600
gtactattga gagaggggag actgaagatg gcaattgagg acagtgtctt cgacgcacgc    6660
atgcatccat aagcataatc caggagggat ggagagaaaa atcttgtttc taagcccctc    6720
cctttgtaat acatacacat atctaatacc gaagaatggc taattgaatg gacgtcagct    6780
gttgctgtag ttgccaaggc atcatcgatg aaataactga agaaagaat taaataatta    6840
ttgcaggcgt atccggcggt cattgaagac ttggacttga ttgaggagga ggatcagatc    6900
atccatacac ttaatttgga ggatgcggtt gatccggaaa atgggcttag taagtgactg    6960
accacacgcg gggggcatta atttaataaa ttgaattcca tttcagatgt gttcaaacta    7020
gatccagaat tcgaaaagaa cgaggaggtt tatgaggaga tccgtaagga aatcattgga    7080
aacgccgata tttcggatga ggatggtggc gacgagttgg atgatgaaga agagggtagt    7140
gatgtggaag aggctccgaa gaagactaca gagattattg ataatactga tcagaattga    7200
ctgctttcag aaggtattca ttttgagttt tgggccggca aatctgtaag ttgccggttg    7260
ccgaaaattt gctgaatttg ccggaaaaaa aaattccgga atttatttaa aaacttttg    7320
taaaaattaa attaaatttg caacttttca gagaagtcta cctgacaatg caatcatctt    7380
tggactacca agaagctgct cacaaattgc tgaaaatgaa gattccagac agcatgcagg    7440
tcagcgatgt tgcaaagaaa aattttcgac caaaaaacc aaccaatcat aaatttaaa    7500
aaaaaactcc gttttttct ttttttttat acgagaaaaa ccaaaaaat gtattttgc    7560
caaattctaa aatactatcc ccgaaatttt caatattttc tctttcagaa cgaactctgc    7620
gcgatgcttg tcgattgttg tgctcaacag cgtacctacg agcgattcta cggaatgctc    7680
atcgaacgtt tctgccgact tcgcctcgaa taccagcaat actttgaaaa gctctgccag    7740
gacacgtatt ccacgattca ccgaattgac atcacaaaac tgcggaattt ggctcgcctt    7800
attgctcatt tgctctcgac ggatgctatt gactggaaga ttttggccga tatgaaaatg    7860
accgaagagg acacaacttc ttctggcaga atctatatta aatatatatt taatgaactt    7920
gtggaggcga tgggaatggt taaacttcat tcgagagtta ctgatccgtg agtttcctag    7980
agagagttgt tttcgtattc aattttccct attttcagaa ctttggctca ttgctttgtt    8040
ggattattcc cacgaactaa tccgaacagc gcacgatttt cgatcaactt cttcacaatg    8100
attggattgg gtggtttgac gttggaactt cgtgaatggc tggcaaaggg tctcaagaag    8160
aagaagggaa tgctggatca gttgaaggcc gaatcaagct cagattcatc gtcgtcttcg    8220
gattcgtcag actcgtctga ttcttcggat tctgacgatt catccgactc gtcttcagat    8280
tcctcatctt cttcagaatc agagccagaa ccaccgaaga aaagaagaa gaagaacagt    8340
gaagagagtt ccaaaagaa ggaaaaagag aatattggtc gacgggatcg tggagacaag    8400
agagctgaac gtcatcgtga tcaaagtgtg gagaacaagg acaaggatcg tcgacgtcgc    8460
caggattctg acgaaaatcg tcggccagaa cgaggagatg accgcaagga tcggagtaaa    8520
gatcgtcgtc gtcaagactc ggatgatgag gatcggaaag gtcgtgaacg tcgggaagat    8580
tcagggaaa gacgtcgcgg agatcgggat cgacgtgatc gaaacaagga tcaggaggat    8640
caccgtgaag atcgccgtga ccgaagcaag gatcgtgagg atcgacgtga tcgccgtcgt    8700
catgactctg atgatgatcg taaaactcgt cgggatagaa gtgaagagcg aggaggacgt    8760
```

```
cgtcgtgaag tggaatcgga tgatcgacgc cgacgtcgtt gaattttcaa attttaaata   8820
ctgaatattt gttttttttc ctattattta tttattctct ttgtgttttt tttcttgctt   8880
tctaaaaaat taattcaatc caaatctaaa catgagcggt ttttttttctc tttccgtctc   8940
ccaattcgta ttccgctcct ctcatctgaa cacaatgtgc aagtttattt atcttctcgc   9000
tttcatttca ttaggacgtg gggggaattg gtggaagggg gaaacacaca aaaggatgat   9060
ggaaatgaaa taaggacaca caatatgcaa caacattcaa ttcagaaata tggaggaagg   9120
tttaaaagaa aacataaaaa tatatagagg aggaaggaaa actagtaaaa aataagcaaa   9180
gaaattaggc gaacgatgag aattgtcctc gcttggcaaa tgcgaatccg tatggagagg   9240
cacgtttggc gaaggcaaat gttcggtatg gagatctgta aaaatttta agttgaaatt   9300
tggtgttgct cttttacaaa attttccgat tttcgcttga aattacggtg ccaggtctcg   9360
acacgtcttc caatttttca aattcaaaag agcctttaat gggctgtagt tgctaatttc   9420
tcgttttga aaattttct tccgtttaat cgaaatttga tgtatttat ttatgatttt   9480
caataaattt caaagaaact ggtgaaaact cggaaaattg tgaactacag taatccaatc   9540
cttaaaggcg cacaccttt aaatgtccgc cccaatacga tatttttta agattcgcta   9600
gagcggccgc caccgcggtg gagctccaat tcgccctata gtgagtcgta ttacaattca   9660
ctggccgtcg ttttacaacg tcgtgactgg gaaaaccctg gcgttaccca acttaatcgc   9720
cttgcagcac atcccccctt cgccagctgg cgtaatagcg aagaggcccg caccgatcgc   9780
ccttcccaac agttgcgtag cctgaatggc gaatgggacg cgccctgtag cggcgcatta   9840
agcgcggcgg gtgtggtggt tacgcgcagc gtgaccgcta cacttgccag cgccctagcg   9900
cccgctcctt tcgctttctt cccttccttt ctcgccacgt tcgccggctt tccccgtcaa   9960
gctctaaatc gggggctccc tttagggttc cgatttagtg ctttacggca cctcgacccc  10020
aaaaaacttg attagggtga tggttcacgt agtgggccat cgccctgata gacggttttt  10080
cgccctttga cgttggagtc acgttctttt aatagtggac tcttgttcca aactggaaca  10140
acactcaacc ctatctcggt ctattctttt gatttataag ggattttgcc gatttcggcc  10200
tattggttaa aaaatgagct gatttaacaa aaatttaacg cgaattttaa caaaatatta  10260
acgtttacaa tttcaggtgg cacttttcgg ggaaatgtgc gcggaacccc tatttgttta  10320
tttttctaaa tacattcaaa tatgtatccg ctcatgagac aataaccctg ataaatgctt  10380
caataatatt gaaaaggaa gagtatgagt attcaacatt tccgtgtcgc ccttattccc  10440
tttttgcgg cattttgcct tcctgttttt gctcacccag aaacgctggt gaaagtaaaa  10500
gatgctgaag atcagttggg tgcacgagtg ggttacatcg aactggatct caacagcggt  10560
aagatccttg agagttttcg ccccgaagaa cgttttccaa tgatgagcac ttttaaagtt  10620
ctgctatgtg gcgcggtatt atcccgtatt gacgccgggc aagagcaact cggtcgccgc  10680
atacactatt ctcagaatga cttggttgag tactcaccag tcacagaaaa gcatcttacg  10740
gatggcatga cagtaagaga attatgcagt gctgccataa gcatgagtga taacactgcg  10800
gccaacttac ttctgacaac gatcggagga ccgaaggagc taaccgcttt ttttcacaac  10860
atggggatc atgtaactcg ccttgatcgt tgggaaccgg agctgaatga agccatacca  10920
aacgacgagc gtgacaccac gatgcctgta gcaatgcaa caacgttgcg caaactatta  10980
actggcgaac tacttactct agcttcccgg caacaattaa tagactggat ggaggcggat  11040
aaagttgcag gaccacttct gcgctcggcc cttccggctg gctggtttat tgctgataaa  11100
tctggagccg gtgagcgtgg gtctcgcggt atcattgcag cactggggcc agatggtaag  11160
```

```
cctccccgta tcgtagttat ctacacgacg ggcagtcagg caactatgga tgaacgaaat    11220
agacagatcg ctgagatagg tgcctcactg attaagcatt ggtaactgtc agaccaagtt    11280
tactcatata tactttagat tgatttaaaa cttcattttt aatttaaaag gatctaggtg    11340
aagatccttt ttgataatct catgaccaaa atcccttaac gtgagttttc gttccactga    11400
gcgtcagacc ccgtagaaaa gatcaaagga tcttcttgag atcctttttt tctgcgcgta    11460
atctgctgct tgcaaacaaa aaaaccaccg ctaccagcgg tggtttgttt gccggatcaa    11520
gagctaccaa ctctttttcc gaaggtaact ggcttcagca gagcgcagat accaaatact    11580
gtccttctag tgtagccgta gttaggccac cacttcaaga actctgtagc accgcctaca    11640
tacctcgctc tgctaatcct gttaccagtg gctgctgcca gtggcgataa gtcgtgtctt    11700
accgggttgg actcaagacg atagttaccg gataaggcgc agcggtcggg ctgaacgggg    11760
ggttcgtgca cacagcccag cttggagcga acgacctaca ccgaactgag atacctacag    11820
cgtgagcatt gagaaagcgc cacgcttccc gaagggagaa aggcggacag gtatccggta    11880
agcggcaggg tcggaacagg agagcgcacg agggagcttc caggggggaa cgcctggtat    11940
ctttatagtc ctgtcgggtt tcgccacctc tgacttgagc gtcgattttt gtgatgctcg    12000
tcaggggggc cgagcctatg gaaaaacgcc agcaacgcgg cctttttacg gttcctggcc    12060
ttttgctggc cttttgctca catgttcttt cctgcgttat cccctgattc tgtggataac    12120
cgtattaccg cctttgagtg agctgatacc gctcgccgca gccgaacgac cgagcgcagc    12180
gagtcagtga gcgaggaagc ggaagagcgc ccaatacgca aaccgcctct ccccgcgcgt    12240
tggccgattc attaatgcag ctggcacgac aggtttcccg actggaaagc gggcagtgag    12300
cgcaacgcaa ttaatgtgag ttacctcact cattaggcac cccaggcttt acactttatg    12360
cttccggctc ctatgttgtg tggaattgtg agcggataac aatttcacac aggaaacagc    12420
tatgaccatg attacgccaa gctcggaatt aaccctcact aaagggaaca aaagctgggg    12480
gg                                                                  12482

<210> SEQ ID NO 8
<211> LENGTH: 7209
<212> TYPE: DNA
<213> ORGANISM: Artificial Sequence
<220> FEATURE:
<223> OTHER INFORMATION: Description of Artificial Sequence:plasmid DNA

<400> SEQUENCE: 8
gatccgtcga cagatctccc tatagtgagt cgtattactg cagccaagct aattccgggc      60
gaatttctta tgatttatga ttttattat taaataagtt ataaaaaaaa taagtgtata     120 caaatttta agtgactctt aggttttaaa acgaaaattc ttgttcttga gtaactcttt     180
cctgtaggtc aggttgcttt ctcaggtata gcatgaggtc gctcttattg accacacctc     240
taccggcatg caagcttggc gtaatcatgg tcatagctgt ttcctgtgtg aaattgttat     300
ccgctcacaa ttccacacaa catacgagcc ggaagcataa agtgtaaagc ctggggtgcc     360
taatgagtga ggtaactcac attaattgcg ttgcgctcac tgcccgcttt ccagtcggga     420
aacctgtcgt gccagctgga ttaatgaatc ggccaacgcg cggggagagg cggtttgcgt     480
attgggcgct cttccgcttc ctcgctcact gactcgctgc gctcggtcgt tcggctgcgg     540
cgagcggtat cagctcactc aaaggcggta atacggttat ccacagaatc aggggataac     600
gcaggaaaga acatgtgagc aaaaggccag caaaaggcca ggaaccgtaa aaaggccgcg     660
ttgctggcgt ttttccatag gctccgcccc cctgacgagc atcacaaaaa tcgacgctca     720
```

```
agtcagaggt ggcgaaaccc gacaggacta taaagatacc aggcgtttcc ccctggaagc    780
tccctcgtgc gctctcctgt tccgaccctg ccgcttaccg gatacctgtc cgcctttctc    840
ccttcgggaa gcgtggcgct ttctcatagc tcacgctgta ggtatctcag ttcggtgtag    900
gtcgttcgct ccaagctggg ctgtgtgcac gaaccccccg ttcagcccga ccgctgcgcc    960
ttatccggta actatcgtct tgagtccaac ccggtaagac acgacttatc gccactggca   1020
gcagccactg gtaacaggat tagcagagcg aggtatgtag gcggtgctac agagttcttg   1080
aagtggtggc ctaactacgg ctacactaga aggacagtat ttggtatctg cgctctgctg   1140
aagccagtta ccttcggaaa aagagttggt agctcttgat ccggcaaaca aaccaccgct   1200
ggtagcggtg ttttttttgt ttgcaagcag cagattacgc gcagaaaaaa aggatctcaa   1260
gaagatcctt tgatcttttc tacggggtct gacgctcagt ggaacgaaaa ctcacgttaa   1320
gggattttgg tcatgagatt atcaaaaagg atcttcacct agatcctttt aaattaaaaa   1380
tgaagtttta aatcaatcta agtatatat gagtaaactt ggtctgacag ttaccaatgc   1440
ttaatcagtg aggcacctat ctcagcgatc tgtctatttc gttcatccat agttgcctga   1500
ctccccgtcg tgtagataac tacgatacgg gagggcttac catctggccc cagtgctgca   1560
atgataccgc gagacccacg ctcaccggct ccagatttat cagcaataaa ccagccagcc   1620
ggaagggccg agcgcagaag tggtcctgca actttatccg cctccatcca gtctattaat   1680
tgttgccggg aagctagagt aagtagttcg ccagttaata gtttgcgcaa cgttgttgcc   1740
attgctacag gcatcgtggt gtcacgctcg tcgtttggta tggcttcatt cagctccggt   1800
tcccaacgat caaggcgagt tacatgatcc cccatgttgt gcaaaaaagc ggttagctcc   1860
ttcggtcctc cgatcgttgt cagaagtaag ttggccgcag tgttatcact catggttatg   1920
gcagcactgc ataattctct tactgtcatg ccatccgtaa gatgcttttc tgtgactggt   1980
gagtactcaa ccaagtcatt ctgagaatag tgtatgcggc gaccgagttg ctcttgcccg   2040
gcgtcaatac gggataatac cgcgccacat agcagaactt taaaagtgct catcattgga   2100
aaacgttctt cggggcgaaa actctcaagg atcttaccgc tgttgagatc cagttcgatg   2160
taacccactc gtgcacccaa ctgatcttca gcatctttta ctttcaccag cgtttctggg   2220
tgagcaaaaa caggaaggca aaatgccgca aaaaagggaa taagggcgac acggaaatgt   2280
tgaatactca tactcttcct ttttcaatat tattgaagca tttatcaggg ttattgtctc   2340
atgagcggat acatatttga atgtatttag aaaaataaac aaataggggt tccgcgcaca   2400
tttccccgaa aagtgccacc tgaacgaagc atctgtgctt cattttgtag aacaaaaatg   2460
caacgcgaga gcgctaattt ttcaaacaaa gaatctgagc tgcattttta cagaacagaa   2520
atgcaacgcg aaagcgctat tttaccaacg aagaatctgt gcttcatttt tgtaaaacaa   2580
aaatgcaacg cgagagcgct aatttttcaa acaaagaatc tgagctgcat ttttacagaa   2640
cagaaatgca acgcgagagc gctatttttac caacaaagaa tctatacttc ttttttgttc   2700
tacaaaaatg catcccgaga gcgctatttt tctaacaaag catcttagat tactttttttt   2760 ctcctttgtg cgctctataa tgcagtctct tgataacttt ttgcactgta ggtccgttaa   2820
ggttagaaga aggctacttt ggtgtctatt ttctcttcca taaaaaaagc ctgactccac   2880
ttcccgcgtt tactgattac tagcgaagct gcgggtgcat ttttcaaga taaggcatc   2940 cccgattata ttctataccg atgtggattg cgcatacttt gtgaacagaa agtgatagcg   3000
ttgatgattc ttcattggtc agaaaattat gaacggtttc ttctattttg tctctatata   3060
ctacgtatag gaaatgttta cattttcgta ttgttttcga ttcactctat gaatagttct   3120
```

```
tactacaatt tttttgtcta aagagtaata ctagagataa acataaaaaa tgtagaggtc    3180
gagtttagat gcaagttcaa ggagcgaaag gtggatgggt aggttatata gggatatagc    3240
acagagatat atagcaaaga gatacttttg agcaatgttt gtggaagcgg tattcgcaat    3300
attttagtag ctcgttacag tccggtgcgt ttttggtttt ttgaaagtgc gtcttcagag    3360
cgcttttggt tttcaaaagc gctctgaagt tcctatactt tctagagaat aggaacttcg    3420
gaataggaac ttcaaagcgt ttccgaaaac gagcgcttcc gaaaatgcaa cgcgagctgc    3480
gcacatacag ctcactgttc acgtcgcacc tatatctgcg tgttgcctgt atatatatat    3540
acatgagaag aacggcatag tgcgtgttta tgcttaaatg cgtacttata tgcgtctatt    3600
tatgtaggat gaaaggtagt ctagtacctc ctgtgatatt atcccattcc atgcggggta    3660
tcgtatgctt ccttcagcac taccctttag ctgttctata tgctgccact cctcaattgg    3720
attagtctca tccttcaatg ctatcatttc ctttgatatt ggatcatatt aagaaaccat    3780
tattatcatg acattaacct ataaaaatag gcgtatcacg aggccctttc gtctcgcgcg    3840
tttcggtgat gacggtgaaa acctctgaca catgcagctc ccggagacgg tcacagcttg    3900
tctgtaagcg gatgccggga gcagacaagc ccgtcagggc gcgtcagcgg gtgttggcgg    3960 gtgtcgggc tggcttaact atgcggcatc agagcagatt gtactgagag tgcaccatag    4020
atcaacgaca ttactatata tataatatag gaagcattta atagacagca tcgtaatata    4080
tgtgtacttt gcagttatga cgccagatgg cagtagtgga agatattctt tattgaaaaa    4140
tagcttgtca ccttacgtac aatcttgatc cggagctttt ctttttttgc cgattaagaa    4200
ttaattcggt cgaaaaaaga aaggagagg gccaagaggg agggcattgg tgactattga    4260
gcacgtgagt atacgtgatt aagcacacaa aggcagcttg gagtatgtct gttattaatt    4320
tcacaggtag ttctggtcca ttggtgaaag tttgcggctt gcagagcaca gaggccgcag    4380
aatgtgctct agattccgat gctgacttgc tgggtattat atgtgtgccc aatagaaaga    4440
gaacaattga cccggttatt gcaaggaaaa tttcaagtct tgtaaaagca tataaaaata    4500
gttcaggcac tccgaaatac ttggttggcg tgtttcgtaa tcaacctaag gaggatgttt    4560
tggctctggt caatgattac ggcattgata tcgtccaact gcatggagat gagtcgtggc    4620
aagaatacca agagttcctc ggtttgccag ttattaaaag actcgtattt ccaaaagact    4680
gcaacatact actcagtgca gcttcacaga aacctcattc gtttattccc ttgtttgatt    4740
cagaagcagg tgggacaggt gaacttttgg attggaactc gatttctgac tgggttggaa    4800
ggcaagagag ccccgaaagc ttacatttta tgttagctgg tggactgacg ccagaaaatg    4860
ttggtgatgc gcttagatta aatggcgtta ttggtgttga tgtaagcgga ggtgtggaga    4920
caaatggtgt aaaagactct aacaaaatag caaatttcgt caaaaatgct aagaaatagg    4980
ttattactga gtagtattta tttaagtatt gtttgtgcac ttgccgatct atgcggtgtg    5040
aaataccgca cagatgcgta aggagaaaat accgcatcag gaaattgtaa acgttaatat    5100
tttgttaaaa ttcgcgttaa attttttgtta aatcagctca ttttttaacc aataggccga    5160
aatcggcaaa atcccttata aatcaaaaga atagaccgag atagggttga gtgttgttcc    5220
agtttggaac aagagtccac tattaaagaa cgtggactcc aacgtcaaag ggcgaaaaac    5280
cgtctatcag ggcgatggcc cactacgtga accatcaccc taatcaagtt ttttggggtc    5340
gaggtgccgt aaagcactaa atcggaaccc taaagggagc ccccgattta gagcttgacg    5400 gggaagccg cgaacgtgg cgagaaagga agggaagaaa gcgaaaggag cgggcgctag    5460
ggcgctggca agtgtagcgg tcacgctgcg cgtaaccacc acacccgccg cgcttaatgc    5520
```

```
gccgctacag ggcgcgtcgc gccattcgcc attcaggctg cgcaactgtt gggaagggcg    5580
atcggtgcgg gcctcttcgc tattacgcca gctggcgaaa ggggatgtg ctgcaaggcg      5640 attaagttgg gtaacgccag ggttttccca gtcacgacgt tgtaaaacga cggccagtcg    5700
tccaagcttt cgcgagctcg agatcccgag ctttgcaaat taaagccttc gagcgtccca    5760
aaaccttctc aagcaaggtt ttcagtataa tgttacatgc gtacacgcgt ctgtacagaa    5820 aaaaagaaa aatttgaaat ataaataacg ttcttaatac taacataact ataaaaaat     5880 aaatagggac ctagacttca ggttgtctaa ctccttcctt ttcggttaga gcggatgtgg    5940
ggggagggcg tgaatgtaag cgtgacataa ctaattcat gatatccttt tgttgtttcc     6000
gggtgtacaa tatggacttc ctcttttctg gcaaccaaac ccatacatcg ggattcctat    6060
aataccttcg ttggtctccc taacatgtag gtggcggagg ggagatatac aatagaacag    6120
ataccagaca agacataatg ggctaaacaa gactacacca attacactgc ctcattgatg    6180
gtggtacata acgaactaat actgtagccc tagacttgat agccatcatc atatcgaagt    6240
ttcactaccc tttttccatt tgccatctat tgaagtaata ataggcgcat gcaacttctt    6300 ttctttttt ttcttttctc tctccccgt tgttgtctca ccatatccgc aatgacaaaa       6360
aaaatgatgg aagacactaa aggaaaaaat taacgacaaa gacagcacca acagatgtcg    6420
ttgttccaga gctgatgagg ggtatcttcg aacacacgaa acttttccct tccttcattc    6480
acgcacacta ctctctaatg agcaacggta tacgccttc cttccagtta cttgaatttg      6540
aaataaaaaa agtttgccgc tttgctatca agtataaata gacctgcaat tattaatcct    6600
ttgtttcctc gtcattgttc tcgttccctt tcttccttgt ttcttttttct gcacaatatt    6660 tcaagctata ccaagcatac aatcaactcc aagcttgaag caagcctcct gaaagatgaa    6720
gctactgtct tctatcgaac aagcatgcga tatttgccga cttaaaaagc tcaagtgctc    6780
caaagaaaaa ccgaagtgcg ccaagtgtct gaagaacaac tgggagtgtc gctactctcc    6840
caaaaccaaa aggtctccgc tgactagggc acatctgaca gaagtggaat caaggctaga    6900
aagactggaa cagctatttc tactgatttt tcctcgagaa gaccttgaca tgattttgaa    6960
aatggattct ttacaggata taaaagcatt gttaacagga ttatttgtac aagataatgt     7020
gaataaagat gccgtcacag atagattggc ttcagtggag actgtatagc ctctaacatt    7080
gagacagcat agaataagtg cgacatcatc atcggaagag agtagtaaca aaggtcaaag    7140
acagttgact gtatcgccgg aattcttaat acgactcact atagggcata tggccatgga    7200
ggccccggg                                                              7209
```

<210> SEQ ID NO 9
<211> LENGTH: 6820
<212> TYPE: DNA
<213> ORGANISM: Artificial Sequence
<220> FEATURE:
<223> OTHER INFORMATION: Description of Artificial Sequence:plasmid DNA

<400> SEQUENCE: 9

```
gatccgtcga cagatctccc tatagtgagt cgtattactg cagagatcta tgaatcgtag      60
atactgaaaa accccgcaag ttcacttcaa ctgtgcatcg tgcaccatct caatttcttt     120
catttataca tcgttttgcc ttcttttatg taactatact cctctaagtt tcaatcttgg     180
ccatgtaacc tctgatctat agaatttttt aaatgactag aattaatgcc catctttttt    240
ttggacctaa attcttcatg aaaatatatt acgagggctt attcagaagc tttggacttc     300
ttcgccagag gtttggtcaa gtctccaatc aaggttgtcg gcttgtctac cttgccagaa    360
```

```
atttacgaaa agatggaaaa gggtcaaatc gttggtagat acgttgttga cacttctaaa    420
taagcgaatt tcttatgatt tatgattttt attattaaat aagttataaa aaaataagt     480 gtatacaaat tttaaagtga ctcttaggtt ttaaaacgaa aattcttgtt cttgagtaac    540 tcttcctgt aggtcaggtt gctttctcag gtatagcatg aggtcgctct tattgaccac     600
acctctaccg gcatgcccga aattcccta ccctatgaac atattccatt ttgtaatttc     660
gtgtcgtttc tattatgaat ttcatttata aagtttatgt acaaatatca taaaaaaga    720 gaatctttt aagcaaggat tttcttaact tcttcggcga cagcatcacc gacttcggtg     780
gtactgttgg aaccacctaa atcaccagtt ctgatacctg catccaaaac cttttaact     840 gcatcttcaa tggccttacc ttcttcaggc aagttcaatg acaatttcaa catcattgca    900
gcagacaaga tagtggcgat agggtcaacc ttattctttg gcaaatctgg agcagaaccg    960
tggcatggtt cgtacaaacc aaatgcggtg ttcttgtctg gcaaagaggc caaggacgca   1020
gatggcaaca aacccaagga acctgggata acggaggctt catcggagat gatatcacca   1080
aacatgttgc tggtgattat aataccattt aggtgggttg ggttcttaac taggatcatg   1140
gcggcagaat caatcaattg atgttgaacc ttcaatgtag gaaattcgtt cttgatggtt   1200
tcctccacag ttttctcca taatcttgaa gaggccaaaa cattagcttt atccaaggac    1260
caaataggca atggtggctc atgttgtagg gccatgaaag cggccattct tgtgattctt   1320
tgcacttctg gaacggtgta ttgttcacta tcccaagcga caccatcacc atcgtcttcc   1380
tttctcttac caaagtaaat acctcccact aattctctga caacaacgaa gtcagtacct   1440
ttagcaaatt gtggcttgat tggagataag tctaaaagag agtcggatgc aaagttacat   1500
ggtcttaagt tggcgtacaa ttgaagttct ttacggattt ttagtaaacc ttgttcaggt   1560
ctaacactac ctgtacccca tttaggacca cccacagcac ctaacaaaac ggcatcaacc   1620
ttcttggagg cttccagcgc ctcatctgga agtgggacac ctgtagcatc gatagcagca   1680
ccaccaatta aatgattttc gaaatcgaac ttgacattgg aacgaacatc agaaatagct   1740
ttaagaacct taatggcttc ggctgtgatt tcttgaccaa cgtggtcacc tggcaaaacg   1800
acgatcttct taggggcaga cattagaatg gtatatcctt gaaatatata tatatattgc   1860
tgaaatgtaa aaggtaagaa aagttagaaa gtaagacgat tgctaaccac ctattggaaa   1920
aaacaatagg tccttaaata atattgtcaa cttcaagtat tgtgatgcaa gcatttagtc   1980
atgaacgctt ctctattcta tatgaaaagc cggttccggc ctctcacctt tccttttct    2040 cccaattttt cagttgaaaa aggtatatgc gtcaggcgac ctctgaaatt aacaaaaaat   2100
ttccagtcat cgaatttgat tctgtgcgat agcgccctg tgtgttctcg ttatgttgag    2160 gaaaaaata atggttgcta agagattcga actcttgcat cttacgatac ctgagtattc    2220
ccacagttgg ggatctcgac tctagctaga ggatcaattc gtaatcatgg tcatagctgt   2280
ttcctgtgtg aaattgttat ccgctcacaa ttccacacaa catacgagcc ggaagcataa   2340
agtgtaaagc ctggggtgcc taatgagtga ggtaactcac attaattgcg ttgcgctcac   2400
tgcccgcttt ccagtcggga aacctgtcgt gccagctgga ttaatgaatc ggccaacgcg   2460
cggggagagg cggtttgcgt attgggcgct cttccgcttc ctcgctcact gactcgctgc   2520
gctcggtcgt tcggctgcgg cgagcggtat cagctcactc aaaggcggta atacggttat   2580
ccacagaatc aggggataac gcaggaaaga acatgtgagc aaaaggccag caaaaggcca   2640
ggaaccgtaa aaaggccgcg ttgctggcgt ttttccatag gctccgcccc cctgacgagc   2700
atcacaaaaa tcgacgctca agtcagaggt ggcgaaaccc gacaggacta taaagatacc   2760
```

```
aggcgtttcc ccctggaagc tccctcgtgc gctctcctgt tccgaccctg ccgcttaccg    2820 gataccctgtc cgccctttctc ccttcgggaa gcgtggcgct ttctcatagc tcacgctgta   2880
ggtatctcag ttcggtgtag gtcgttcgct ccaagctggg ctgtgtgcac gaaccccccg    2940
ttcagcccga ccgctgcgcc ttatccggta actatcgtct tgagtccaac ccggtaagac    3000
acgacttatc gccactggca gcagccactg gtaacaggat tagcagagcg aggtatgtag    3060
gcggtgctac agagttcttg aagtggtggc ctaactacgg ctacactaga aggacagtat    3120
ttggtatctg cgctctgctg aagccagtta ccttcgggaaa aagagttggt agctcttgat   3180
ccggcaaaca aaccaccgct ggtagcggtg gttttttttgt ttgcaagcag cagattacgc    3240
gcagaaaaaa aggatctcaa gaagatcctt tgatcttttc tacggggtct gacgctcagt    3300
ggaacgaaaa ctcacgttaa gggattttgg tcatgagatt atcaaaaagg atcttcacct    3360
agatcctttt aaattaaaaa tgaagtttta atcaatcta aagtatatat gagtaaactt    3420
ggtctgacag ttaccaatgc ttaatcagtg aggcacctat ctcagcgatc tgtctatttc    3480
gttcatccat agttgcctga ctccccgtcg tgtagataac tacgatacgg agggcttac    3540 catctggccc cagtgctgca atgataccgc gagacccacg ctcaccggct ccagatttat    3600
cagcaataaa ccagccagcc ggaagggccg agcgcagaag tggtcctgca actttatccg    3660
cctccatcca gtctattaat tgttgccggg aagctagagt aagtagttcg ccagttaata    3720
gtttgcgcaa cgttgttgcc attgctacag gcatcgtggt gtcacgctcg tcgtttggta    3780
tggcttcatt cagctccggt tcccaacgat caaggcgagt tacatgatcc cccatgttgt    3840
gcaaaaaagc ggttagctcc ttcggtcctc cgatcgttgt cagaagtaag ttggccgcag    3900
tgttatcact catggttatg gcagcactgc ataattctct tactgtcatg ccatccgtaa    3960
gatgcttttc tgtgactggt gagtactcaa ccaagtcatt ctgagaatag tgtatgcggc    4020
gaccgagttg ctcttgcccg gcgtcaatac gggataatac cgcgccacat agcagaactt    4080
taaaagtgct catcattgga aaacgttctt cggggcgaaa actctcaagg atcttaccgc    4140
tgttgagatc cagttcgatg taacccactc gtgcacccaa ctgatcttca gcatctttta    4200
ctttcaccag cgtttctggg tgagcaaaaa caggaaggca aaatgccgca aaaaagggaa    4260
taagggcgac acggaaatgt tgaatactca tactcttcct ttttcaatat tattgaagca    4320
tttatcaggg ttattgtctc atgagcggat acatatttga atgtatttag aaaaataaac    4380
aaataggggt tccgcgcaca tttccccgaa aagtgccacc tgacgtctaa gaaaccatta    4440
ttatcatgac attaacctat aaaaataggc gtatcacgag gccctttcgt ctcgcgcgtt    4500
tcggtgatga cggtgaaaac ctctgacaca tgcagctccc ggagacggtc acagcttgtc    4560
tgtaagcgga tgccgggagc agacaagccc gtcagggcgc gtcagcgggt gttggcgggt    4620 gtcgggctg gcttaactat gcggcatcag agcagattgt actgagagtg caccataacg    4680
catttaagca taaacacgca ctatgccgtt cttctcatgt atatatatat acaggcaaca    4740
cgcagatata ggtgcgacgt gaacagtgag ctgtatgtgc gcagctcgcg ttgcattttc    4800
ggaagcgctc gttttcggaa acgctttgaa gttcctattc cgaagttcct attctctagc    4860
tagaaagtat aggaacttca gagcgctttt gaaaccaaa agcgctctga agacgcactt    4920
tcaaaaaacc aaaacgcac cggactgtaa cgagctacta aatattgcg aataccgctt    4980 ccacaaacat tgctcaaaag tatctctttg ctatatatct ctgtgctata tccctatata    5040
acctacccat ccacctttcg ctccttgaac ttgcatctaa actcgacctc tacatttttt    5100
atgtttatct ctagtattac tctttagaca aaaaaattgt agtaagaact attcatagag    5160
```

-continued

```
tgaatcgaaa acaatacgaa aatgtaaaca tttcctatac gtagtatata gagacaaaat    5220
agaagaaacc gttcataatt ttctgaccaa tgaagaatca tcaacgctat cactttctgt    5280
tcacaaagta tgcgcaatcc acatcggtat agaatataat cggggatgcc tttatcttga    5340
aaaaatgcac ccgcagcttc gctagtaatc agtaaacgcg ggaagtggag tcaggctttt    5400
tttatggaag agaaaataga caccaaagta gccttcttct aaccttaacg gacctacagt    5460
gcaaaaagtt atcaagagac tgcattatag agcgcacaaa ggagaaaaaa agtaatctaa    5520
gatgctttgt tagaaaaata gcgctctcgg gatgcatttt tgtagaacaa aaagaagta    5580 tagattcttt gttggtaaaa tagcgctctc gcgttgcatt tctgttctgt aaaaatgcag    5640
ctcagattct ttgtttgaaa attagcgct ctcgcgttgc attttgtttt acaaaaatg    5700 aagcacagat tcttcgttgg taaaatacg ctttcgcgtt gcatttctgt tctgtaaaaa    5760
tgcagctcag attctttgtt tgaaaaatta gcgctctcgc gttgcatttt tgttctacaa    5820
aatgaagcac agatgcttcg ttgcttgcat gcaacttctt ttcttttttt ttcttttctc    5880 tctccccgt tgttgtctca ccatatccgc aatgacaaaa aaaatgatgg aagacactaa    5940
aggaaaaaat taacgacaaa gacagcacca acagatgtcg ttgttccaga gctgatgagg    6000
ggtatcttcg aacacacgaa acttttcct tccttcattc acgcacacta ctctctaatg    6060
agcaacggta tacggccttc cttccagtta cttgaatttg aaataaaaaa agtttgccgc    6120
tttgctatca agtataaata gacctgcaat tattaatctt ttgtttcctc gtcattgttc    6180
tcgttccctt tcttccttgt ttcttttct gcacaatatt tcaagctata ccaagcatac    6240
aatcaactcc aagctttgca aagatggata aagcggaatt aattcccgag cctccaaaaa    6300
agaagagaaa ggtcgaattg ggtaccgccg ccaatttaa tcaaagtggg aatattgctg    6360
atagctcatt gtccttcact ttcactaaca gtagcaacgg tccgaacctc ataacaactc    6420
aaacaaattc tcaagcgctt tcacaaccaa ttgcctcctc taacgttcat gataacttca    6480
tgaataatga aatcacggct agtaaaattg atgatggtaa taattcaaaa ccactgtcac    6540
ctggttggac ggaccaaact gcgtataacg cgtttggaat cactacaggg atgtttaata    6600
ccactacaat ggatgatgta tataactatc tattcgatga tgaagatacc ccaccaaacc    6660
caaaaaaaga gatcgaattc ttaatacgac tcactatagg gcccatggac gaagaatcca    6720
gttcattctt atgtacctat gctgagaatc gtgccaataa gaagccaata cttccttaga    6780
tgatgcaata aatattaaaa taaaacaaaa cagaaggctg                          6820
```

<210> SEQ ID NO 10
<211> LENGTH: 10597
<212> TYPE: DNA
<213> ORGANISM: Artificial Sequence
<220> FEATURE:
<223> OTHER INFORMATION: Description of Artificial Sequence:plasmid DNA

<400> SEQUENCE: 10

```
ccggtggtac cgggcccccc ctcgaggtcg acggtatcga taagctttcg tcattgaaaa      60
gaaggataag aatggacgat gggaagaagc tctcgttgtt ccaggagatc agaaaacagc     120
aactgttcca atcttaagg agggagaaga atatcaattc agaatttctg ctcgtaacaa     180
ggctggaact ggagatcctt ctgatccttt gatcgtgtt gttgcgaagc caagaaacct     240
tgctccaaga attcatcgtg aagatctttc tgatacaact gtcaaggtcg agccactct     300 caagttcatt gttcatattg atggtgagcc agcaccagat gtaacatggt cattcaatgg     360
aaaaggaatc ggagagagca aggctcaaat tgaaaatgag ccatacatct cgagatttgc     420
```

```
tttgccaaag gcacttcgta agcaaagtgg aaaatatacc atcactgcaa ccaacattaa    480
tggaactgac agtgtcacta tcaatatcaa ggtaaaaagc aagccaacga aaccaaaggg    540
accaatcgag gtaactgatg tcttcgaaga tcgtgcaact cttgactgga aaccaccaga    600
ggatgacgga ggagagccaa ttgagttcta tgaaattgaa aagatgaaca ccaaggacgg    660
aatctgggtt ccatgtggac gtagtggaga tacccacttc acagtcgatt cactcaacaa    720
gggagatcat tacaagttcc gtgtcaaggc tgtcaacagc gaaggacctt ctgatccatt    780
ggaaactgaa accgatattt tggctaaaaa tccatttgat cgtccagata gaccaggtcg    840
tccagagcca actgattggg attctgatca tgttgatctc aagtgggatc cactagttct    900
agaagcgctg ctaagggggc cctcgtcgag tcggtcacaa tcacctgaaa ctccaaaggc    960
agccagtgag gaacgtgaag aagaagaaaa agagtcatct gaacaggttt gattttcttt   1020
ctggtcaaaa agatgaaatt attgattttc agccagatac tcccaaaact agcagcgaga   1080
agtctgcaag tcgttcacag tcgcccagag aatcgcggga agtgagccaa gaggtatgtt   1140
tttcaaaaat caataactga tcataatttt tattgtttgg tgaatttaag aaaataatat   1200
tcgaaaattc ctctgaatta tcaagattgc agtattaatt tcgagaaaaa ttgagatatt   1260
catagagcta ttgtaaattt tcttgatttc agactgaaac ttcggaaaat caagagaaaa   1320
tcaaagaaaa ggatgacggg gatgatcagc ctggcacacc gaacagctat agaagccggg   1380
aaacttcacc agctccaaaa aggtccaagg agaccaggtt tgtcaaaagc ttcctgcgat   1440
taattctcat ttcaattttt cagagaatca gagtctcctg aaaaatcccc ggttcgttca   1500
agatctccca gaaggtcttc agcacgttcc ccgtcacgat ctcctagacg gcgccgagaa   1560
agaagctcag aaagaaagca atccgaagag ccagcaccgc taccagagaa aaagaagaaa   1620
gagccgctgg atattctacg aacaagaacc ggaggagcat atattccacc cgccaaactt   1680
cgacttatgc aacaacagat tagtgataag caaagtgaac agtatcagag aatgaattgg   1740
gaaagaatga agaaaaagat tcacggattg gttaacagag tcaacgcgaa gaatcttgtt   1800
caaattgtca gagaacttct tcaagagaat gtgattcgtt caagtgagt gagaaaatcg   1860
aaggaaaagg aaagaattaa tttaattttt cagggacatt ctctgccgtg acattattca   1920
agctcaggct ttctcaccag gattctctaa cgtctatgca gctttggcgg cagttatcaa   1980
ctcgaaattc cctcatgtcg gtgaacttct tctccgtcgt ctgattgtac agttcaaaag   2040
aagtttccgt agaaatgaca gaggcgtcac ggtgaacgtg atcaaattca tcgcacattt   2100
gattaatcaa caagttgctc acgaagttct tgcgctggaa atcatgattc tgatgcttga   2160
agaaccaact gatgattcag ttgaagtcgc cattgcgttc ctgaaagagt gtggagcaaa   2220
gcttctggag attgctccag cagctcttaa cagtgtctac gaccgtcttc gtgcaattct   2280
catgaaaact gaaagatcgg aaaatgcact ggatcgacgt attcagtata tgattgagac   2340
tgcaatgcag attcgaaagg acaaatttgc ggtaaggtag aatatataaa tagtttatta   2400
gaaaaaaata aattagaata atttaaattc ctactagcca atcaggcgac cttttttgcgc   2460
atagttctat tattgaaaaa tttggagaat ttctcatatt ctcgctcgga aatctggaat   2520
tcgacgagat cttctggctt ctgtgcagct gcatcgcttt gtgctcccctt tctcgcttgt   2580
cttctgtgta caccaagaac cttgttgagt tcatcaactg aatctgtgac tggcttgttg   2640
ctcactggat gcactagacg actgattctc gagaaatcag attgagttgc gattagggtg   2700
acctagaaat tgggaataat acgaactttt gaaatattcc aggaggatta aaaaaattat   2760
tctcgacaat cctacaaatt tacttattgc accatgttgc tccaacattt ttcattaaaa   2820
```

```
gttaatgaaa aaatgtagaa aatcggaaat tggcaatttt cagaccattt ttaagcattt      2880
tcaaaaaaaa attgcagctg aaataaatgt cattttcaga taaatcgagc gatttctgt       2940 tgtctgacac tagtttttag ttttaaaaaa tgttggaaga acatggtgca ataggtaatt      3000
tcatagaatt tccatgtgtt tttttcaat taaccaatta tccaaatctt ccaaactcac       3060
attttgcgga gctgggctat caagaatctg ctgcagtttt ataagacgag catctctgat     3120
atcactgaaa attaattttt aatcaaaact tgaatatcaa ctaaacccac ttattaactt     3180
tctcgatctt ctgtcgttcg gtacgatgac ggtgaagaag ccaattgtag tagttgattt     3240
ggttcaagtc ctttcggtgt tgtacgtcag tgtcctgcaa tgctatttag ttataactta    3300
ggcctaagat tcaatttaat gaagtgatta aatttgttct ctgaacctct taagatgatc    3360
ttttggatta gaaacatata agacaggttt acctatctat taaaaaacag atcaaaatag    3420
atacgaccaa atcggataat ccatgcctac ctggcatcta ggaacgtgtt cttagaagat    3480
ttcttacgta atcgtatgaa gaaataacaa tttgatcgtt ggccagcaaa ataggggttt    3540
taagtgggat agtgttttta ttagctaacc ggaaaatttt atagtttttt tttgcaagaa    3600
accactgaaa acccccctaat tgtatacatt ttttggagca gcttctggtc tttttgagca  3660
ataaaattcg ataaaacaga atttaagtgt aaattgttca catttagttt ctattttatc   3720
aaattttgtt gctcaaaaac attcgaagct gctctaaaaa aatgcattaa aaagggggtt   3780
ttcagtggtt tttcacatta aaaaagctaa ttttaactaa aaatccatca tatttccaac   3840
tttgtcacaa caataaaatg ctggtcaaaa tgtgttcgaa aaaatgtttt tttttttaat   3900
ttttataatt taaaaatagt tttctttcgc tgggacacat acatttttgg gcgtaaattt   3960
tcagttcaaa tttccatttt tacaaccata atcataaagc tacgtctgat ctctctcgca   4020
cttacctgcg cctgattcga aagaacaacc gtagccaaaa gaacaagaag aacaagcacg   4080
tagttgtggt agtggacgtt catcacgcaa tactgaccaa tggtcgtggg gtctcacttt   4140
ccgtactatt gagagagggg agactgaaga tggcaattga ggacagtgtc ttcgacgcac   4200
gcatgcatcc ataagcataa tccaggaggg atggagagaa aaatcttgtt ctaagcccc    4260 tcccttgta atacatacac atatctaata ccgaagaatg gctaattgaa tggacgtcag    4320
ctgttgctgt agttgccaag gcatcatcga tgaaataact gaaagaaaga attaaataat    4380
tattgcaggc gtatccggcg gtcattgaag acttggactt gattgaggag gaggatcaga   4440
tcatccatac acttaatttg gaggatgcgg ttgatccgga aaatgggctt agtaagtgac   4500
tgaccacacg cggggggcat taatttaata aattgaattc catttcagat gtgttcaaac  4560
tagatccaga attcgaaaag aacgaggagg tttatgagga gatccgtaag gaaatcattg   4620
gaaacgccga tatttcggat gaggatggtg gcgacgagtt ggatgatgaa gaagagggta   4680
gtgatgtgga agaggctccg aagaagacta cagagattat tgataatact gatcagaatt   4740
gactgctttc agaaggtatt catttgagt tttgggccgg caaatctgta agttgccggt    4800
tgccgaaaat ttgctgaatt tgccggaaaa aaaaattccg gaatttatt aaaaactttt    4860 tgtaaaaatt aaattaaatt tgcaactttt cagagaagtc tacctgacaa tgcaatcatc    4920
tttggactac caagaagctg ctcacaaatt gctgaaaatg aagattccag acagcatgca    4980
ggtcagcgat gttgcaaaga aaatttttcg accaaaaaaa ccaaccaatc ataaaattta    5040
aaaaaaaact ccgtttttt ctttttttt atacgagaaa aaccaaaaaa atgtattttt      5100
gccaaattct aaaatactat ccccgaaatt ttcaatattt tctctttcag aacgaactct   5160
gcgcgatgct tgtcgattgt tgtgctcaac agcgtaccta cgagcgattc tacggaatgc   5220
```

```
tcatcgaacg tttctgccga cttcgcctcg aataccagca atactttgaa aagctctgcc    5280
aggacacgta ttccacgatt caccgaattg acatcacaaa actgcggaat ttggctcgcc    5340
ttattgctca tttgctctcg acggatgcta ttgactggaa gattttggcc gatatgaaaa    5400
tgaccgaaga ggacacaact tcttctggca gaatctatat aaatatata tttaatgaac     5460 ttgtggaggc gatgggaatg gttaaacttc attcgagagt tactgatccg tgagtttcct    5520
agagagagtt gttttcgtat tcaatttttcc ctattttcag aactttggct cattgctttg   5580
ttggattatt cccacgaact aatccgaaca gcgcacgatt ttcgatcaac ttcttcacaa    5640
tgattggatt gggtggtttg acgttggaac ttcgtgaatg gctggcaaag ggtctcaaga    5700
agaagaaggg aatgctggat cagttgaagg ccgaatcaag ctcagattca tcgtcgtctt    5760
cggattcgtc agactcgtct gattcttcgg attctgacga ttcatccgac tcgtcttcag    5820
attcctcatc ttcttcagaa tcagagccag aaccaccgaa gaaaagaag aagaagaaca     5880 gtgaagagag ttccaaaaag aaggaaaaag agaatattgg tcgacgggat cgtggagaca    5940
agagagctga acgtcatcgt gatcaaagtg tggagaacaa ggacaaggat cgtcgacgtc    6000
gccaggattc tgacgaaaat cgtcggccag aacgaggaga tgaccgcaag gatcggagta    6060
aagatcgtcg tcgtcaagac tcggatgatg aggatcggaa aggtcgtgaa cgtcgggaag    6120
attcagggga aagacgtcgc ggagatcggg atcgacgtga tcgaaacaag gatcaggagg    6180
atcaccgtga agatcgccgt gaccgaagca aggatcgtga ggatcgacgt gatcgccgtc    6240
gtcatgactc tgatgatgat cgtaaaactc gtcgggatag aagtgaagag cgaggaggac    6300
gtcgtcgtga agtggaatcg gatgatcgac gccgacgtcg ttgaattttc aaattttaaa    6360
tactgaatat ttgtttttttt tcctattatt tatttattct ctttgtgttt ttttctttgc   6420
tttctaaaaa attaattcaa tccaaatcta aacatgagcg gtttttttttc tctttccgtc   6480 tcccaattcg tattccgctc ctctcatctg aacacaatgt gcaagtttat ttatcttctc    6540
gctttcattt cattaggacg tgggggggaat tggtggaagg gggaaacaca caaaaggatg   6600
atggaaatga aataaggaca cacaatatgc aacaacattc aattcagaaa tatggaggaa    6660
ggtttaaaag aaaacataaa aatatataga ggaggaagga aaactagtaa aaaataagca    6720
aagaaattag gcgaacgatg agaattgtcc tcgcttggca aatgcgaatc cgtatggaga    6780
ggcacgtttg gcgaaggcaa atgttcggta tggagatctg taaaaatttt taagttgaaa    6840
tttggtgttg ctctttttaca aaattttccg attttcgctt gaaattacgg tgccaggtct   6900
cgacacgtct tccaattttt caaattcaaa agagcccttta atgggctgta gttgctaatt   6960
tctcgttttt gaaaatttttt cttccgttttta atcgaaattt gatgtatttt attttatgatt 7020 ttcaataaat ttcaaagaaa ctggtgaaaa ctcggaaaat tgtgaactac agtaatccaa    7080
tccttaaagg cgcacacctt ttaaatgtcc gccccaatac gatatttttt taagattcgc    7140
tagagcggcc gccaccgcgg tggagctcca attcgcccta gtgagtcg tattacaatt     7200 cactggccgt cgttttacaa cgtcgtgact gggaaaaccc tggcgttacc caacttaatc   7260
gccttgcagc acatccccccc ttcgccagct ggcgtaatag cgaagaggcc cgcaccgatc  7320 gccctttccca acagttgcgt agcctgaatg gcgaatggga cgcgccctgt agcggcgcat   7380
taagcgcggg gggtgtggtg gttacgcgca gcgtgaccgc tacacttgcc agcgccctag    7440
cgcccgctcc tttcgctttc ttcccttcct ttctcgccac gttcgccggc tttccccgtc    7500
aagctctaaa tcggggggctc cctttagggt tccgatttag tgcttacgg cacctcgacc    7560 ccaaaaaact tgattagggt gatggttcac gtagtgggcc atcgccctga tagacggttt    7620
```

```
ttcgcccttt gacgttggag tccacgttct ttaatagtgg actcttgttc caaactggaa    7680
caacactcaa ccctatctcg gtctattctt ttgatttata agggattttg ccgatttcgg    7740
cctattggtt aaaaaatgag ctgatttaac aaaaatttaa cgcgaatttt aacaaaatat    7800
taacgtttac aatttcaggt ggcacttttc ggggaaatgt gcgcggaacc cctatttgtt    7860
tattttctta aatacattca aatatgtatc cgctcatgag acaataaccc tgataaatgc    7920
ttcaataata ttgaaaaagg aagagtatga gtattcaaca tttccgtgtc gcccttattc    7980
ccttttttgc ggcattttgc cttcctgttt ttgctcaccc agaaacgctg gtgaaagtaa    8040
aagatgctga agatcagttg ggtgcacgag tgggttacat cgaactggat ctcaacagcg    8100
gtaagatcct tgagagtttt cgccccgaag aacgttttcc aatgatgagc acttttaaag    8160
ttctgctatg tggcgcggta ttcccgta ttgacgccgg gcaagagcaa ctcggtcgcc    8220
gcatacacta ttctcagaat gacttggttg agtactcacc agtcacagaa aagcatctta    8280
cggatggcat gacagtaaga gaattatgca gtgctgccat aagcatgagt gataacactg    8340
cggccaactt acttctgaca acgatcggag gaccgaagga gctaaccgct ttttttcaca    8400
acatggggga tcatgtaact cgccttgatc gttgggaacc ggagctgaat gaagccatac    8460
caaacgacga gcgtgacacc acgatgcctg tagcaatggc aacaacgttg cgcaaactat    8520
taactggcga actacttact ctagcttccc ggcaacaatt aatagactgg atggaggcgg    8580
ataaagttgc aggaccactt ctgcgctcgg cccttccggc tggctggttt attgctgata    8640
aatctggagc cggtgagcgt gggtctcgcg gtatcattgc agcactgggg ccagatggta    8700
agccctcccg tatcgtagtt atctacacga cgggcagtca ggcaactatg gatgaacgaa    8760
atagacagat cgctgagata ggtgcctcac tgattaagca ttggtaactg tcagaccaag    8820
tttactcata tatactttag attgatttaa aacttcattt ttaatttaaa aggatctagg    8880
tgaagatcct ttttgataat ctcatgacca aaatccctta acgtgagttt cgttccact    8940 gagcgtcaga ccccgtagaa aagatcaaag gatcttcttg agatcctttt tttctgcgcg    9000
taatctgctg cttgcaaaca aaaaaaccac cgctaccagc ggtggtttgt ttgccggatc    9060
aagagctacc aactctttt ccgaaggtaa ctggcttcag cagagcgcag ataccaaata    9120
ctgtccttct agtgtagccg tagttaggcc accacttcaa gaactctgta gcaccgccta    9180
catacctcgc tctgctaatc ctgttaccag tggctgctgc cagtggcgat aagtcgtgtc    9240
ttaccgggtt ggactcaaga cgatagttac cggataaggc gcagcggtcg ggctgaacgg    9300
ggggttcgtg cacacagccc agcttggagc gaacgaccta caccgaactg agatacctac    9360
agcgtgagca ttgagaaagc gccacgcttc ccgaagggag aaaggcggac aggtatccgg    9420
taagcggcag ggtcggaaca ggagagcgca cgagggagct tccagggggg aacgcctggt    9480
atctttatag tcctgtcggg tttcgccacc tctgacttga gcgtcgattt ttgtgatgct    9540
cgtcaggggg gccgagccta tggaaaaacg ccagcaacgc ggccttttta cggttcctgg    9600
ccttttgctg gccttttgct cacatgttct ttcctgcgtt atcccctgat tctgtggata    9660
accgtattac cgcctttgag tgagctgata ccgctcgccg cagccgaacg accgagcgca    9720
gcgagtcagt gagcgaggaa gcggaagagc gcccaatacg caaaccgcct ctccccgcgc    9780
gttggccgat tcattaatgc agctggcacg acaggtttcc cgactggaaa gcgggcagtg    9840
agcgcaacgc aattaatgtg agttacctca ctcattaggc accccaggct ttacacttta    9900
tgcttccggc tcctatgttg tgtggaattg tgagcggata acaatttcac acaggaaaca    9960
gctatgacca tgattacgcc aagctcggaa ttaaccctca ctaaagggaa caaaagctgg   10020
```

```
gggggatcct ccaaaatcgt cttccgctct gaaaaacgaa agtggacctt tgacatccga    10080
aaaaatgggc gaaaaaatga aattgagctt tttgggtcga aaaaaatgtt tttagaatgc    10140
tgagaacacg ttaaacacga agatcatatt tattttgaga cccggatgct ctgaaaatgt    10200
ctgacataga tttaaaaaag catatatata tttttcattt tcaacgtgaa agttttgtgc    10260
aactttatag aatctcctat tggcacattg ttttttattt aactgaggca gttttttgaac   10320 accttttga aactttgaat ctcttgaag tatactgtcg aaaagactga cttgagcgtt     10380
cgaaatgcca gaagaaaact atatttgaat ctcgcgctaa attgagaaat gcaaccgcgc    10440
tccactggac aattggaaaa aaaatttatt cggaggcgac aacggtattt tcgaaattga    10500
ttttctgtgt attttctcat ttttttataaa ttcttctttg atttatcgtt cgtttgtgag   10560
aaatttaatt gtattcaaac ttttttatag taagata                             10597

<210> SEQ ID NO 11
<211> LENGTH: 10599
<212> TYPE: DNA
<213> ORGANISM: Artificial Sequence
<220> FEATURE:
<223> OTHER INFORMATION: Description of Artificial Sequence:plasmid DNA

<400> SEQUENCE: 11
ccggtggtac cgctagccgt acgaacccgg gttctagaac tagtggatcc cacttgagat      60
caacatgatc agaatcccaa tcagttggct ctggacgacc tggtctatct ggacgatcaa    120
atggattttt agccaaaata tcggtttcag tttccaatgg atcagaaggt ccttcgctgt    180
tgacagcctt gacacggaac ttgtaatgat ctcccttgtt gagtgaatcg actgtgaagt    240
gggtatctcc actacgtcca catggaaccc agattccgtc cttggtgttc atcttttcaa    300
tttcatagaa ctcaattggc tctcctccgt catcctctgg tggtttccag tcaagagttg    360
cacgatcttc gaagacatca gttacctcga ttggtcccct tggtttcgtt ggcttgcttt    420
ttaccttgat attgatagtg acactgtcag ttccattaat gttggttgca gtgatggtat    480 atttccact ttgcttacga agtgcctttg gcaaagcaaa tctcgagatg tatggctcat     540
tttcaatttg agccttgctc tctccgattc cttttccatt gaatgaccat gttacatctg    600
gtgctggctc accatcaata tgaacaatga acttgagagt ggctccgacc ttgacagttg    660
tatcagaaag atcttcacga tgaattcttg gagcaaggtt tcttggcttc gcaacaacac    720
gatcagaagg atcagaagga tctccagttc cagccttgtt acgagcagaa attctgaatt    780
gatattcttc tccctcctta agatttggaa cagttgctgt tttctgatct cctgaacaa     840 cgagagcttc ttcccatcgt ccattcttat ccttcttttc aatgacgaaa gcttatcgat    900
accgtcgacc tcgagggggg gccctcgtcg agtcggtcac aatcacctga aactccaaag    960
gcagccagtg aggaacgtga agaagaagaa aaagagtcat ctgaacaggt ttgattttct   1020
ttctggtcaa aaagatgaaa ttattgattt tcagccagat actcccaaaa ctagcagcga    1080
gaagtctgca agtcgttcac agtcgcccag agaatcgcgg gaagtgagcc aagaggtatg    1140 ttttttcaaaa atcaataact gatcataatt tttattgttt ggtgaattta agaaaataat   1200
attcgaaaat tcctctgaat tatcaagatt gcagtattaa tttcgagaaa aattgagata    1260
ttcatagagc tattgtaaat tttcttgatt tcagactgaa acttcggaaa atcaagaaa     1320 aatcaaagaa aaggatgacg gggatgatca gcctggcaca ccgaacagct atagaagccg    1380
ggaaacttca ccagctccaa aaaggtccaa ggagaccagg tttgtcaaaa gcttcctgcg    1440
attaattctc atttcaattt ttcagagaat cagagtctcc tgaaaaatcc ccggttcgtt    1500
```

-continued

```
caagatctcc cagaaggtct tcagcacgtt ccccgtcacg atctcctaga cggcgccgag   1560
aaagaagctc agaaagaaag caatccgaag agccagcacc gctaccagag aaaaagaaga   1620
aagagccgct ggatattcta cgaacaagaa ccggaggagc atatattcca cccgccaaac   1680
ttcgacttat gcaacaacag attagtgata agcaaagtga acagtatcag agaatgaatt   1740
gggaaagaat gaagaaaaag attcacggat tggttaacag agtcaacgcg aagaatcttg   1800
ttcaaattgt cagagaactt cttcaagaga atgtgattcg ttcaaagtga gtgagaaaat   1860
cgaaggaaaa ggaaagaatt aatttaattt ttcaggggac ttctctgccg tgacattatt   1920
caagctcagg ctttctcacc aggattctct aacgtctatg cagctttggc ggcagttatc   1980
aactcgaaat tccctcatgt cggtgaactt cttctccgtc gtctgattgt acagttcaaa   2040
agaagtttcc gtagaaatga cagaggcgtc acggtgaacg tgatcaaatt catcgcacat   2100
ttgattaatc aacaagttgc tcacgaagtt cttgcgctgg aaatcatgat tctgatgctt   2160
gaagaaccaa ctgatgattc agttgaagtc gccattgcgt tcctgaaaga gtgtggagca   2220
aagcttctgg agattgctcc agcagctctt aacagtgtct acgaccgtct tcgtgcaatt   2280
ctcatggaaa ctgaaagatc ggaaaatgca ctggatcgac gtattcagta tatgattgag   2340
actgcaatgc agattcgaaa ggacaaattt gcggtaaggt agaatatata aatagtttat   2400
tagaaaaaaa taaattagaa taatttaaat tcctactagc caatcaggcg accttttgc    2460 gcatagttct attattgaaa aatttggaga atttctcata ttctcgctcg gaaatctgga   2520
attcgacgag atcttctggc ttctgtgcag ctgcatcgct ttgtgctccc tttctcgctt   2580
gtcttctgtg tacaccaaga accttgttga gttcatcaac tgaatctgtg actggcttgt   2640
tgctcactgg atgcactaga cgactgattc tcgagaaatc agattgagtt gcgattaggg   2700
tgacctagaa attgggaata atacgaactt ttgaaaatat tcaggaggat taaaaaaatt   2760
attctcgaca atcctacaaa tttacttatt gcaccatgtt gctccaacat ttttcattaa   2820
aagttaatga aaaaatgtag aaaatcggaa attggcaatt ttcagaccat ttttaagcat   2880
tttcaaaaaa aaattgcagc tgaaataaat gtcattttca gataaatcga gcgattttct   2940
gttgtctgac actagttttt agttttaaaa aatgttggaa gaacatggtg caataggtaa   3000
tttcatagaa tttccatgtg ttttttttca attaaccaat tatccaaatc ttccaaactc   3060
acattttgcg gagctgggct atcaagaatc tgctgcagtt ttataagacg agcatctctg   3120
atatcactga aaattaattt ttaatcaaaa cttgaatatc aactaaaccc acttattaac   3180
tttctcgatc ttctgtcgtt cggtacgatg acggtgaaga agccaattgt agtagttgat   3240
ttggttcaag tcctttcggt gttgtacgtc agtgtcctgc aatgctattt agttataact   3300
taggcctaag attcaattta atgaagtgat taaatttgtt ctctgaacct cttaagatga   3360
tcttttggat tagaaacata taagacaggt ttacctatct attaaaaaac agatcaaaat   3420
agatacgacc aaatcggata atccatgcct acctggcatc taggaacgtg ttcttagaag   3480
atttcttacg taatcgtatg aagaaataac aatttgatcg ttggccagca aaaatagggt   3540
tttaagtggg atagtgtttt tattagctaa ccggaaaatt ttatagtttt tttttgcaag   3600
aaaccactga aaaccccta attgtataca ttttttggag cagcttctgg tcttttttgag  3660 caataaaatt cgataaaaca gaatttaagt gtaaattgtt cacatttagt ttctatttta   3720
tcaaattttg ttgctcaaaa acattcgaag ctgctctaaa aaaatgcatt aaaaaagggg   3780
ttttcagtgg ttttttcacat taaaaaagct aatttttaact aaaaatccat catatttcca   3840
actttgtcac aacaataaaa tgctggtcaa aatgtgttcg aaaaaatgtt ttttttttta   3900
```

```
attttttataa tttaaaaata gttttctttc gctgggacac atacatttt  gggcgtaaat   3960
tttcagttca aatttccatt tttacaacca taatcataaa gctacgtctg atctctctcg   4020
cacttacctg cgcctgattc gaaagaacaa ccgtagccaa agaacaaga agaacaagca    4080
cgtagttgtg gtagtggacg ttcatcacgc aatactgacc aatggtcgtg gggtctcact   4140
ttccgtacta ttgagagagg ggagactgaa gatggcaatt gaggacagtg tcttcgacgc   4200
acgcatgcat ccataagcat aatccaggag ggatggagag aaaaatcttg tttctaagcc   4260
cctccctttg taatacatac acatatctaa taccgaagaa tggctaattg aatggacgtc   4320
agctgttgct gtagttgcca aggcatcatc gatgaaataa ctgaaagaaa gaattaaata   4380
attattgcag gcgtatccgg cggtcattga agacttggac ttgattgagg aggaggatca   4440
gatcatccat acacttaatt tggaggatgc ggttgatccg gaaaatgggc ttagtaagtg   4500
actgaccaca cgcgggggc attaatttaa taaattgaat tccatttcag atgtgttcaa    4560
actagatcca gaattcgaaa agaacgagga ggtttatgag gagatccgta aggaaatcat   4620
tggaaacgcc gatatttcgg atgaggatgg tggcgacgag ttggatgatg aagaagaggg   4680
tagtgatgtg gaagaggctc cgaagaagac tacagagatt attgataata ctgatcagaa   4740
ttgactgctt tcagaaggta ttcattttga gttttgggcc ggcaaatctg taagttgccg   4800
gttgccgaaa atttgctgaa tttgccggaa aaaaaaattc cggaatttat ttaaaaactt   4860
tttgtaaaaa ttaaattaaa tttgcaactt ttcagagaag tctacctgac aatgcaatca   4920
tctttggact accaagaagc tgctcacaaa ttgctgaaaa tgaagattcc agacagcatg   4980
caggtcagcg atgttgcaaa gaaaaatttt cgaccaaaaa aaccaaccaa tcataaaatt   5040
taaaaaaaaa ctccgttttt ttcttttttt ttatacgaga aaaaccaaaa aaatgtattt   5100
ttgccaaatt ctaaaatact atccccgaaa ttttcaatat tttctctttc agaacgaact   5160
ctgcgcgatg cttgtcgatt gttgtgctca acagcgtacc tacgagcgat tctacggaat   5220
gctcatcgaa cgtttctgcc gacttcgcct cgaataccag caatactttg aaaagctctg   5280
ccaggacacg tattccacga ttcaccgaat tgacatcaca aaactgcgga atttggctcg   5340
ccttattgct catttgctct cgacggatgc tattgactgg aagattttgg ccgatatgaa   5400
aatgaccgaa gaggacacaa cttcttctgg cagaatctat attaaatata tatttaatga   5460
acttgtggag gcgatgggaa tggttaaact tcattcgaga gttactgatc cgtgagtttc   5520
ctagagagag ttgttttcgt attcaatttt ccctattttc agaactttgg ctcattgctt   5580
tgttggatta ttcccacgaa ctaatccgaa cagcgcacga ttttcgatca acttcttcac   5640
aatgattgga ttgggtggtt tgacgttgga acttcgtgaa tggctggcaa agggtctcaa   5700
gaagaagaag ggaatgctgg atcagttgaa ggccgaatca agctcagatt catcgtcgtc   5760
ttcggattcg tcagactcgt ctgattcttc ggattctgac gattcatccg actcgtcttc   5820
agattcctca tcttcttcag aatcagagcc agaaccaccg aagaaaaaga agaagaagaa   5880
cagtgaagag agttccaaaa agaaggaaaa agagaatatt ggtcgacggg atcgtggaga   5940
caagagagct gaacgtcatc gtgatcaaag tgtggagaac aaggacaagg atcgtcgacg   6000
tcgccaggat tctgacgaaa atcgtcggcc agaacgagga gatgaccgca aggatcggag   6060
taaagatcgt cgtcgtcaag actcggatga tgaggatcgg aaaggtcgtg aacgtcggga   6120
agattcaggg gaaagacgtc gcggagatcg ggatcgacgt gatcgaaaca aggatcagga   6180
ggatcaccgt gaagatcgcc gtgaccgaag caaggatcgt gaggatcgac gtgatcgccg   6240
tcgtcatgac tctgatgatg atcgtaaaac tcgtcgggat agaagtgaag agcgaggagg   6300
```

```
acgtcgtcgt gaagtggaat cggatgatcg acgccgacgt cgttgaattt tcaaatttta    6360
aatactgaat atttgttttt tttcctatta tttatttatt ctctttgtgt ttttttttctt   6420 gctttctaaa aaattaattc aatccaaatc taaacatgag cggttttttt tctctttccg    6480
tctcccaatt cgtattccgc tcctctcatc tgaacacaat gtgcaagttt atttatcttc    6540
tcgctttcat ttcattagga cgtgggggga attggtggaa ggggaaaca cacaaaagga     6600 tgatggaaat gaaataagga cacacaatat gcaacaacat tcaattcaga aatatggagg    6660
aaggtttaaa agaaaacata aaatatata gaggaggaag gaaaactagt aaaaaataag     6720
caaagaaatt aggcgaacga tgagaattgt cctcgcttgg caaatgcgaa tccgtatgga    6780
gaggcacgtt tggcgaaggc aaatgttcgg tatggagatc tgtaaaaatt tttaagttga    6840
aatttggtgt tgctctttta caaaattttc cgattttcgc ttgaaattac ggtgccaggt    6900
ctcgacacgt cttccaattt ttcaaattca aaagagcctt taatgggctg tagttgctaa    6960
tttctcgttt ttgaaaattt ttcttccgtt taatcgaaat ttgatgtatt ttatttatga    7020
ttttcaataa atttcaaaga aactggtgaa aactcggaaa attgtgaact acagtaatcc    7080
aatccttaaa ggcgcacacc ttttaaatgt ccgccccaat acgatatttt tttaagattc    7140
gctagagcgg ccgccaccgc ggtggagctc caattcgccc tatagtgagt cgtattacaa    7200
ttcactggcc gtcgttttac aacgtcgtga ctgggaaaac cctggcgtta cccaacttaa    7260
tcgccttgca gcacatcccc ccttcgccag ctggcgtaat agcgaagagg cccgcaccga    7320
tcgcccttcc caacagttgc gtagcctgaa tggcgaatgg gacgcgccct gtagcggcgc    7380
attaagcgcg gcgggtgtgg tggttacgcg cagcgtgacc gctacacttg ccagcgccct    7440
agcgcccgct cctttcgctt tcttcccttc ctttctcgcc acgttcgccg gctttccccg    7500
tcaagctcta aatcggggc tccctttagg gttccgattt agtgctttac ggcacctcga    7560
ccccaaaaaa cttgattagg gtgatggttc acgtagtggg ccatcgccct gatagacggt    7620
ttttcgccct ttgacgttgg agtccacgtt ctttaatagt ggactcttgt tccaaactgg    7680
aacaacactc aaccctatct cggtctattc ttttgattta tagggatttt tgccgatttc    7740
ggcctattgg ttaaaaatg agctgattta acaaaaattt aacgcgaatt ttaacaaaat    7800
attaacgttt acaatttcag gtggcacttt tcggggaaat gtgcgcggaa ccccctatttg   7860 tttatttttc taaatacatt caaatatgta tccgctcatg agacaataac cctgataaat    7920
gcttcaataa tattgaaaaa ggaagagtat gagtattcaa catttccgtg tcgcccttat    7980
tccctttttt gcggcatttt gccttcctgt ttttgctcac ccagaaacgc tggtgaaagt    8040
aaaagatgct gaagatcagt tgggtgcacg agtgggttac atcgaactgg atctcaacag   8100
cggtaagatc cttgagagtt ttcgccccga agaacgtttt ccaatgatga gcacttttaa    8160
agttctgcta tgtggcgcgg tattatcccg tattgacgcc gggcaagagc aactcggtcg    8220
ccgcatacac tattctcaga atgacttggt tgagtactca ccagtcacag aaaagcatct    8280 tacgatggc atgacagtaa gagaattatg cagtgctgcc ataagcatga gtgataacac    8340
tgcggccaac ttacttctga caacgatcgg aggaccgaag gagctaaccg ctttttttca   8400
caacatgggg gatcatgtaa ctcgccttga tcgttgggaa ccggagctga atgaagccat    8460
accaaacgac gagcgtgaca ccacgatgcc tgtagcaatg gcaacaacgt tgcgcaaact    8520
attaactggc gaactactta ctctagcttc ccggcaacaa ttaatagact ggatggaggc    8580
ggataaagtt gcaggaccac ttctgcgctc ggcccttccg gctggctggt ttattgctga    8640
taaatctgga gccggtgagc gtgggtctcg cggtatcatt gcagcactgg ggccagatgg    8700
```

```
taagccctcc cgtatcgtag ttatctacac gacgggcagt caggcaacta tggatgaacg    8760
aaatagacag atcgctgaga taggtgcctc actgattaag cattggtaac tgtcagacca    8820
agtttactca tatatacttt agattgattt aaaacttcat ttttaattta aaaggatcta    8880
ggtgaagatc cttttgata atctcatgac caaaatccct taacgtgagt tttcgttcca    8940
ctgagcgtca gacccgtag aaaagatcaa aggatcttct tgagatcctt ttttctgcg     9000 cgtaatctgc tgcttgcaaa caaaaaaacc accgctacca gcggtggttt gtttgccgga    9060
tcaagagcta ccaactcttt ttccgaaggt aactggcttc agcagagcgc agataccaaa    9120
tactgtcctt ctagtgtagc cgtagttagg ccaccacttc aagaactctg tagcaccgcc    9180
tacatacctc gctctgctaa tcctgttacc agtggctgct gccagtggcg ataagtcgtg    9240
tcttaccggg ttggactcaa gacgatagtt accggataag gcgcagcggt cgggctgaac    9300
ggggggttcg tgcacacagc ccagcttgga gcgaacgacc tacaccgaac tgagatacct    9360
acagcgtgag cattgagaaa gcgccacgct cccgaaggg agaaaggcgg acaggtatcc     9420
ggtaagcggc agggtcggaa caggagagcg cacgagggag cttccagggg gaacgcctg     9480 gtatctttat agtcctgtcg ggtttcgcca cctctgactt gagcgtcgat ttttgtgatg    9540
ctcgtcaggg gggccgagcc tatggaaaaa cgccagcaac gcggcctttt tacggttcct    9600
ggccttttgc tggccttttg ctcacatgtt ctttcctgcg ttatccctg attctgtgga     9660 taaccgtatt accgcctttg agtgagctga taccgctcgc cgcagccgaa cgaccgagcg    9720
cagcgagtca gtgagcgagg aagcggaaga gcgcccaata cgcaaaccgc ctctccccgc    9780
gcgttggccg attcattaat gcagctggca cgacaggttt cccgactgga agcgggcag    9840 tgagcgcaac gcaattaatg tgagttacct cactcattag gcaccccagg ctttacactt    9900
tatgcttccg gctcctatgt tgtgtggaat tgtgagcgga taacaatttc acacaggaaa    9960
cagctatgac catgattacg ccaagctcgg aattaaccct cactaaaggg aacaaaagct    10020 ggggggggatc ctccaaaatc gtcttccgct ctgaaaacg aaagtggacc tttgacatcc    10080
gaaaaaatgg gcgaaaaaat gaaattgagc ttttgggtc gaaaaaatg tttttagaat     10140 gctgagaaca cgttaaacac gaagatcata tttatttgga gacccggatg ctctgaaaat    10200
gtctgacata gatttaaaaa agcatatata tattttcat tttcaacgtg aaagttttgt     10260
gcaactttat agaatctcct attggcacat tgttttttat ttaactgagg cagttttga    10320 acacctttt gaaactttga atctctttga agtatactgt cgaaaagact gacttgagcg    10380
ttcgaaatgc cagaagaaaa ctatatttga atctcgcgct aaattgagaa atgcaaccgc    10440
gctccactgg acaattggaa aaaaaattta ttcggaggcg acaacggtat ttcgaaatt     10500 gattttctgt gtatttctc attttttata aattcttctt tgatttatcg ttcgtttgtg    10560
agaaatttaa ttgtattcaa actttttat agtaagata                           10599
```

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: T7 promoter DNA

<400> SEQUENCE: 12
taatacgact cactataggg cga                                            23

<210> SEQ ID NO 13

```
<211> LENGTH: 35
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 13
agctgtaata cgactcacta tagggcgaga agctt                              35

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 14
tcgaaagctt ctcgcataat agtgagtcgt attac                              35

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 15
catggcagga tgaacacgat taacatcgc                                     29

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 16
atggccccat ggttacggga acgcgaagtc cg                                 32

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 17
atggaattct tacgcgaacg cgaagtccg                                     29

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 18
ctcaccggta atgaacacga ttaacatcgc                                    30

<210> SEQ ID NO 19
<211> LENGTH: 12
<212> TYPE: PRT
```

<213> ORGANISM: Simian virus 40

<400> SEQUENCE: 19

Met Thr Ala Pro Lys Lys Lys Arg Lys Val Pro Val
1               5                   10

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 20
gccaccggtg cgagctcatg aacacgatta acatcgc                           37

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 21
cactagtggg cccttacgcg aacgcgaagt ccg                               33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 22
ccggatgact gctccaaaga agaagcgtaa gct                               33

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 23
cccgggatta atacgactca ctata                                       25

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 24
ccggtatagt gagtcgtatt aatcccggga gct                               33

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence:
      oligonucleotide DNA

```
<400> SEQUENCE: 25
aattcttaat acgactcact atagggcc                                              28

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 26
catgggccct atagtgagtc gtattaag                                              28

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 27
gatccgtcga cagatctccc tatagtgagt cgtattactg ca                              42

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 28
gtaatacgac tcactatagg gagatctgtc gacg                                       34

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 29
tatgccctat agtgagtcgt attaag                                                26
```

US 8,114,980 B2

CHARACTERISATION OF GENE FUNCTION USING DOUBLE STRANDED RNA INHIBITION

RELATED APPLICATIONS

This application is a divisional of U.S. patent application Ser. No. 10/057,108, entitled CHARACTERISATION OF GENE FUNCTION USING DOUBLE STRANDED RNA INHIBITION, filed Jan. 25, 2002, now pending; which is a divisional of U.S. patent application Ser. No. 09/347,311, entitled CHARACTERISATION OF GENE FUNCTION USING DOUBLE STRANDED RNA INHIBITION, filed Jul. 2, 1999, and now pending, which is herein incorporated by reference in its entirety.

SUMMARY OF THE INVENTION

The present invention is concerned with characterization or identification of gene function using double stranded RNA inhibition (dsRNAi) and methods of identifying DNA responsible for inducing a specific phenotype in a cell and a method of assigning function to known gene sequences.

It has recently been described in Nature Vol 391, pp.806-811, February 1998, that introducing double stranded RNA into a cell results in potent and specific interference with expression of endogenous genes in the cell and which interference is substantially more effective than providing either RNA strand individually as proposed in antisense technology. This specific reduction of the activity of the gene was also found to occur in the nematode worm *Caenorhabditis elegans* (*C. elegans*) when the RNA was introduced into the genome or body cavity of the worm.

The present inventors have utilized this technique and applied it further to devise novel and inventive methods of assigning functions to genes or DNA fragments, which have been sequenced in various projects, such as, for example, the human genome project and which have yet to be accorded a particular function and for use in identifying DNA responsible for conferring a particular phenotype.

Therefore, according to a first aspect of the present invention there is provided a method of identifying DNA responsible for conferring a phenotype in a cell which method comprises a) constructing a cDNA or genomic library of the DNA of said cell in an orientation relative to a promoter(s) capable of promoting transcription of said cDNA or DNA to double stranded (ds) RNA upon binding of an appropriate transcription factor to said promoter(s), b) introducing said library into one or more of said cells comprising said transcription factor, and c) identifying and isolating a desired phenotype of said cell comprising said library and identifying the DNA or cDNA fragment from said library responsible for conferring said phenotype.

In a preferred embodiment of the invention the library may be organised into hierarchical pools as described in more detail in the examples provided, prior to step b) such as to include, for example, gene families.

According to a further aspect of the invention there is also provided a method of assigning function to a known DNA sequence which method comprises a) identifying a homologue(s) of said DNA in a cell, b) isolating the relevant DNA homologue(s) or a fragment thereof from said cell, c) cloning said homologue or fragment into an appropriate vector in an orientation relative to a promoter(s) capable of promoting transcription of dsRNA upon binding of an appropriate transcription factor to said promoters, d) introducing said vector into said cell from step a) comprising said transcription factor, and e) identifying the phenotype of said cell compared to wild type.

In each aspect of the invention, the nucleotide or DNA sequence may either be provided in a sense and an antisense orientation relative to a single promoter which has the properties defined above, or alternatively it may be provided between two identical promoters. In both embodiments dsRNA is provided from the transcription initiated from the promoter following binding of its appropriate transcription factor.

The cell according to the invention may be derived from or contained in an organism. Where the cell is contained within an organism, the organism may be adapted to express the appropriate transcription factor. The organism may be any of a plant, animal, fungus or yeast but preferably may be the nematode worm *C. elegans*, which may be any of a wild type, a nuc-1 or pha-ts mutant of *C. elegans* or a combination of said mutations. In an alternative embodiment the DNA or cDNA library or the DNA homologue or fragment thereof may, advantageously, be transfected or transformed into a microorganism, such as a bacterial or yeast cell, which may be fed to the organism, which is preferably the nematode worm *C. elegans*. In this embodiment of the invention the microorganism may be adapted to express the appropriate transcription factor. Preferably, the microorganism is *E. coli*.

In each aspect of the invention, the DNA library, DNA homologue or DNA fragment may be constructed in a suitable DNA vector which comprises a sequence of nucleotides which encode said transcription factor. Alternatively, said transcription factor is encoded by a further vector. In an even further alternative, the cell or organism may express or be adapted to express said transcription factor. Preferably, any of the vectors used in the method according to the invention comprises a selectable marker which may be, for example, a nucleotide sequence encoding sup-35 or a fragment thereof. The nucleotide sequence may be orientated relative to a promoter such that binding of a transcription factor to the promoter initiates transcription of the DNA into double stranded RNA. FIG. 10 illustrates the vectors and the orientation of the DNA sequence which enable double stranded RNA production in *C. elegans*. Thus in one embodiment the DNA is located between two promoters on a vector capable of expressing dsRNA upon binding of an appropriate transcription factor to said promoters. Alternatively, the vector comprises two copies of the DNA sequence organised in a sense and antisense orientation relative to the promoter and which marker is selectable when contained in a pha-1 mutant *C. elegans*. Preferably, the promoters are any of T7, T3 or SP6 promoters and the transcription factor comprises the appropriate polymerase.

Preferably, the selectable marker comprises a nucleotide sequence capable of inhibiting or preventing expression of a gene in said cell and which gene is responsible for conferring a known phenotype. This nucleotide sequence may be part of or identical to said gene conferring said phenotype, and which nucleotide sequence is itself oriented relative to a suitable promoter(s) capable of initiating transcription of double stranded RNA upon binding of an appropriate transcription factor to said promoter(s). Alternatively, the nucleotide sequence may be a part of or identical to said gene sequence conferring said phenotype, and which nucleotide sequence is such as to permit integration of said suitable or further vector by homologous recombination in the genome of said cell and following said integration said nucleotide sequence is capable of inhibiting expression of said gene sequence conferring said phenotype. In this embodiment said nucleotide sequence comprises stop codons sufficient to prevent translation of said nucleotide sequence following its integration into said genome.

Compounds can, advantageously, in said method be added to said cell or organism for the purposes of screening for desired phenotypes, such as for example, resistance or sensitivity to the compound when compared to wild type. The promoters are preferably inducible. The transcription factor may in some embodiments be phage derived, such as for example, a T7 polymerase driven by a phage promoter. However, when *C. elegans* is utilised a worm specific or tissue specific promoter can be used, such as for example, let858, SERCA, UL6, myo-2 or myo-3. Preferably, the *E. Coli* strain is an RNAaseIII and even more preferably an Rnase negative strain.

A further aspect of the present invention provides a method of generating a transgenic non-human organism comprising an exogenous transcription factor and a transgene comprising a promoter operably linked to DNA fragment which is expressed upon binding of said transcription factor thereto, the method comprising a) providing a first transgenic organism comprising a first construct incorporating DNA encoding an exogenous transcription factor and a second transgenic organism comprising a second construct including at least one promoter operably linked to a desired DNA sequence which is expressed upon binding of the transcription factor of said first transgenic organism thereto b) crossing said first and second transgenic organisms and selecting offspring expressing said desired DNA sequence. In one embodiment said first and second transgenic organisms are generated by transforming said first and second constructs into respective microorganisms for subsequent feeding to the respective organism. Preferably, said second construct comprises said desired DNA sequence in an orientation relative to said promoter so as to be capable of initiating transcription of said DNA to dsRNA upon binding of said transcription factor thereto. In this embodiment said second construct comprises two promoters flanking said desired DNA sequence which promoters can initiate transcription of said DNA sequence to dsRNA upon binding of said transcription factor to said promoters. Alternatively, said DNA sequence is provided in a sense and an antisense orientation relative to said promoter so as to produce dsRNA upon binding of the transcription factor to the promoters. In each of these embodiments the first and/or second constructs may preferably be provided with a reporter gene operably linked to a promoter which is capable of initiating transcription of said reporter upon binding of said transcription factor thereto. Preferably, the reporter gene encodes any of Luciferase, Green Fluorescent protein, β galactosidase or β-lactamase.

The present invention also includes a method of validating clones identified in yeast two hybrid vector experiments which experiments are well known to those skilled in the art and which experiments were first proposed by Chien et al. (1991) to detect protein—protein interactions. The method according to the invention comprises providing a construct including the DNA encoding a protein identified in a two hybrid vector experiment, which construct is such that said DNA is provided in an orientation relative to one or more promoters capable of promoting transcription of said DNA to double stranded RNA upon binding of an appropriate transcription factor to said promoters, transforming a cell, such as a bacterial cell or alternatively transforming an organism comprising said transcription factor with said constructs and identifying a phenotypic change in said cell or organism, which may be *C. elegans* or the like, compared to wild type. Preferably, the transcription factor is inducible in the cell or organism. Once again the DNA sequence may be located between two promoters or in both a sense and antisense orientation relative to a single promoter, as described above. Preferably, the promoter is a phage polymerase promoter and said transcription factor is a RNA polymerase, and preferably T7 polymerases. Also encompassed with the scope of the present invention are vectors used to transform said cells or organisms and the cells or organisms themselves.

In a further aspect of the present invention there is provided a method of alleviating pest infestation of plants, which method comprises a) identifying a DNA sequence from said pest which is critical either for its survival, growth, proliferation or reproduction, b) cloning said sequence from step a) or a fragment thereof in a suitable vector relative to one or more promoters capable of transcribing said sequence to RNA or dsRNA upon binding of an appropriate transcription factor to said promoters, and c) introducing said vector into the plant.

Thus, advantageously, the method according to the invention provides a particularly selective mechanism for alleviating pest infestation, and in some cases parasitic infestation of plants, such that when the pest feeds on the plant it will digest the expressed dsRNA in the plant thus inhibiting the expression of the DNA within the pest which is critical for its growth, survival, proliferation or reproduction. In a preferred embodiment, the pest may be any of *Tylenchulus* ssp. *Radopholus* ssp., *Rhadinaphelenchus* ssp., *Heterodera* ssp., *Rotylenchulus* ssp., *Pratylenchus* ssp., *Belonolaimus* ssp., *Canjanus* ssp., *Meloidogyne* ssp., *Globodera* ssp., *Nacobbus* ssp., *Ditylenchus* ssp., *Aphelenchoides* ssp., *Hirschmenniella* ssp., *Anguina* ssp., *Hoplolaimus* ssp., *Heliotylenchus* ssp., *Criconemella* ssp., *Xiphinema* ssp., *Longidorus* ssp., *Trichodorus* ssp., *Paratrichodorus* ssp., *Aphelenchs* ssp. The DNA sequence or fragment thereof according to this aspect of the invention may be cloned between two tissue specific promoters, such as two root specific promoters.

A further aspect of the invention concerns the vector used in each of the methods of the invention for constructing said library, which vector comprises two identical promoters oriented such that they are capable of initiating transcription of DNA sequence located between said promoters to dsRNA upon binding of an appropriate transcription factor to said promoters. The DNA sequence may, for example, include a multiple cloning site. Preferably, the expression vector comprises a nucleotide sequence encoding a selectable marker. In one embodiment the nucleotide sequence encoding said selectable marker is located between two identical promoters oriented such that they are capable of initiating transcription of DNA located between said promoters to double stranded RNA upon binding of an appropriate transcription factor to said promoters. Preferably, the selectable marker comprises a nucleotide sequence encoding sup-35, for introduction into *C. elegans* having a pha-1 mutation.

Preferably, the transcription factor comprises either a phage polymerase which binds to its corresponding promoter or a *C. elegans* specific promoter and even more preferably T7 polymerase. Preferably, the vector includes a multiple cloning site between said identical promoters.

In a further aspect of the invention there is provided an expression vector for expressing an appropriate transcription factor for use in a method according to the invention which vector comprises a sequence of nucleotides encoding said transcription factor operably linked to suitable expression control sequences. Preferably, the expression control sequences include promoters which are inducible, constitutive, general or tissue specific promoters, or combinations thereof. Preferably, the transcription factor comprises a phage polymerase, and preferably T7, T3 or SP6, RNA polymerase.

A further aspect of the invention provides a selection system for identifying transformation of a cell or organism with a vector according to the invention which system comprises a vector according to the invention wherein said selectable marker comprises a nucleotide sequence capable of inhibiting or preventing expression of a gene in said cell or organism which gene is responsible for conferring a known phenotype. Preferably said nucleotide sequence corresponds to a part of or is identical to said gene conferring said known phenotype, and which nucleotide sequence is itself located between two identical promoters capable of initiating transcription of double stranded RNA upon binding of an appropriate transcription factor thereto. Alternatively, the nucleotide sequence comprises a nucleotide sequence which is a part of or identical to said gene sequence which confers a known phenotype on said cell or organism, and which is such that following integration of said vector by homologous recombination in the chromosome of said cell or organism said sequence inhibits expression of said gene sequence conferring said known phenotype. Preferably, according to this embodiment the nucleotide sequence comprises stop codons sufficient to prevent translation of the-nucleotide sequence following integration into said chromosome. Preferably, the known gene sequence comprises a sup-35 gene or a fragment thereof which is selectable by identifying offspring growing at a temperature above 25° C. following introduction in a pha-1 et123ts mutant *C. elegans* worm.

In a further aspect of the invention provides said known gene sequence comprises a sup-35 gene or a fragment thereof which is selectable by identifying offspring growing at a temperature above 25° C. following introduction of said vector in a pha-1 et123ts mutant *C. elegans* worm. An even further aspect comprises a method of assigning function to a DNA sequence of a multicellular organism which method comprises a) providing i) a construct comprising said DNA fragment cloned between two promoters capable of promoting transcription in said multicellular organism, in a multicellular organism capable of initiating transcription from said promoter; b) identifying the phenotype of said multicellular organism compared to wild type.

BRIEF DESCRIPTION OF THE DRAWINGS

The present invention may be more clearly understood by the following examples which are purely exemplary with reference to the accompanying figures, wherein:

FIG. 1 is a nucleotide sequence of plasmid pGN1 (SEQ ID NO:1) in accordance with the present invention.

FIG. 2 is a nucleotide sequence of plasmid pGN100 (SEQ ID NO:2) in accordance with the present invention.

FIG. 9 is an illustration of the position of a DNA sequence(s) relative to a suitable promoter to initiate expression of dsRNA from the DNA sequence(s).

FIG. 19(*a*) is a representation of plasmid pGN205 and FIG. 19(*b*) is a representation of plasmid pGN207.

EXAMPLE A

Figure 3:
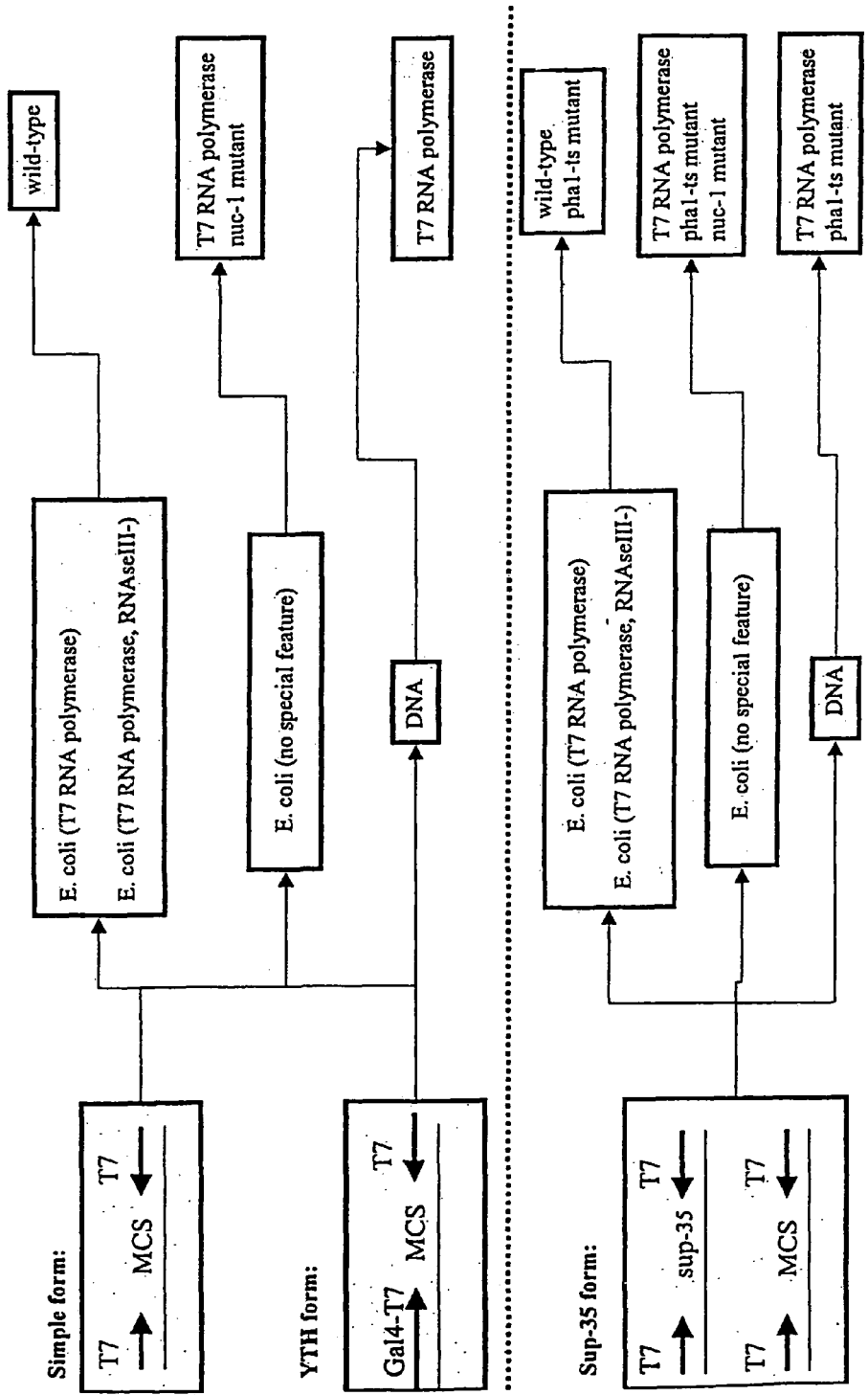
FIG. 3 is a schematic representation of the vectors used and the transformation regime used in the methods according to the present invention.
Figure 4:
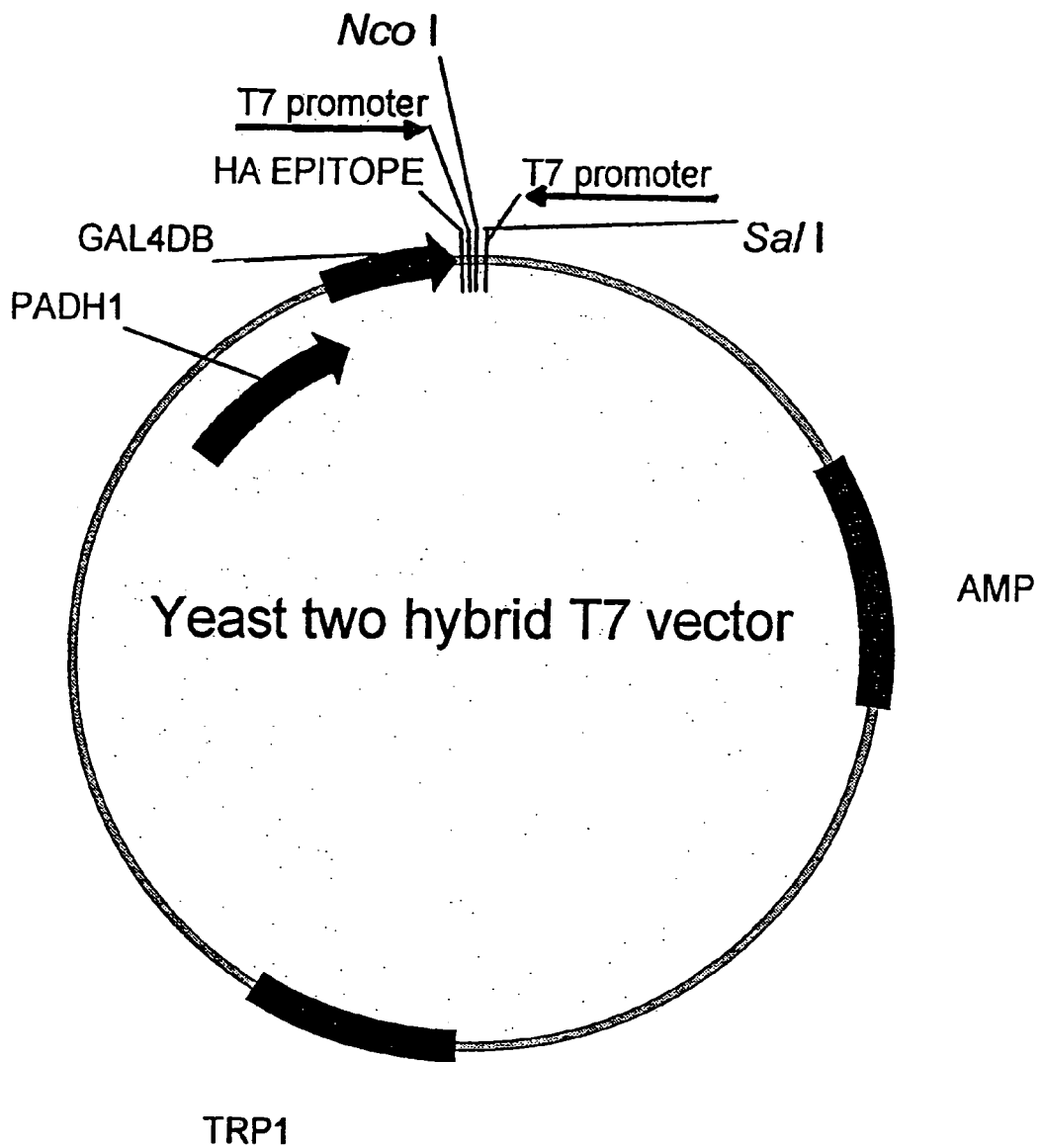
FIG. 4 is an illustration of an expression vector used in accordance with the invention.
Figure 5:
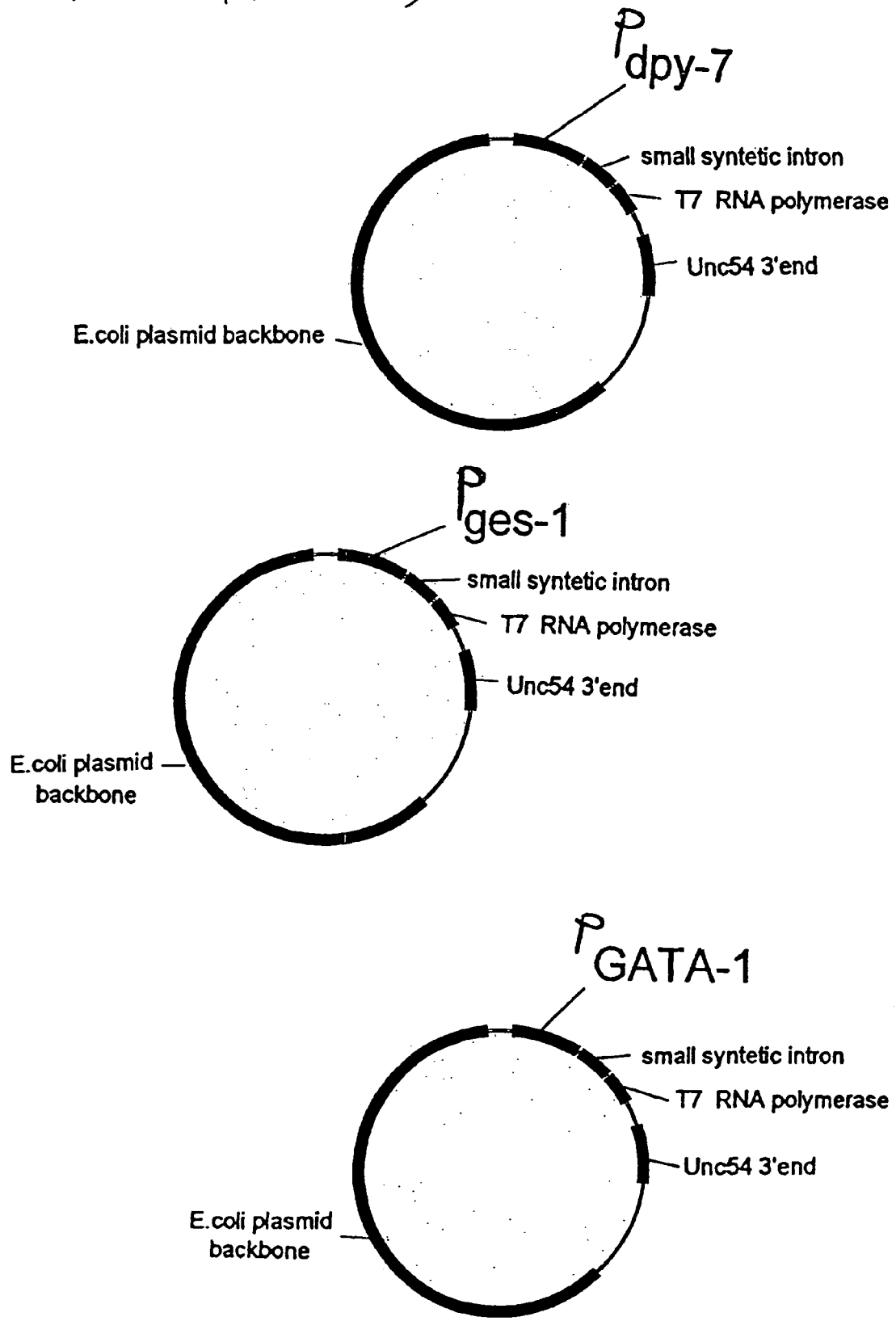
FIG. 5 is a schematic illustration of the T7 RNA polymerase expression vectors used for transforming *C. elegans*.
Figure 6:
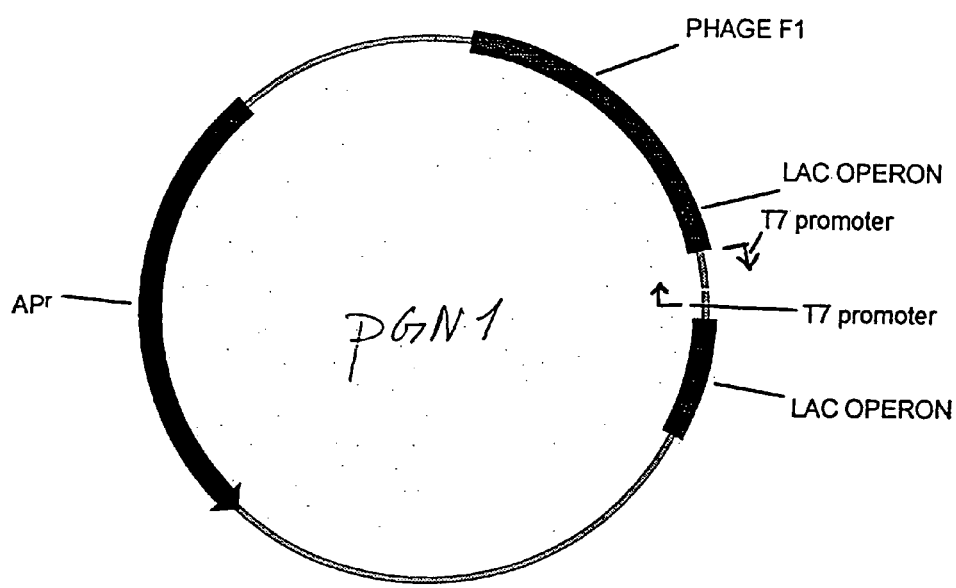
FIG. 6 is an illustration of plasmid pGN1.
Figure 7:
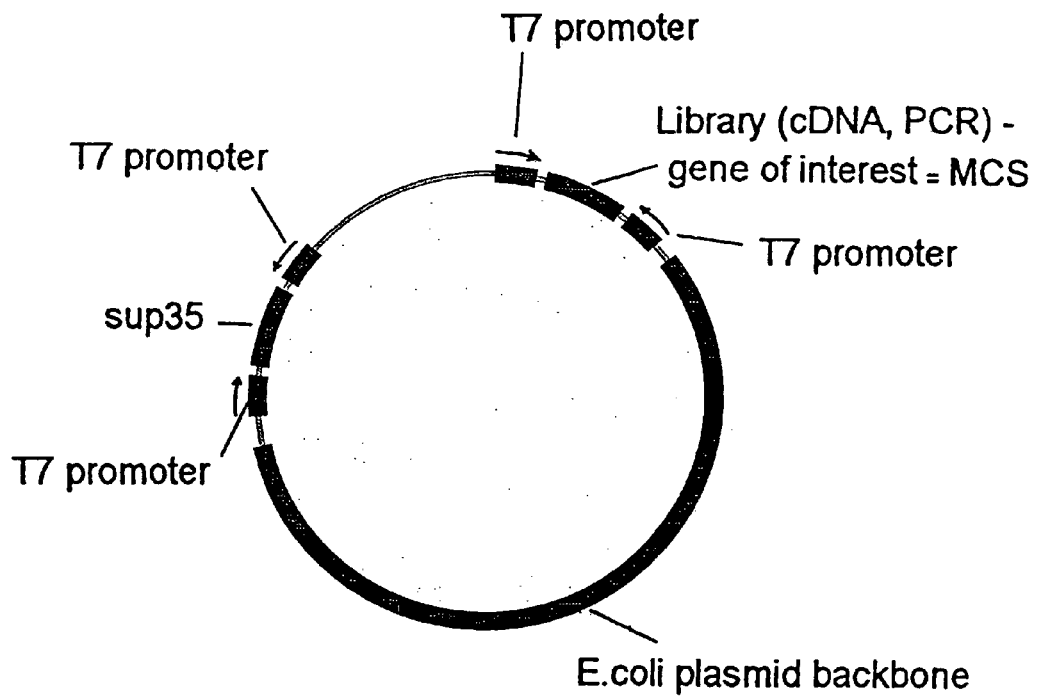
FIG. 7 is a diagrammatic representation of an enhanced vector for dsRNA inhibition encoding sup-35 dsRNA.

Construction of an Ordered and Hierarchical Pooled cDNA Library and Applications Thereof A Random Ordered and Pooled Library:

The vector is an *E. coli* vector harboring two T7 promoters, with a multiple cloning site (MCS) in between. The two promoters are orientated towards each other, and towards the MCS. In the presence of T7 RNA polymerase, expressed in *E. coli, C. elegans* or any other organism, RNA will be produced, starting from the two T7 promoters. As these are oriented in the opposite sense, both strands of RNA will be produced from the DNA inserted (cloned) into the MCS in between the two promoters which results in the generation of double stranded RNA (dsRNA) upon binding of the T7 RNA polymerase thereto.

A *C. elegans* cDNA library is constructed in the MCS using standard molecular biological techniques. The library is transformed into *E. coli* and the resulting *E. coli* are grown in culture and stored in 96 multi-well plates. At this stage, plasmid DNA can be isolated and stored in 96-multi-well plates corresponding to those of the *E. coli* colonies. Approximately 100,000 colonies are scored. In this way, the library will harbor approximately 5 times the total expressed cDNA variation of *C. elegans*, which gives the opportunity for low expressed sequences to be present in the library. This will result in approximately 1041 96-well plates. The plates are hierarchical pooled as necessary. For the present pooling of the clones is arranged in a range of 10 to 100. If the hierarchical pooling is per 8 or 12 (numbers are more convenient: as 96-well plates have a 8 to 12 grid), this will result in approximately 87 multi-well plates and approximately 8352 wells. If hierarchical pooling is per 96 wells, which is a full plate, this results in approximately 111 plates and approximately 1041 wells. At any stage of the hierarchical pooling, plasmid DNA can be isolated, which would be less elaborate as less plates are used, but will result in a loss of complexity although this should not be the case in the pooling per 12. The pooling of the DNA can also be carried out with the original DNA.

The experiments below describe how the hierarchical pooling should be performed, both for the DNA and for the *E. coli* library.

An Ordered Library for RNAi Technology, Harboring Every Gene of the *C elegans* Genome, with Applications Thereof As the genome-sequencing project is coming to an end, this information can be used in the application of T7 RNA inhibition technology. Every gene of the *C. elegans* genome can be cloned using PCR technology. In preference, exons will be cloned with a minimal length of 500 bp. If the exons are too small, smaller fragments will be isolated with PCR, or even parts of introns and neighboring exons will be isolated with PCR technology so that at least a sufficient part of the translated region of the gene is cloned. For this, at least 17000 PCR reactions need to be performed. This collection of PCR products will be cloned in a T7 vector as described (two T7 promoters oriented towards each other with a multiple cloning site in between). Every PCR product is cloned independently, or can be used to generate a random library, analogous to the described cDNA library. If every PCR product is cloned individually, the resulting bacteria and plasmid DNA can be pooled in various ways. Firstly, this collection of individually cloned PCR products in the T7 RNAi vector can be pooled randomly, as described in the random library. This poolipg can also be done in a more rational way. For instance, the genes of the C. elegans genome can be analyzed using bioinformatic tools (in silico biology). Various genes of the genome will belong to a gene family, or will have homologues in the genome. These members of the gene family will be pooled, or the members, being homologues will be pooled. In this way the total number of about 17000 clones is reduced to a more useable quantity. This library can be used to screen for phenotypes in the methods according to the invention. The resulting phenotype gives a functional description to the gene or gene family or gene homologues of the C. elegans genome. As the library consists of a part of every gene in the genome, this method enables description of the full genome in functional-phenotypic terms. For this the double stranded RNA (dsRNA) needs to be introduced in the worm. This introduction of clones alone, or pooled clones, being random pooling or rational pooling can be achieved in several ways as described.

Example of a Vector for the Expression of Double Stranded RNAi

Any vector containing a T7 promoter may be used, and which contains a multiple cloning site (there are many commercially available). Primers containing the T7 promoter and a primer with the reverse complementary strand, both with the appropriate ends are designed. These primers can be hybridized, and if well designed, cloned in the vector of choice. The minimal sequence for a T7 promoter is TAATACGACTCACTATAGGGCGA (SEQ ID NO:12). Although any vector can be used for the construction of a T7 expression vector there follows an example of how to achieve this with the vector pGEM-3zf(−).

Vector pGEM-3zf(+) (PROMEGA) was digested with HindIII and SalI

Primers oGN1 and oGN2 were mixed together at a final concentration of 1 µg/30 µl boiled and cooled slowly to room temperature.

The primer was ligated into the vector using standard ligation procedures. The resulting vector is pGN1 (shown in FIG. 1) and contains two T7 promoters oriented towards each other, and harbors a multiple cloning site in between.

Sequences of oGN1 (SEQ ID NO:13) and oGN2 (SEQ ID NO:14) are:

oGN1: AGC TGT AAT ACG ACT CAC TAT AGG GCG AGA AGC Tf oGN2: TCG AAA GCT TCT CGC ATA ATA GTG AGT CGT ATT AC

Example of the Construction of a Library

RNA may be isolated from every organism that is sensitive to RNAi. In general the isolated RNA is then copied into double stranded cDNA, and subsequently prepared in suitable vectors for cloning. Several procedures exist and molecular biology kits can be purchased from various firms including Promega, Clontech, Boehringer Mannheim, BRL, etc which enable:

isolation of RNA,
eventually polyA RNA can be isolated (several techniques and kits available),
first strand synthesis with AMV reverse transcriptase, random hexameric primers and/or oligo (dT) primer,
second strand synthesis with Rnase H, DNA Polymerase I,
flush ends with T4 DNA Polymerase,
addition of an adaptor with T4 DNA ligase,
eventually treatment with T4 polynucleotide Kinase,
cloning of the cDNA into the vector.

The resulting ligation mixture can be considered as the cDNA library. The ligation contains all cDNA of the procedure ligated into the vector of interest. To order the library, the ligation needs to be transformed into E. coli strains.

Application of this E. coli or DNA Library

T7 RNA producing strain:
a standard strain is BL21 (DE3): F-ompT[Ion]hsds(r- m-; and E. coli B strain)λ (DE3). Eventually variants-of PL21 (DE3) can be used, although BL21 (DE3)pLysS is used.
any other E. coli strain which produces the T7 RNA polymerase, which may be available needs to be constructed. This can be generated easily using a phage, which is commercially available, in this case, the λCE6 vector (provided by Promega) is used. Almost every E. coli strain can be transfected with this phage and will produce T7 RTA polymerase.
a RNAseIII mutant E. coli:
Various strains are in principle available, we chose in a first experiment to use strain AB301-105: ma-19, suc-11, bio-3, gdhA2, his95, rnc-105, relA1, spoT1, metB1. (Kinder et al. 1973 Mol. Gen. Genet 126:53), but other strains may suit better. This strain is infected with λCE6 and so a T7 producing variant will be constructed.

Wild type C. elegans worms can be grown on the bacteria pools. The bacteria is expressing the T7 RNA polymerase. This results in large quantities of dsRNA in the gut of the C. elegans, which will diffuse in the organism and results in the inhibition of expression. This library can now be used for the screening of several phenotypes. This technique has the advantage that it is a much faster to detect relevant genes in certain pathways, than the known C. elegans technology. Moreover, if an interesting phenotype is found, the responsible gene can be cloned easily.

Using the hierarchical pooling one can easily find in a second screen the relevant clone of the pool. The inserted DNA of this clone can then be sequenced. This experiment results in genetic and biochemical DATA in one step.

Wild type C. elegans strains can be combined with compounds to screen for phenotype, drug resistance and or drug sensibility. The C. elegans strain can be a mutant strain, screening for an enhanced phenotype, reduced phenotype, or a new phenotype. The C. elegans strain can be a mutant strain, and the library screen can be combined with compounds. So one can screen for drug resistance, drug sensibility, enhanced phenotype, reduced phenotype, or a new phenotype. The E. coli strain may be any T7 RNA polymerase expressing strain, like BL21 (DE3), for example, but the formation of double strand RNA may be enhanced by using a special E. coli strain that is RNAseIII negative. RNAseIII recognizes specific loops in dsRNA. Eventually, an E. coli strain can be used that is deleted in RNAses other than RNAseIII or an E. coli can be used that is deleted in one or more RNAses. The expression of the T7 RNA polymerase in most known E. coli strains and constructs which are available to generate T7 RNA polymerase producing E. coli strains, generally comprise an inducible promoter. In this way the production of the T7 RNA polymerase is regulated, and thus the production of the dsRNA. Advantageously, this feature can be used to "pulse" feed the *C. elegans* worms at specific stages of growth. The worms are grown on the non-induced *E. coli* strains. When the worm has reached the stage of interest, the T7 RNA production in the bacteria is induced. This allows the studying of the function of any gene at any point in the life cycle of the animal.

Screening the Library for Homologues of Putative Interesting Human Genes, and Assign Function to these Genes Hundreds of genes have been isolated in various projects, being genomic projects, differential expressed arrays, hybridization studies, etc. The described cDNA library can provide a way to validate and or assign function to these genes in a fast and efficient manner. First of all the worm homologue or homologues or the genes need to be identified by bioinformatic tools (in silico biology). PCR primers are developed and the cDNA fragment is isolated using PCR technology. PCR can be performed on the hierarchical pools. The positive pool or individual wells harboring the bacteria that has the appropriate cDNA is fed to *C. elegans* and the phenotype is scored.

PCR can be performed on cDNA isolated from *C. elegans*. The resulting DNA can be cloned in the T7 vector and transformed in the dsRNA producing *E. coli* on which the *C. elegans* worms are then fed. Depending on which way is faster and more reliable a choice needs to be made.

If the gene belongs to a gene family, the worm may need to be fed on a mixture of bacteria, each of them harboring a part of the member of the gene family. *E. coli* strains, growth conditions, combinations with compounds can be performed as described above.

If the library rational is used, in which all the genes of *C. elegans* are cloned in a organized and structured way, the *C. elegans* homologue and eventually the other homologues, orthologues, and members of the gene family can be traced back easily in the library using in silico biology. No PCR is involved in this step, and the bacteria and or DNA can be isolated on which the worm will be grown.

EXAMPLES

The idea of the series of experiments was to test both the RNAi vector and the various *E. coli* strains that were constructed.

1) Construction of a Test Plasmid

Any cDNA that gives a clear phenotype in the worm when knocked-out, or used in a RNAi experiment can be used. It is known that unc-22 is a good candidate, but many other genes are possible. We opted for a sensitive system that can be used at a later stage. The system was tested with sup-35 in a pha-1 background. Exon 5 of the sup-35 was isolated by PCR and cloned in the T7 promoter vector pGN1. The resulting vector was designated pGN2. pha-1 (e2123) mutant worms cannot produce offspring at temperatures higher than 25° C. This is due to a developmental problem in embryogenesis. When sup-35 is knocked-out, or inhibited in this strain, offspring may grow at this temperature. Combination of pha-1 mutant worms and sup-35 RNAi is a good system to validate the various options.

2) Testing the RNAi Using an E. coli Strain that Produces dsRNA.

pGN2 was introduced in *E. coli* strain BL21(DE3) and T7 RNA polymerase was induced with IPTG. *C. elegans* worms (pha-I (e2123)) were inoculated on this bacteria, and grown at the restricted temperature of 25° C. As this mutant is an embryonic mutant at this temperature, no offspring will be observed. If the sup-35 gene is efficiently inhibited by the dsRNA present in the *E. coli*, offspring will be observed.

pGN2 was introduced in *E. coli* strain AB301-105(DE3) and T7 RNA polymerase was induced with IPTG. *C. elegans* worms (pha-1 (e2123)) were inoculated on this bacteria, and grown at the restricted temperature of 25° C. As this mutant is an embryonic mutant at this temperature, no offspring will be observed. If the sup-35 gene is efficiently inhibited by the dsRNA present in the *E. coli*, offspring will be observed.

3) Improving the Worm Strain for Better Uptake of dsRNA.

Before plating the pha-1 *C. elegans* on the *E. coli* strain that produce the double stranded sup-35 RNA. The worm was mutagenised with EMS (Methane sulfonic Acid Ethyl). The offspring of this mutagenised worm is then plated on the bacteria. The worm that feed on this bacteria give larger offspring which has a mutation that results in an improvement of dsRNA uptake, and can be used for further experiments.

Figure 8:
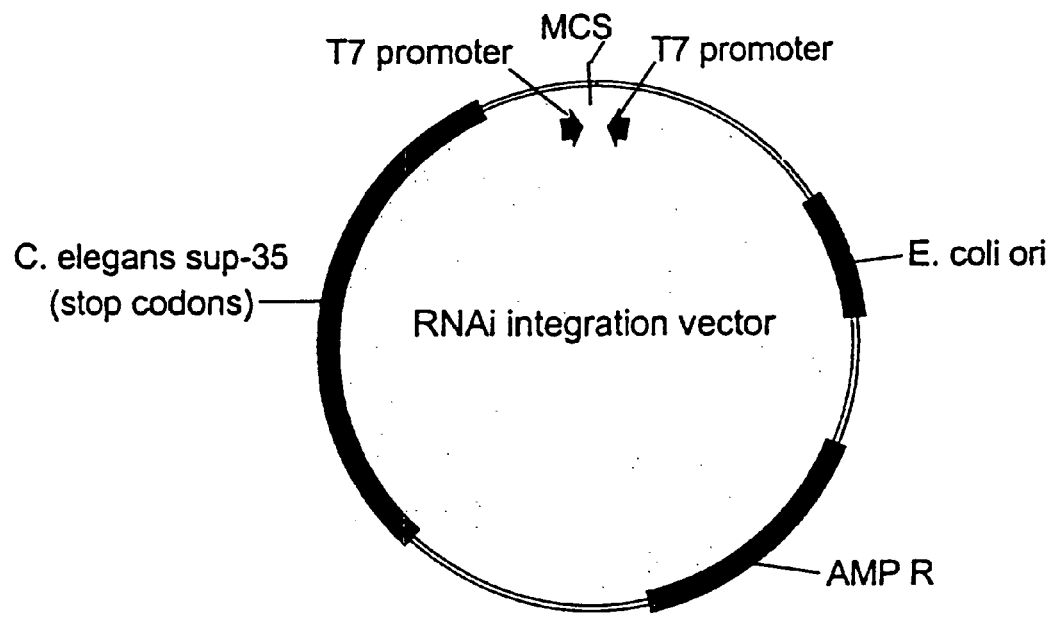
FIG. 8 is an illustration of a vector for integration into the genome of *C. elegans*.

Stable Integration of the dsRNA Producing Vector into the Genome of the T7 RNA Polymerase Producing Worm An *E. coli* vector can be constructed harboring the following features; Two T7 promoters directed towards each other, with a restriction site or a multiple cloning site in between. Furthermore, the vector may contain the *C. elegans* sup35 genomic DNA, engineered in such a way that it contains several stopcodons at various intervals, so that no full length protein can be expressed form the sup35 genomic DNA fragment as illustrated in FIG. 8. Any cDNA or cDNA fragment can be cloned in the multiple cloning site between the two T7 promoters. When this vector is introduced in a *C. elegans* strain which expresses T7 RNA polymerase, the cDNA or DNA fragment cloned between the two T7 promoters will be transcribed, generating dsRNA from the cloned fragment.

The vector is designed to be used in pha-1 (e2123) mutant worms expressing T7 RNA polymerase. The expression of the T7 RNA polymerase may be constitutive or regulated, general or tissue specific. These pha-1 (e2123) worms cannot produce offspring at temperatures higher than 25° C., which is due to a development problem in embryogenesis. When sup-35 is inhibited or knocked-out in this stain, offspring may grow at this temperature.

When the vector is introduced in the worm, the vector may integrate by homologous recombination (Campbell-like integration). It has been shown that homologous recombination occurs in *C. elegans*, although at low frequencies (Plasterk and Groenen, EMBO J. 11:287-290, 1992). Homologous recombination at the sup-35 gene will result in a knock-out of the gene as the two resulting sup-35 genes will harbor the stopcodons. The resulting worm, and its offspring, if this recombination happens in the eggs, will have a copy of the vector integrated in the genome. This can be selected as only the worms for which the sup-35 has been knocked-out will have offspring at temperatures higher than 25° C. Furthermore, the resulting worm will stably produce double stranded RNA from the DNA fragment cloned between the two T7 promoters. This worm can now be considered as a stable transgenic worm strain with a reduction of function of the gene, from which a fragment has been cloned between the two T7 promoters.

The DNA may be delivered to the worm by several techniques, including injection, ballistic transformation, soaking in the DNA solution, feeding with bacteria. New and other methods that increase the transformation efficiencies can be considered.

The target *C. elegans* strain may in addition, have other mutations than the-pha-1 (e2123) mutation, and may express other genes than T7 RNA polymerase.

EXAMPLE B

A Yeast Two-hybrid-RNAi Vector

A yeast two hybrid vector can be constructed harboring the two T7 promoters. The vectors can be designed to replicate both in yeast and in *E. coli*. In general cDNA libraries for the yeast two hybrid system are made in the Gal4 or LexA vectors. The library is constructed in vectors having the activation domain of one of these genes. A vector can be constructed that can still perform in the yeast two hybrid screen but which also contains two T7 promoters orientated towards each other, with a cloning site therein between. The order of the sequences in the plasmid will then be "plasmid backbone, (GAL4-T7), MCS, T7, backbone". A *C. elegans* cDNA library constructed in this vector can be used as a standard yeast two hybrid library in an experiment to isolate interacting proteins with a given protein. Once a clone is isolated, the plasmid can be introduced in an *E. coli* strain expressing the T7 RNA polymerase, and hence will produce dsRNA of the cloned fragment. The bacteria producing this dsRNA can be fed to the worm and phenotypes can be scored. As in the previous example, this validation procedure for a newly isolated yeast two hybrid clone is remarkably shorter than the standard procedure, which requires PCR and/or cloning steps, RNA experiments and/or knock-out experiments. In most cases isolated clones are sequenced first, and on the basis of the sequence, a decision is made to continue with further experiments. In the present invention every isolated clone can easily be introduced into the appropriate *E. coli* and fed to the worm. Validation is then performed by phenotype analysis.

To apply this procedure a yeast two hybrid was performed using a known gene as bait and the newly constructed library as the target. Proteins coded by the clones in the target that interact with the bait protein, will result in positive yeast clones expressing the reporter molecule such as can be observed by LacZ staining with X-gal. The plasmid coding for the target protein is isolated directly from the yeast strain and introduced in *E. coli*. The *E. coli* is T7 RNA polymerase producing *E. coli*. In this case, double stranded RNA is produced from the DNA cloned in the multiple cloning site of the vector. When this dsRNA is fed to the worm using the methods described previously, the gene has inhibited in the worm, resulting in a particular phenotype.

This yeast two hybrid vector can advantageously be used to construct an ordered and hierarchically pooled library as described in the previous example.

A yeast strain can also be constructed that conditionally produces T7 RNA polymerase. After yeast two hybrid experiments, the expression of the T7 polymerase could be induced, resulting in the production of dsRNA in the yeast cell. Consequently the yeast could be fed to the worm. Evidence is available showing that the *C. elegans* worms can feed on yeast.

Construction of a T7 RNA Polymerase Producing Strain, and Applications Thereof

A *C. elegans* strain can be constructed that expresses T7 RNA polymerase. The expression can be general and constitutive, but could also be regulated under a tissue specific promoter, an inducible promoter, or a temporal promoter or a promoter that harbors one of these characteristics or combination of characteristics. DNA can be introduced in this *C. elegans* strain. This is done either by injection, by shooting with particles, by electroporation or as aforementioned by feeding. If the DNA is a plasmid as described in the previous examples, i.e. a plasmid harboring a cloned cDNA fragment or a PCR fragment between two flanking T7 promoters, then dsRNA of this cDNA or PCR fragment is formed in the cell or whole organism resulting in down regulation of the corresponding gene. The introduced DNA can have an efficient transient down regulation. The introduced DNA can form an extrachromosomal array, which array might result in a more catalytic knock-out or reduction of function phenotype. The plasmid might also integrate into the genome of the organism, resulting in the same catalytic knock out or reduction of function phenotype, but which is stably transmittable.

Plasmid DNA harboring a cDNA or a part of a cDNA or an EST or an PCR fragment of *C. elegans* cloned between two T7 promoters as described in Examples A) and B) can be introduced in the T7 RNA polymerase worm, by standard techniques. Phenotypes can be analysed-DNA from an ordered and pooled library as in Example A) can be introduced in the T7 RNA polymerase worm, by standard techniques (injection, shooting). Phenotypes can be analysed. With the hierarchical pool, the original clone can be found easily.

The same procedure can be performed with a mutant worm expressing the T7 RNA polymerase. Screening for enhanced, reduced or new phenotypes.

The procedure can be used to enable screening of compounds. Screening with either a wild-type strain or a mutant strain for enhanced or new phenotypes.

The DNA could be introduced in the worm by new methods. One of which is the delivery of DNA by *E. coli*. In this case the hierarchical pooled library is fed to the animal. To prevent digestion of the *E. coli* DNA in the gut of the nematode, preferentially a DNAse deficient *C. elegans* will be used, such as nuc-1 (e1392). This procedure would be one of the most interesting as it would be independent of transformation efficiencies of other techniques, and generally faster and less labourious.

2) Putative Enhancements of the Method.

A vector is designed, so that it harbors the sup-35 cDNA or a part of this cDNA, cloned in between two T7 promoters. The rest of the vector is as described in Examples A) and B). This vector can be introduced into a pha-its mutant *C. elegans*. A temperature selection system exists in this case and only those worms which have taken up the DNA and express the double stranded sup-35 RNA will survive at restricted temperatures. The hierarchical pooled library can be delivered by any method described above.

The vector can be used to construct a library that is introduced in a T7 RNA polymerase expressing *E. coli*. In this case we have an analogous screening as in part A) with an additional screening for worms where the dsRNA of sup-35 is active.

The DNA and or dsRNA of sup-35 could be delivered on a different plasmid. For the feeding, both DNA feeding (Example C) or dsRNA feeding Example A) and B), this means that the two plasmids could be present in one bacterium, or that the worm is fed on a mixture of bacteria, one of which harbors the sup-35 construct.

Example of the Construction of a T7 RNA Producing *C. elegans*

To produce T7 RNA polymerase in the worm, several possibilities are possible. The T7 polymerase can be expressed under various promoters, being inducible promoters, constitutive promoters, general promoters and tissue (cell) specific promoters, or combinations of those. Examples of these promoters are the heatshock promoter hsp-16, the gut promoter ges 1, the promoter from cet858, but also the promoter of dpy 7 and the promoter element GATA1. In this example the T7 RNA polymerase is expressed under the control of the hsp-16 promoter that is available in the pPD49.78 vector. The T7 RNA polymerase is isolated as a PCR product using the primers of GN3 and GN4.

The resulting PCR product is digested with NheI and NcoI, as is the vector in which we want to clone, being the Fire vector pPD49.78. The resulting vector is pGN100 illustrated in FIG. 2. oGN3 (SEQ ID NO:15): CAT GGC AGG ATG AAC ACG ATT AAC ATC GC; oGN4 (SEQ ID NO:16): ATG GCC CCA TGG TTA CGG GAA CGC GAA GTC CG; pGN100 is included.

The vector is introduced into the worm using standard techniques, such as micro injection, for example.

The following strains were then constructed:
Wild-type (pGN100)
nuc-1 (e 1392) (pGN 100)
pha-1 (e2123) (pGN100)
pha-1; nuc-1 (pGN 100)

All of these strains are able to produce T7 RNA polymerase when temperature induced or alternatively by metals such as application of heavy cadmium or mercury. The procedure for temperature induction is to shift the animal to a temperature of 30-33° C. for at least one hour, then the animal can be shifted back to standard temperatures (15-25° C.).

The wild type strain producing T7 RNA polymerase can be used for the production of any RNA in the worm. More specifically, the plasmids from the described libraries can be introduced in these worms, and phenotypes can be scored.

The nuc-1 mutant worm will be used to introduce DNA via bacteria on which the worm feed. As the nuc-1 worm does not digest the DNA, the plasmid DNA can cross the gut wall. If taken up by the cells that produce the T7 RNA polymerase, dsRNA will be produced thus inhibiting the gene from which the RNA was transcribed.

The pha-1 mutant strain that produced T7 RNA polymerase can be used to enhance the procedures as described above. DNA can be introduced by shooting, micro injection or feeding. More specifically this strain can be used for the vectors that produce dsRNA from sup-35 and from the gene of interest, the latter can be a PCR product, a cDNA, or a library as described.

The pha-1; nuc-1 mutant producing T7 RNA polymerase can be used for the bacterial delivery of the DNA. DNA will preferentially be the plasmid that produce dsRNA from both sup-35 and the gene of interest. The worm strain will preferentially produce the T7 RNA polymerase in the gut. Delivery will preferentially happen by feeding the worm on bacteria harboring the plasmid.

Application of the RNAI Technology in Plants

Nematodes are responsible a large part of the damage inflicted on plants and more particularly to plants used in the agricultural industry. The RNAi procedures according to the invention can be applied to plants to prevent these parasitic nematodes from feeding longer. In a first step, a DNA fragment is isolated from the parasitic plant nematode that is critical for the animals survival or growth, or to feed or to proliferate. Any gene from which the expression is essential is suitable for this purpose.

A part of this gene, an exon or cDNA is cloned. This DNA fragment can be cloned under the influence of a tissue specific promoter preferably a root specific promoter even more preferably between two root specific promoters. The DNA of the cloned gene under the control of the root specific promoter can be introduced in the plant of interest, using plant transgenic technology. For every parasitic nematode, a different piece of DNA may be required and likewise for every plant race, a different promoter will be needed.

The root will produce RNA or dsRNA from the introduced piece of DNA when root specific promoter is utilised. As the nematode feeds on the plant, the RNA and/or dsRNA will be consumed or ingested by the nematode. The RNA and/or dsRNA can enter the cells of the nematode and perform its inhibitory action on the target DNA. Depending on the nature of the cloned DNA piece of worm, the nematode will not be able to survive, to eat, proliferate, etc in any case preventing the animal of feeding longer on the plant, and thus protecting the plant.

Construction of a T7 RNA-polymerase Producing *C. elegans*

To produce a T7 RNA polymerase or other RNA polymerases in animals, and more particularly in nematodes and most particularly in *C. elegans*, several possibilities can be envisaged. The T7 RNA polymerase can be expressed under various promoters. These promoters may be inducible promoters, constitutive promoters, general promoters, tissue specific promoters, or combinations of those.

Example 1

Construction of a Basic Vector for Expression of T7 Polymerase in *C. elegans*

Figure 11:
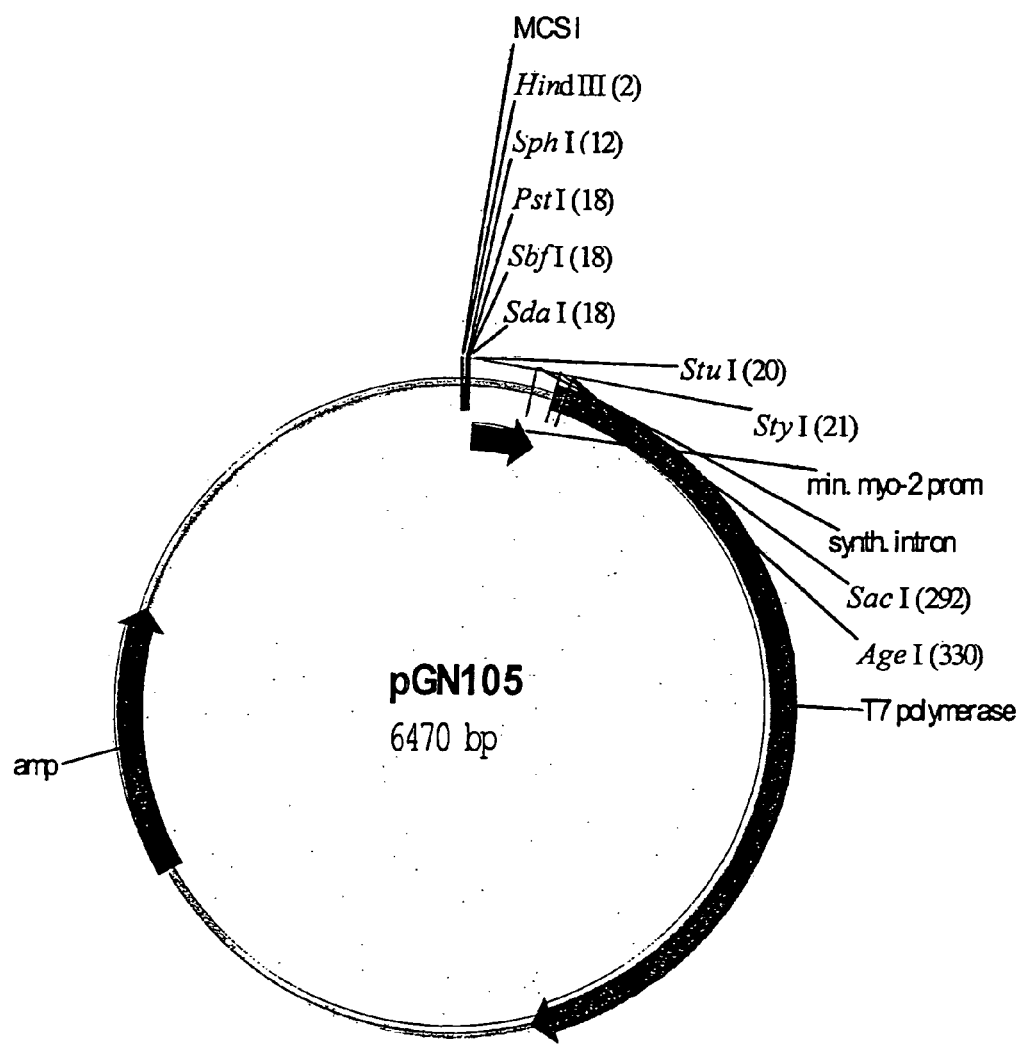
FIG. 11 is a representation of plasmid pGN105.

The T7 polymerase coding sequence was PCR amplified from λCE6 (Novagen, Madison, Wis., USA) using the primers oGN26(ATGGAATTCTTACGCGAACGC-GAAGTCCG; SEQ ID NO:17) and oGN46(CTCACCGG-TAATGAACACGATTAACATCGC; SEQ ID NO:18), using standard procedures (PCR, A practical approach, 1993, Ed. J. McPherson, et al, IRL Press). The resulting DNA fragment encoding for the T7 RNA polymerase was digested with AgeI and EcoRI and inserted into the Fire vector pPD97.82 digested with AgeI and EcoRI. The resulting construct encodes for an open reading frame of T7 RNA polymerase in fusion with the SV40 large T antigen nuclear localization signal (NLS) with amino acid sequence MTAPKKKRKVPV (SEQ ID NO:19). This nuclear localization signal sequence is required to translocate the T7 RNA polymerase from the cytoplasm to the nucleus, where it is able to bind to its specific promoters, designated T7 promoters. Upstream of the coding sequence for the T7 polymerase fusion protein is a minimal promoter (myo-2) preceded by a multiple cloning site (MCS) in-which several *C. elegans* promoters can be inserted. This plasmid (pGN105 shown in FIG. 11) is a basic T7 RNA polymerase plasmid which enables the expression of T7 polymerase in *C. elegans*. Derivatives of this plasmid wherein promoters are cloned into the multiple cloning site, allow for the inducible, constitutive, general and tissue specific expression of T7 RNA polymerase in *C. elegans*, as expression will be regulated by the promoter cloned in the multiple cloning site.

Although not restricted to these examples, for the following promoters it is known that they induce expression in the following tissues: let-858 (ubiquitous expression), myo-2 (pharynx expression), myo-3 (body wall muscles), eg1-15 (vulval muscles), unc-119 (pan-neuron).

Example 2

Figure 10:
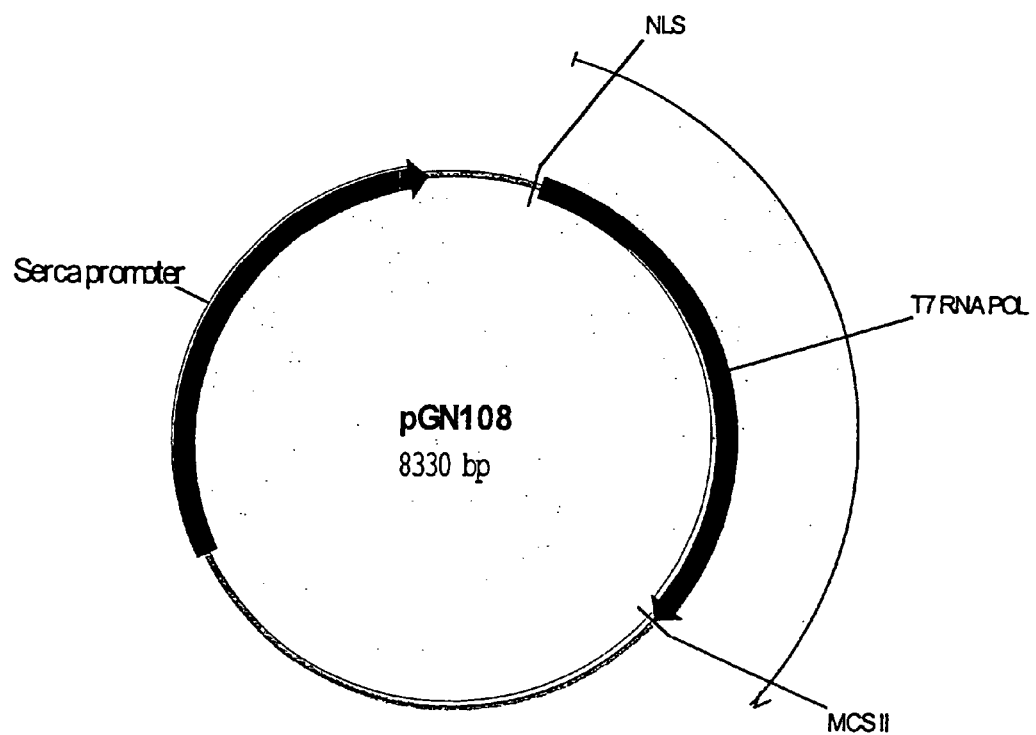
FIG. 10 is a representation of plasmid pGN108.

Construction of a Vector for Expression of T7 RNA Polymerase in *C. elegans* Muscle Tissue The T7 RNA polymerase coding sequence was PCR amplified from λ CE6 using the primers oGN43 (GCCACCGGT- GCGAGCTCATGAACACGATTAACATCGC; SEQ ID NO:20) and oGN44 (CACTAGTGGGCCCTTACGC-GAACGCGAAGTCCG; SEQ ID NO:21) digested with AgeI/SpeI and inserted in the pGKI 3 vector digested with AgeI/SpeI. (This vector contains the strong SERCA promoter which drives expression in the pharynx, the vulval muscle, the tail and the body wall muscle). A nuclear localization signal (NLS) of SV40 large T antigen was inserted in front of the T7 polymerase coding sequence by insertion of two overlapping oligo's oGN45 (CCGGATGACTGCTCCAAAGAA-GAAGCGTAAGCT; SEQ ID NO:22) and oGN46 (CTCAC-CGGTAATGAACACGATTAACATCGC; SEQ ID NO:18) into the SacI/AgeI restriction sites. The resulting construct was called pGN108 as shown in FIG. 10. Introduction of this plasmid into *C. elegans* results in the expression of T7 RNA polymerase in the pharynx, vulva muscle, tail and body wall muscles.

Figure 13:
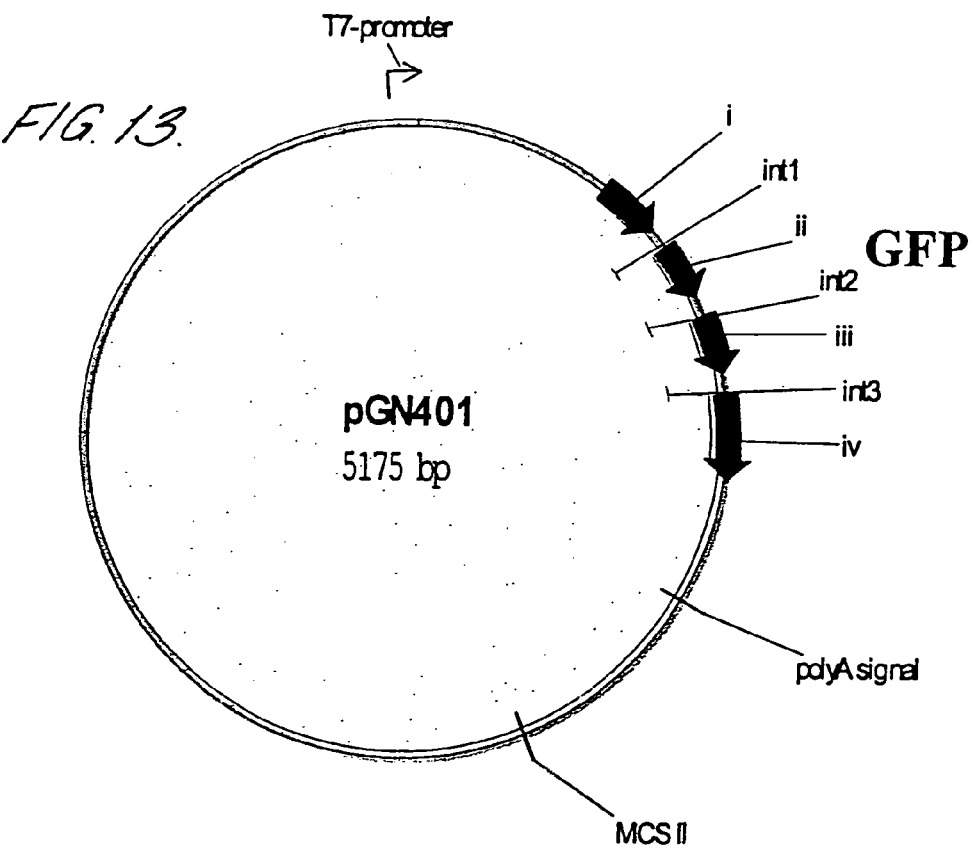
FIG. 13 is a representation of plasmid pGN401.

To test expression and functionality of T7 RNA polymerase in *C. elegans* under the regulation of the SERCA promoter, pGN108, which encodes the T7RNA polymerase under the control of the SERCA promoter was injected into *C. elegans*. A test vector was co-injected. This test vector encodes for GFP under the control of a T7 promoter (pGN401 in FIG. 13). The plasmid pGN401 was constructed by inserting two overlapping oligo's oGN41 (CCCGGGATTAATAC-GACTCACTATA; SEQ ID NO:23) and oGN42 (CCGGTAT-AGTGAGTCGTATTAATCCCGGGAGCT; SEQ ID NO:24) in the SacI/AgeI opened Fire vector pPD97.82, generating a T7 promoter. Furthermore a selection marker was co-injected to select for transformants (rol6, pRF4). The latter selection vector pRF4 is well known to persons skilled in the art. Transgenic F1 could easy be isolated as they display the rol 6 phenotype. These transgenic *C. elegans* all expressed GFP in the pharynx, the vulval muscle, the tail and the body wall muscle. This data show clearly that the T7 RNA polymerase is functionally expressed under the regulation of the SERCA promoter, and that the expressed T7 RNA polymerase binds to the T7 promoter present in pGN401 and initiates transcription of the GFP gene, which is then functionally expressed, resulting in fluorescence in the muscle tissues where SERCA is inducing the expression of the T7 RNA polymerase.

Example 3

Construction of a Vector for Ubiquitous Expression of T7 Polymerase in *C. elegans*

Figure 14:
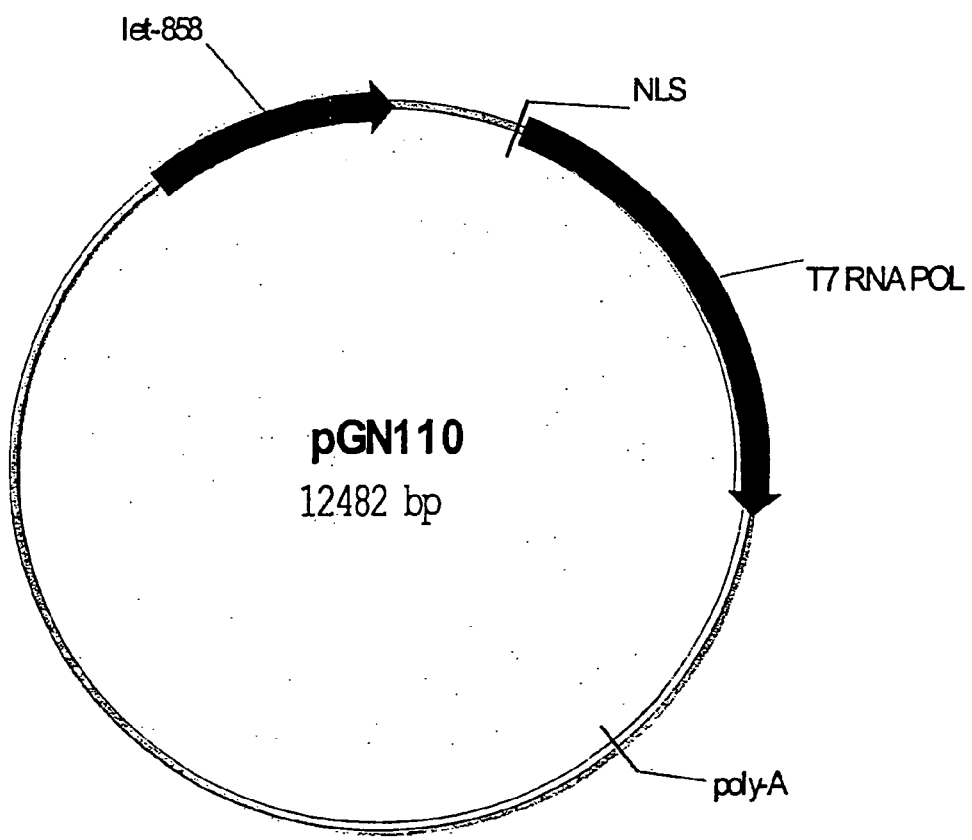
FIG. 14 is a representation of plasmid pGN110.
Figure 15:
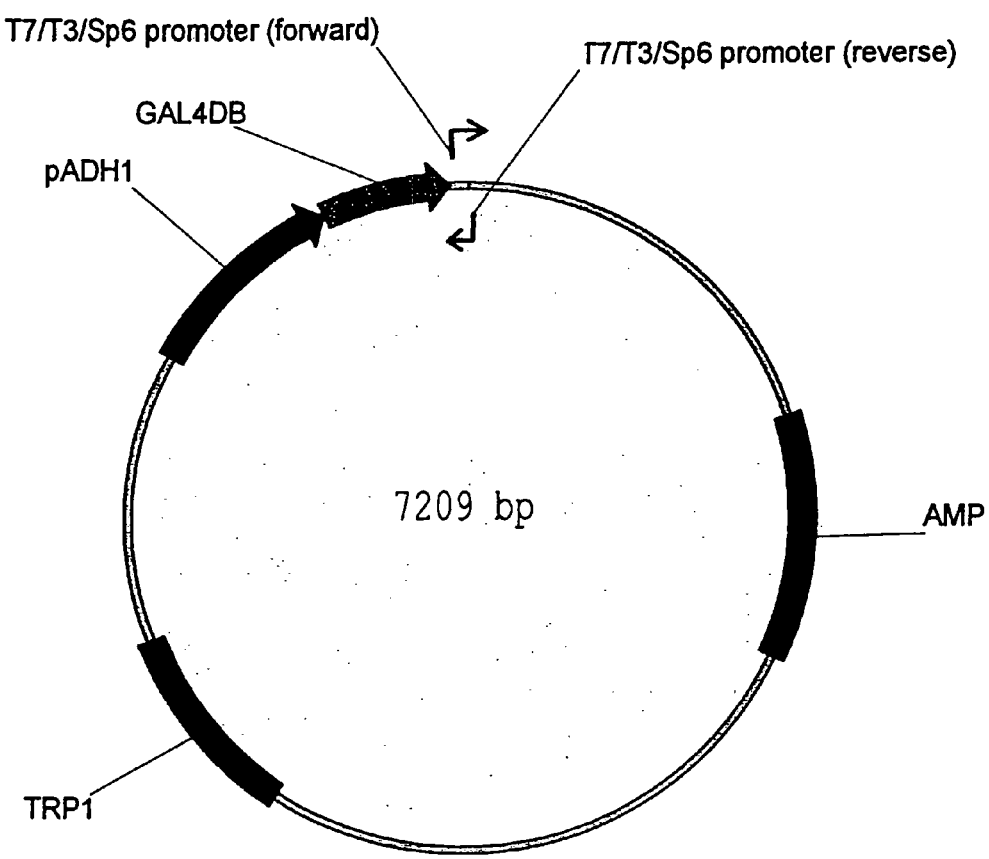
FIG. 15 is a representation of plasmid pAS2 with forward and reverse T7/T3/SP6 promoters.

The NLS-T7 RNA polymerase fusion gene was isolated from pGN108 with XmaI/Bsp1201 and cloned into the Fire vector pPD103.05 digested with XmaI/Bsp120I. This results in a vector wherein the T7 RNA polymerase is cloned under the regulation of the let858 promoter. This specific promoter enables the expression of T7 RNA polymerase in all tissues. The resulting plasmid was named pGN110 (FIG. 14)

Example 4

Figure 12:
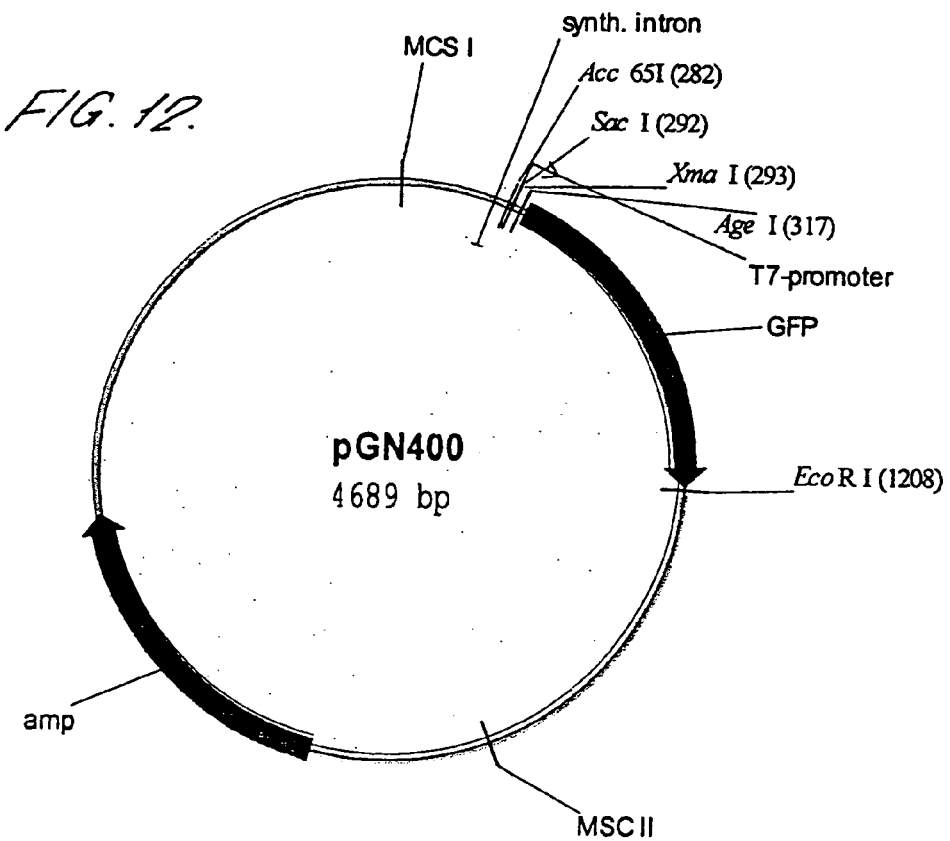
FIG. 12 is a representation of plasmid pGN400.

Construction of a Vector for T7 RNA Polymerase Mediated Expression of DNA Fragments, Genes, and cDNA's Under the Control of a T7 Promoter The Fire vector pPD97.82 was digested with SacI/AgeI and a T7 promoter sequence was generated by insertion of two overlapping oligo's oGN41 (CCCGGGATTAATAC-GACTCACTATA; SEQ ID NO:23) and oGN42 (CCGGTAT-AGTGAGTCGTATTAATCCCGGGAGCT; SEQ ID NO:24) into the SacI/Age/restriction endonuclease sites. This construct (pGN400 FIG. 12) contains a GFP open reading frame cloned between SacI and EcoRI restriction endonuclease sites under the regulation of the T7 promoter. Any gene, cDNA, or DNA fragment can be cloned in this vector by deleting the GFP gene as a AgeI/SacI fragment and cloning the DNA fragment of interest into the vector. Preferentially the DNA fragment of interest can be obtained by PCR amplification, inserting the SacI/AfeI sites in the primers. The resulting DNA fragment after PCR amplification is the digested and the GFP gene in pGN400 is replaced by the amplified DNA fragment. Every vector that contains a T7 promoter could be used for the purpose of T7 RNA polymerase induced expression in *C. elegans*, such as the commercially available pGEM vectors and the pBluescript vectors. This is clearly shown by the pGN401 vector which expresses GFP under the regulation of the T7 promoter in a transgenic *C. elegans* which expresses T7 RNA polymerase.

The use of pGN400 has the advantage that the vector includes a 3'UTR fragment from unc-54 which enhances the transcription or stability of the RNA.

Generation of Permanent, Tissue Specific "Pseudo knock-out" RNAi C elegans Lines At present, gene knock outs in *C. elegans* are obtained after random, large scale mutagenesis and PCR based sib-selection. This method is bulky, very time consuming and tedious. It has been described that introducing double stranded RNA into a cell results in potent and specific interference of expression of endogenous genes. In *C. elegans* gene expression can be down regulated by injection of RNA into the body cavity of the worm, soaking the worm in a solution containing dsRNA or feeding *E. coli* that express dsRNA corresponding to the gene of interest. *C. elegans* cells have the ability to take in dsRNA from their extracellular environment. It has been reported that mRNA is the target of this ds RNA mediated genetic interference (Montgomery and Fire 1998). It is also suggested that the targeted RNA is degraded in the nucleus before translation can occur. Although the RNAi mediated reduction of gene expression can be passed on to the next generations, heritability is poor and the effect is rapidly lost during further offspring. This is probably due to a continued decrease of the dsRNA pool. We propose here a method to construct *C. elegans* lines with a permanent, inheritable, RNAi phenotype. The method encompasses the generation of transgenic *C. elegans* lines by introducing plasmids containing cDNA fragments of the target gene in the sense and antisense orientation under control of a worm promoter or by transcription of an inverted repeat of the cDNA from a single construct. Alternatively, ds RNA can be transcribed from a vector harboring a cDNA flanked by two T7 promoters in a *C. elegans* strain that expresses T7 polymerase. The result is a transgenic worm with an heritable stable "pseudo knock-out" phenotype. The expression of the cDNA or the T7 polymerase can be general and constitutive but could also be regulated under a tissue specific promoter. In contrast to RNAi induced by external ds RNAi (injected, soaked or feeded) this method would enable to obtain conditional, tissue specific inhibition of gene expression.

Inhibition of unc-22 Expression by RNA Interference Results in a "Twitching" Phenotype Unc 22 cDNA (exon 22) was cloned in sense and antisense orientation in pPD103.05. (A. Fire nr L2865) containing the let 858 promoter that is capable of expressing RNA sequences in all tissues. The resulting plasmids were named pGN205 (FIG. 19*a*) and pGN207 (FIG. 19*b*). These constructs were introduced into *C. elegans* together with a selectable marker (rol-6; GFP). Transgenic F1 individuals (expressing rol-6 or GFP) showed a "twitching" phenotype indicating that RNAi could be mediated by endogenous transcription of RNA from transgenic DNA. The RNAi phenotype co-segregated with the selectable marker into further offspring. This resulted in the generation of C. elegans lines with permanent RNAi phenotype.

Generation of Stable Lines T7 RNA Polymerase Lines and Generation of Dual Transgenic Worms An expression system in C. elegans based on an exogenous RNA polymerase demands two plasmids. One is encoded for the RNA polymerase under the control of a specific promoter, while the other plasmid encodes for the DNA fragment to be expressed, under the regulation of the T7 promoter. In the case of semi stable RNAi also designated pseudo stable knockouts, the DNA of interest is cloned between two T7 promoters so that dsRNA can be produced.

As the T7 RNA polymerase expression system is known to be a high expression system this will result in problems to generate dually transgenic animals. If the gene to be expressed in the C. elegans nematode is toxic, this will result in lethal effects and hence in the construction of a C. elegans without highly regulated stable expression of the gene of interest. If the gene of interest is essential for the survival of the organism, RNAi with a DNA fragment from this gene will also result in lethal effects, so that pseudo-stable knockouts are not possible.

To overcome this problem the present inventors have designed a system consisting of two transgenic animals. The first animal is transgenic for the T7 RNA polymerase, This T7 RNA polymerase can be expressed in all cells or specific cells or tissues as has been shown in previous examples. The second transgenic animal is transgenic for the DNA fragment of interest. This can be a gene or cDNA linked to a T7 promoter, or if one wants to perform RNAi a DNA fragment of such gene cloned between two T7 promoters.

Both transgenic animals are viable and do not show any aberrant phenotypes. This is because the T7 RNA polymerase expressed in the first transgenic organism is not toxic for the organism, even if expressed at relative high levels. In the second transgenic organism, the gene of interest is not expressed or the dsRNA is not produced as these transgenic animals do not contain the T7 RNA polymerase.

Expression of the gene or cDNA of interest or RNAi with a DNA fragment can now be obtained by mating the two transgenic animals. The offspring of these are dually transgenic and express the gene of interest or express dsRNA of the DNA fragment of interest. To generate sufficient males in such a mating, one of the transgenic animals males can be a C. elegans mutant with a phenotype favouring generation of males. An example of such a mutant is him-5. Preferentially such a mutant will be used to make a C. elegans transgenic for T7 RNA polymerase, while the hermaphrodite harbors the DNA fragment under the regulation of the T7 promoter.

To select efficiently for the dual transgenic offspring a second transgene can be introduced in the second transgenic animal. This transgene contains a reporter gene under the regulation of the T7 promoter. The reporter gene can be GFP, luciferase, Beta galactosidase, or beta-lactamase. An example of such a transgene are the vectors pGN40O and pGN40I.

To obtain inducible, tissue specific expression of a transgene in C. elegans we can make male stock (i.e. him-5) carrying the T7 polymerase construct under the control of different C. elegans promoters that enable tissue specific expression such as). These males can be crossed with hermaphrodites carrying the gene of interest under the control of a T7 promoter.

Furthermore, the transgenes can be integrated into the genome of the animal. Methods to generate stable integration of a plasmid into the genome of the animal have been described (Methods in Cell Biology, Vol. 48, 1995, ed. by Epstein and Shakes, Academic Press) and involve radiation of the animal. This can be done for both animals, but preferentially, the animals expressing the T7 RNA polymerase are subject to such treatment. This result in a collection of C. elegans nematodes that stably express T7 RNA polymerase under the control of various promoters. Examples of such promoters are the myo-2 (pharynx expression), myo-3 (body wall muscles), eg1-15 (vulval muscles), unc-119 (pan-neuron), SERCA (muscles), let858 (all cells) ges-1 (gut).

Construction of RNAi T7 Promoter Yeast Two Hybrid Vectors pGAD424 with Forward and Reverse T7/T3 and or Sp6

Figure 16:
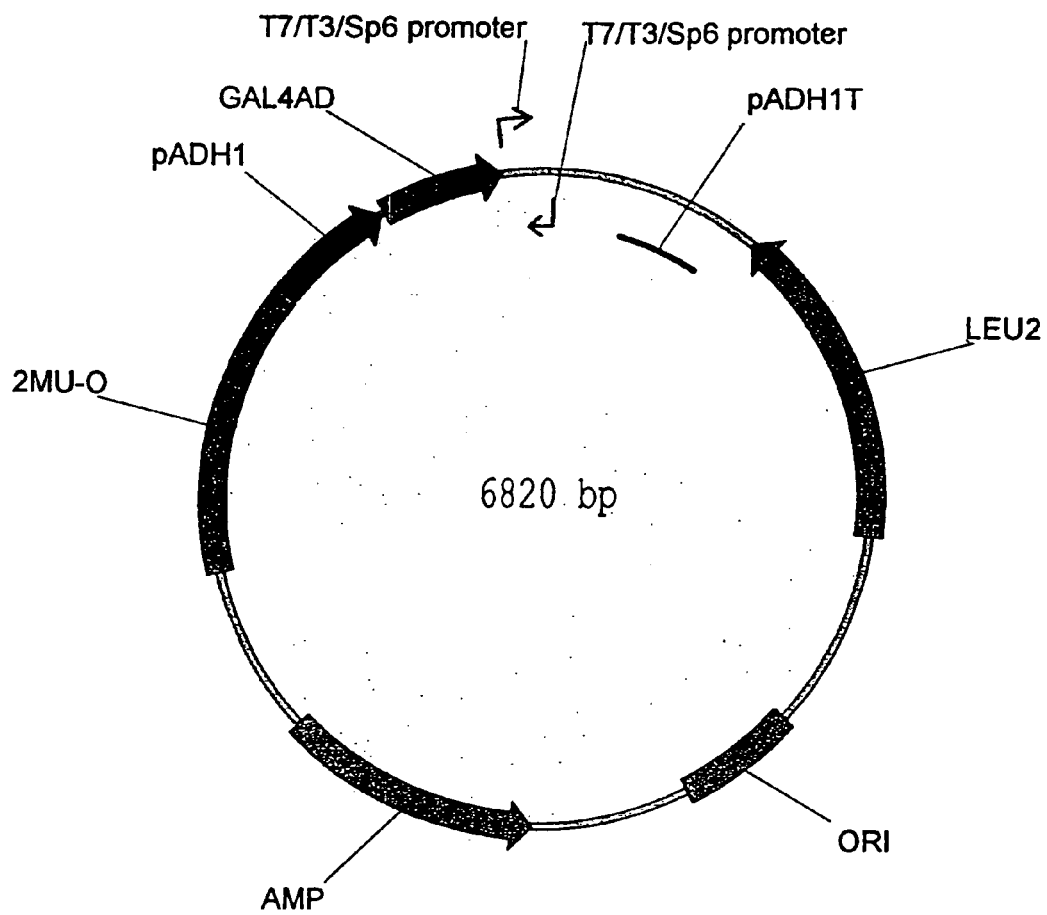
FIG. 16 is a representation of plasmid pGAD424 with forward and reverse T7/T3/SP6 promoters.
Figure 17:
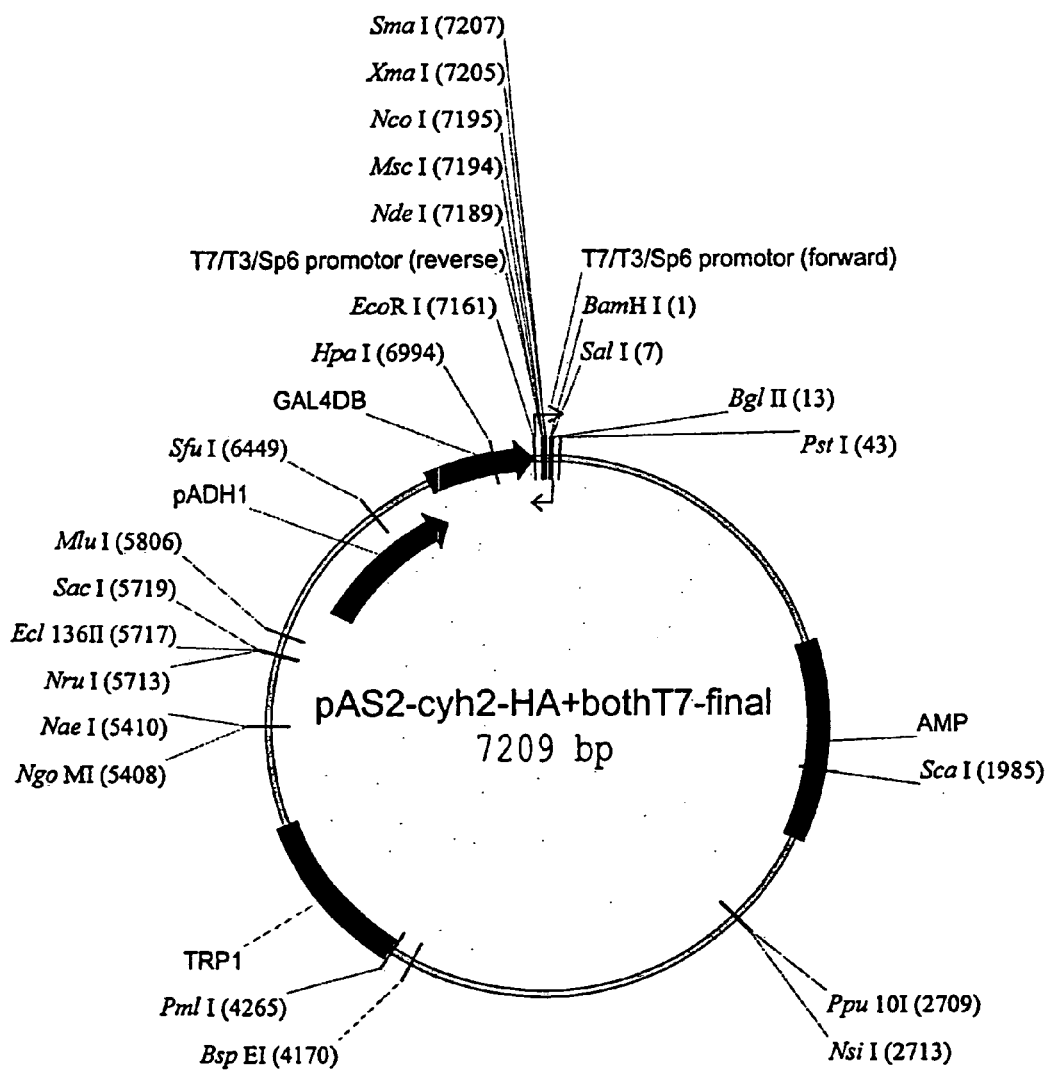
FIG. 17 is a representation of plasmid pAS2-cyh2-HA+, both T7-final.
Figure 18:
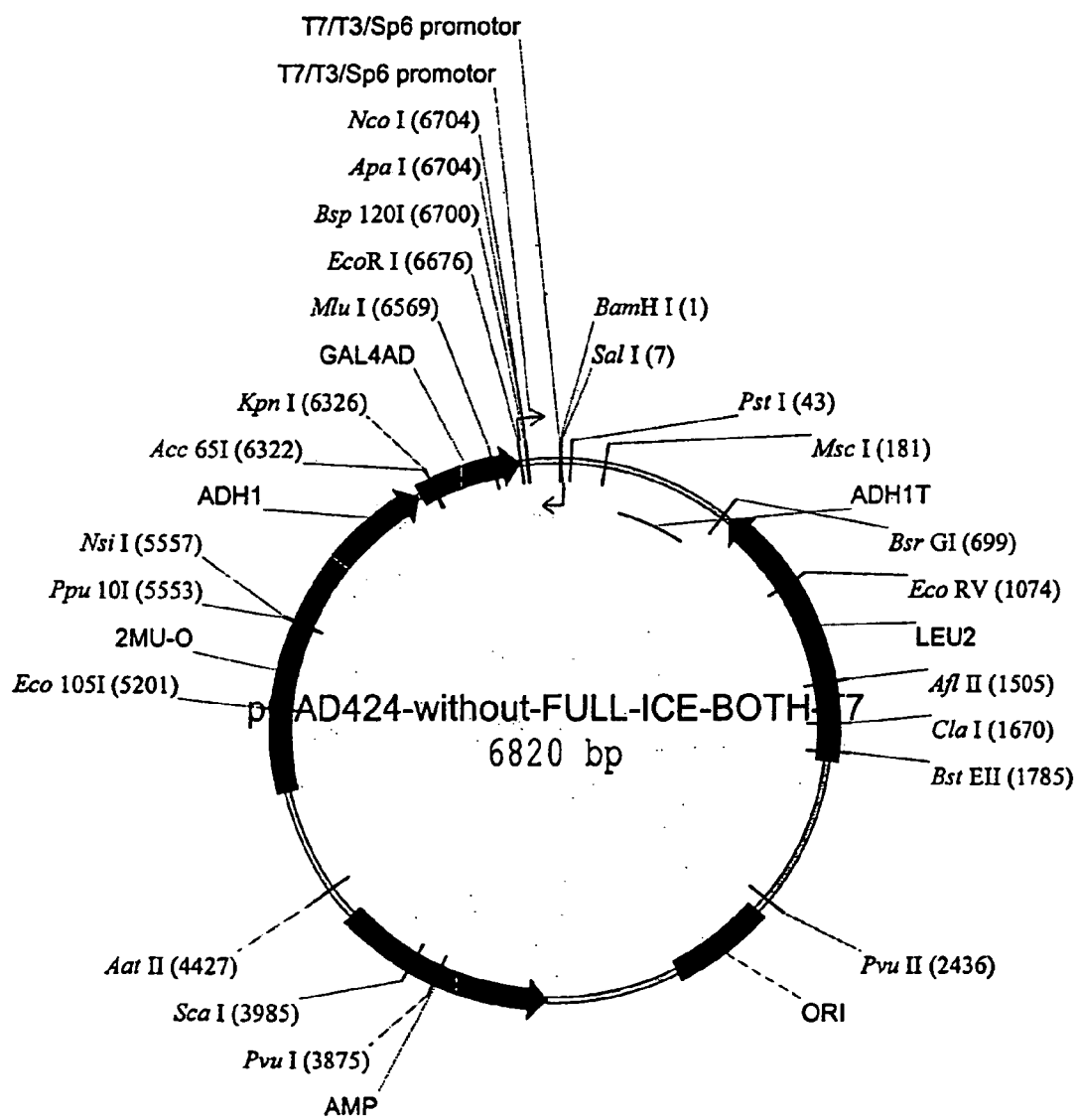
FIG. 18 is a representation of plasmid pGAD424-without-FULL-ICE-BOT-H-T7.

In most two-hybrid experiments a cDNA library is cloned in plasmid pGAD424 (FIG. 16) which has been engineered with additional restriction sites in the polylinker such as a NcoI site (Clontech). This library allows for screening of binding proteins in a yeast two hybrid experiment. We constructed a new yeast two hybrid vector with the same possiblilities to perform yeast two hybrid, but which contain two additional T7 promoters, so that the vector can be used for T7 RNA polymerase induced pseudo-stable knock-outs. For this we inserted a forward T7 by using a T7-linker (consisting of the following primers aattcttaatacgactcactataggggcc (SEQ ID NO:25) and catgggccctatagtgagtcgtattaag (SEQ ID NO:26)) into the EcoRI-NcoI site of pGAD424. The resulting vector was designated pGAD424-without-FULL-ICE-both-T7. Care was taken to eliminate stop codons and using maximal polylinker compatible amino acids. We adopted the same strategy for the reverse T7 (consisting of both primers gatccgtcgacagatctccctatagtgagtcgtattactgca (SEQ ID NO:27) and gtaatacgactcactatagggagatctgtcgacg (SEQ ID NO:28)) with BamH1 and Pst1. To avoid loss of SalI, we included this site in the primer.

The SalI site is important as most libraries are cloned in this site, adapters are available. This makes the newly constructed vector compatible with existing vectors.

pAS2 with with Forward and Reverse T7/f3 and or Sp6

An analogous yeast two hybrid vector was constructed based on pAS2 (Clontech). By partial EcoRV digestion we were able to remove a significant part of the cyh2 gene. The right construct can be isolated and checked by a restriction digest with BglII. this restriction site is present in the EcoRV fragment of PAS2 to be eliminated. This elimates the cyh2 gene which is slightly toxic gene and involved in growth retardation. This gene is non-essential for the performing of RNAi and Yeast two hybrid experiments. After the elimination of the EcoRV fragment, The EcoRI restriction site which is located between the DNA sequence encoding for GAL4 DB and HA (epitope) becomes unique for the plasmid, and can be used to subsitute HA with a T7 promoter containing linker. This ensures persistence of all restriction sites, allowing both in frame cloning and compatibility with previous vectors and pGAD424. We used the following linker (primers:_aattcttaatacgactcactatagggcc (SEQ ID NO:25) and tatgccctatagtgagtcgtattaag (SEQ ID NO:29)) using EcoRI and Nde1 cloning sites. We adopted the same strategy for the reverse T7 (primers: gatccgtcgacagatctccctatagtgagtcgtattactgca (SEQ ID NO:27) and gtaatacgactcactatagggagatctgtcgacg (SEQ ID NO:28)) with BamH1 and Pst1. To avoid loss of Sal1 we included it in the primer. The resulting vector was designated pAS2-cyh2-HA+both T7-final.

Having the T7 promoter (or alternatively the T3, or SP6 promoter) in pGAD424 allows to go quickly from interacting protein to RNAi and assigning function to the isolated DNA fragment. An additional advantage is the ability to make by in vitro transcription coupled to in vitro translation (There is an ATG in frame with either GAL4 DB or GAL4AD) labeled protein which can be used for in vitro controls (e.g. pull down assays) of the actual protein-protein interaction.

The sequences of the plasmids produced and the SP6 and T3 polymerase are identified in the Sequence Listing provided below:

What is claimed is:

1. A bacterium comprising an expression vector that comprises promoters flanking a double stranded DNA sequence such that the promoters initiate transcription of said double stranded DNA sequence to produce double stranded RNA upon binding of a transcription factor to said promoters, whereby said double stranded RNA is produced in said bacterium, in which said expression vector comprises two identical promoters flanking said double stranded DNA sequence.

2. The bacterium according to claim 1, in which said transcription factor is a phage polymerase.

3. The bacterium according to claim 2, in which said promoters are T7 promoters.

4. The bacterium according to claim 1, wherein said bacterium is adapted to express said transcription factor.

5. The bacterium according to claim 4, wherein said transcription factor is T7 polymerase.

6. The bacterium according to claim 1, in which said double stranded DNA sequence is obtained from *C. elegans*.

7. The bacterium according to claim 6, in which said double stranded DNA sequence is a *C. elegans* cDNA or cDNA fragment.

8. The bacterium according to claim 1, wherein said bacterium is *E. coli*.

9. The bacterium according to claim 8, wherein said *E. coli* is a RNAse III negative strain.

10. The bacterium according to claim 1, in which said double stranded DNA sequence is obtained from a pest.

11. The bacterium according to claim 10, in which said pest is a parasitic pest.

12. The bacterium according to claim 10, in which said pest is a nematode.

13. The bacterium according to claim 12, in which said nematode is a parasitic nematode.

14. The bacterium according to claim 10, in which said double stranded DNA sequence is a cDNA, cDNA fragment, or exon.

* * * * *